United States Patent [19]
Lasky et al.

[11] Patent Number: 6,117,977
[45] Date of Patent: Sep. 12, 2000

[54] TYPE C LECTINS

[75] Inventors: Laurence A. Lasky, Sausalito; Kai Wu, San Bruno, both of Calif.

[73] Assignee: Genentech, Inc., So. San Francisco, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/840,062

[22] Filed: Apr. 24, 1997

Related U.S. Application Data

[63] Continuation of application No. 08/637,021, Apr. 24, 1995, abandoned.
[60] Provisional application No. 60/052,524, Apr. 24, 1995.
[51] Int. Cl.[7] .......................... C07K 14/00; C07H 21/04; C12N 15/00; C12N 15/03
[52] U.S. Cl. .................... 530/350; 435/69.1; 435/320.1; 536/23.1; 536/325; 536/252.3
[58] Field of Search .................................... 530/350, 395, 530/387.3; 536/23.4, 23.5; 435/320.1, 252.3, 325, 358, 69.1, 69.7

[56] References Cited

U.S. PATENT DOCUMENTS 5,116,964 5/1992 Capon et al. .......................... 536/23.5
5,612,190 3/1997 Arita et al. .............................. 435/69.1

OTHER PUBLICATIONS

Goochee et al. Bio/Technology 9, 1347–1355, 1991.
George et al. Macromolecular Sequencing and Synthesis, pp. 127–149. Ed. by D. H. Schlesinger. Alan R. Liss, Tave.: New York, 1988.
Rudinger, J et al., Peptide Hormones, ed. J. A. Parsons, University Park Press, Baltimore, pp. 1–7, 1997.
Wu et al., "Characterization of a Novel Member of the Macrophage Mannose Receptor Type C Lectin Family" *The Journal of Biological Chemistry* 271:21323–21330 (1996).
Arbones et al., "Lymphocyte homing and leukocyte rolling and migration are impaired in L–selectin (CD62L) deficient mice" *Immunity* 1:247–260 (1994).
Bezouska et al., "Oligosaccharide ligands for NKR–P1 protein activate NK cells and cytotoxicity" *Nature* 372(6502):150–157 (1994).
Drickamer, "Engineering galactose–binding activity into a C–type mannose–binding protein" *Nature* 360:183–186 (1992).
Drickamer, K., "Two distinct classes of carbohydrate recognition domains in animal lectins" *Journal of Biological Chemistry* 263:9557–9560 (1988).
Erbe et al., "Identification of an E–selectin region critical for carbohydrate recognition and cell adhesion" *Cell. Biol.* 119(1):215–227 (1992).
Graves et al., "Insight into E–selectin/ligand interaction from the crystal structure and mutagenesis of the lec/EGF domains" *Nature* 367 (6463):532–538 (1994).

Harris et al., "Characterization of the murine macrophage mannose receptor: demonstration that the downregulation of receptor expression mediated by interferon–gamma occurs at the level of transcription" *Blood* 80(9):2363–73 (1992).
Harris et al., "The exon–intron structure and chromosomal localization of the mouse macrophage mannose receptor gene Mrcl: identification of a Ricin–like domain at the N–terminus of the receptor." *Biochem. & Biophys. Res. Comm.* 198(2):682–692 (1994).
Higashino et al., "Structural comparison of phospholipase–A2–binding regions in phospholipase–A2 receptors from various mammals" *European Journal of Biochemistry* 225(1):375–782 (1994).
Iobst et al., "Binding of sugar ligands to Ca+2–dependent animal lectins. I.Analysis of mannose binding by site–directed mutagenesis" *Journal of Biological Chemistry* 269(22):15505–15511 (1994).
Ishizaki et al., "Molecular cloning of pancreatic group I phospholipase A2 receptor" *Journal of Biological Chemistry* 269(8):5897–5904 (1994).
Jiang et al., "The receptor DEC–205 expressed by dendritic cells and thymic epithelial cells is involved in antigen processing" *Nature* 375 (6527):151–155 (1995).
Kim et al., "Organization of the gene encoding the human macrophage mannose receptor (MRCI)" *Genomics* 14(3):721–727 (1992).
Kogan et al., "A single amino acid residue can determine the ligand specificity of E–selectin" *Journal of Biological Chemistry* 270(23):14047–14055 (1995).
Lambeau et al., "Cloning and expression of a membrane receptor for secretory phospholipases A2" *Journal of Biological Chemistry* 269(3):1575–1578 (1994).
Lasky et al., "An endothelial ligand for L–selectin is a novel mucin–like molecule" *Cell* 69:927–938 (1992).
Lasky, L., "Selectin–carbohydrate interactions and the initiation of the inflammatory response" *Ann. Rev. Biochem.* 64:113–139 (1995).
Lipscombe et al., "Distinct physicochemical characteristics of human mannose binding protein expressed by individuals of differing genotype" *Immunology* 85(4):660–667 (1995).
Mayadas et al., "Leukocyte rolling and extravasation are severely compromised in P selectin–deficient mice" 74 3(3):541–554 (1993).

(List continued on next page.)

*Primary Examiner*—Elizabeth C. Kemmerer
*Assistant Examiner*—Nirmaz S. Basi
*Attorney, Agent, or Firm*—Mark T. Kresnak

[57] ABSTRACT

The invention concerns novel members of the endocytic type C lectin family and methods and means for producing them. The native polypeptides of the invention are characterized by containing a signal sequence, a cysteine rich domain, a fibronectin type II domain, 8 type C lectin domains, a transmembrane domain and a cytoplasmic domain. Nucleotide sequences encoding such polypeptides, vectors containing the nucleotide sequences, recombinant host cells transformed with the vectors, and methods for the recombinant production for the novel type C lectins are also within the scope of the invention.

34 Claims, 24 Drawing Sheets

OTHER PUBLICATIONS

Summerfield et al., "Mannose binding protein gene mutations associated with unusual and severe infections in adults" *Lancet* 345(8954):886–889 (1995).

Taylor et al., "Contribution to ligand binding by multiple carbohydrate–recognition domains in the macrophage mannose receptor" *Journal of Biological Chemistry* 267(3):1719–1726 (1992).

Taylor et al., "Primary structure of the mannose receptor contains multiple motifs resembling carbohydrate–recognition domains" *Journal of Biological Chemistry* 265(21):12156–62 (1990).

Taylor et al., "Structural requirements for high affinity binding of complex ligands by the macrophage mannose receptor" *Journal of Biological Chemistry* 268(1):399–404 (1993).

Weis et al., "Structure of a C–type mannose–binding protein complexed with an oligosaccharide" *Nature* 360:127–134 (1992).

Weis et al., "Structure of the calcium–dependent lectin domain from a rat mannose–binding protein determined by MAD phasing" *Science* 254:1608–1615 (1991).

Zvaritch et al., "Endocytic properties of the M–type 180–kDa receptor for secretory phospholipases A2" *Journal of Biological Chemistry* 271(1):250–257 (1996).

```
elam    1 MTYDEASAYCQQRYTHLVAHQNKEEIEYLNSILSYSPSYYWIGIRKVNNV
T11885  1 LKWSEAQFSCEQQEAQLVTHTNPLEQAFITASLPNVTFDLWIGLHASQRD elam   51 WVWVGTQKPLTEEAKNW
T11885 51 FQWVEQEPLMYANWATW
```

FIG. 1

```
  1 GAATTCGGCT TCCATCCTCA TACGACTCAC TATAGGGCTC GAGCGCCGCC CGGGCAGGTC GCCGGCGGTC
 71 ATCCGAGCAC AGCGCTAGGG CTGTCTCTGC ACGCAGCCCT GCCGTGCGCC CTCCGTACTC TCGTCCTCCG
141 AGCGCCGCAG GGATGGTACC CATCCGACCT GCCCTCGCGC CCTGGCTTCG TCACCTGCTG CGCTGCTCT
  1               M  V  P  I  R  P  A  L  A  P  W  P  R  H  L  L  R  C  V  L
211 TGCTTCTCGG GGGACTGCGT CTCGGCCACC CGGGCGACTC CGGCCGCCGC CTCCCTGGAGC CTGATGTCTT
 21  L  L  G  G  L  R  L  G  H  P  A  D  S  A  A  A  L  L  E  P  D  V  F
281 CCTCATCTTC AGCCAGGGGA TGCAGGGCTG TCTGGAGGCC CAGGGTGTGC AGGTCCGAGT CACCCCATTC
 44  L  I  F  S  Q  G  M  Q  G  C  L  E  A  Q  G  V  Q  V  R  V  T  P  F
351 TGCAATGCCA GTCTCCCTGC CCAGCGCTGG AAGTGGGTCT CCCGGAACCG ACTCTTCAAC CTGGGTGCCA
 67  C  N  A  S  L  P  A  Q  R  W  K  W  V  S  R  N  R  L  F  N  L  G  A  T
421 CACAGTGCCT GGGTACAGGC TGGCCAGTCA CCAACACCAC AGTTCCTTTG GGCATGTATG AGTGTGACAG
 91  Q  C  L  G  T  G  W  P  V  T  N  T  T  V  S  L  G  M  Y  E  C  D  R
491 AGAGGCCTTG AGTCTTCGAT GGCAGTGTTC GTACACTAGG GGACCAGTTG TCCCTGCTTC TGGGGGCTCG
114  E  A  L  S  L  R  W  Q  C  S  Y  T  R  G  P  V  V  S  G  G  S
561 TGCAAGCAAT GCATCCAAGC CTGGCACCTG GAGCGCGGTG ACCAGACCCG CAGTGGCCAT TGGAACATCT
137  C  K  Q  C  I  Q  A  W  H  L  E  R  G  D  Q  T  R  S  G  H  W  N  I  Y
631 ATGGCAGTGA AGAAGACCTA CTTACTATGA TGTGCTCGAC CTTACTATGA GGTCTACACC ATCCAGGGAA ACTCACACGG
161  G  S  E  E  D  L  C  A  R  P  Y  Y  E  V  Y  T  I  Q  G  N  S  H  G
701 AAAGCCGTGC ACTATCCCCT TCAAATACGA CAACCAGTGG TTCCACGGCT GCACCAGCAC TGGCAGAGAA
184  K  P  C  T  I  P  F  K  Y  D  N  Q  W  F  H  G  C  T  S  T  G  R  E
```

FIG. 2A

```
 771 GATGGGCACC TGTGGTGTGC CACCACCCAG GACTACGGCA AAGATGAGCG CTGGGGCTTC TGCCCCATCA
 207  D  G  H  L  W  C  A  T  T  Q  D  Y  G  K  D  E  R  W  G  F  C  P  I  K

841 AGAGTAACGA CTGTGAGACC TTCTGGGACA AAGACCAGCT GACTGACAGC TGTTACCAGT TTAACTTCCA
 231  S  N  D  C  E  T  F  W  D  K  D  Q  L  T  D  S  C  Y  Q  F  N  F  Q

911 ATCCACACTG TCCTGGAGGG AGGCCTGGGC CAGCTGCGAG CAGCAGGGTG GAGTATCACG
 254  S  T  L  S  W  R  E  A  W  A  S  C  E  Q  Q  G  A  D  L  L  S  I  T

981 GAGATCCACG AGCAGACCTA CATCAACGGG CTCCTCACGG GCTACAGCTC CACGCTATGG ATTGGCCTTA
 277  E  I  H  E  Q  T  Y  I  N  G  L  L  T  G  Y  S  S  T  L  W  I  G  L  N

1051 ATGACCTGGA TACCAGTGGG GGCTGGCAGT GGTCAGACAA CTCACCCCTC AAGTACCTCA ACTGGGAGAG
 301  D  L  D  T  S  G  G  W  Q  W  S  D  N  S  P  L  K  Y  L  N  W  E  S

1121 TGATCAGCCG GACAACCCAG GTGAGGAGAA CTGTGGAGTG ATCCGGACTG AGTCCTCAGG CGGCTGGCAG
 324  D  Q  P  D  N  P  G  E  E  N  C  G  V  I  R  T  E  S  S  G  G  W  Q

1191 AACCATGACT GCAGCATCGC CCTGCCCTAT GTTTGCAAGA AGAAACCCAA CGCTACGGTC GAGCCCATCC
 347  N  H  D  C  S  I  A  L  P  Y  V  C  K  K  K  P  N  A  T  V  E  P  I  Q

1261 AGCCAGACCG GTGGACCAAT GTCAAGGTGG AATGTGACCC CAGCTGGCAG CCCTTCCAGG GCCACTGCTA
 371  P  D  R  W  T  N  V  K  V  E  C  D  P  S  W  Q  P  F  Q  G  H  C  Y

1331 CCGCCTGCAG GCCGAGAAGC GCAGCTGGCA GGAGTCCAAG AGGGCGTGTC TGCGGGGTGG GGGTGACCTC
 394  R  L  Q  A  E  K  R  S  W  Q  E  S  K  R  A  C  L  R  G  G  G  D  L

1401 CTTAGCATCC ACAGCATGGC TGAGCTGGAG TTCATCACCA AACAGATCAA GCAAGAGGTG GAGGAGCTAT
 417  L  S  I  H  S  M  A  E  L  E  F  I  T  K  Q  I  K  Q  E  V  E  E  L  W
```

FIG. 2B

```
1471 GGATTGGCCT CAATGATTTG AAACTGCAGA TGAATTTGA GTGGTCCGAC GGGAGCCTCG TGAGCTTCAC
441   I  G  L    N  D  L    K  L  Q  M    N  F  E    W  S  D    G  S  L  V    S  F  T

1541 CCACTGGCAC CCCTTTGAGC CCAACAACTT TCGTGACAGC CTGGAGGACT GTGTCACCAT CTGGGGCCG
464   H  W  H    P  F  E  P    N  N  F    R  D  S    L  E  D  C    V  T  I    W  G  P

1611 GAAGGACGCT GGAACGACAG TCCCTGTAAC CAGTCCTTGC CATCCATTTG CAAGAAGGCA GGCCGGCTGA
487   E  G  R  W    N  D  S    P  C  N    Q  S  L  P    S  I  C    K  K  A    G  R  L  S

1681 GCCAGGGCGC GACCACGACT GACCACGACT GCCGGAAGGG TTGGACGTGG CATAGCCCAT CCTGCTACTG
511   Q  G  A    D  H  D  C    R  K  G    W  T  W    H  S  P  S    C  Y  W

1751 GCTGGGAGAG GACCAAGTGA TCTACAGTGA TGCCCCGGGC CTGTGTACTG ACCATGGCTC TCAGCTGGTC
534   L  G  E    D  Q  V  I    Y  S  D    A  R  R    L  C  T  D    H  G  S    Q  L  V

1821 ACCATCACCA ACAGGTTTGA GCAGGCCTTC GTCAGCAGCC TCATCTATAA CTGGGAGGGC GAATACTTCT
557   T  I  T  N    R  F  E    Q  A  F    V  S  S  L    I  Y  N    W  E  G    E  Y  F  W

1891 GGACAGCCCT GCAAGACCTC AACAGTACTG GCTCCTTCCG TTGGCTCAGT GGGGATGAAG TCATATATAC
581   T  A  L    Q  D  L    N  S  T  G    S  F  R    W  L  S    G  D  E  V    I  Y  T

1961 CCATTGGAAT CGAGACCAGC CTGGGTACAG ACGTGGAGGC CGGGGGATGAAG TGGCCACTGG CAGTGCCATG
604   H  W  N    R  D  Q  P    G  Y  R    R  G  G    C  V  A  L    A  T  G    S  A  M

2031 GGACTGTGGG AGGTGAAGAA CTGCACATCG TTCCGGGCTC GCTACATCTG CCGACAGAGC CTGGGCACAC
627   G  L  W  E    V  K  N    C  T  S    F  R  A  R    Y  I  C    R  Q  S    L  G  T  P

2101 CGGTCACACC AGAGCTGCCT GGGCCAGACC CCACGCCCAG CCTCACTGGC CCTCGTCCCC AGGGCTGGGT
651   V  T  P    E  L  P    G  P  D  P    T  P  S    L  T  G    S  C  P  Q    G  W  V
```

FIG. 2C

```
2171 CTCAGACCCC AAACTCCGAC ACTGCTATAA GGTGTTCAGC TCAGAGCGGC TGCAGGAGAA GAAGAGTTGG
 674  S  D  P   K  L  R  H   C  Y  K    V  F  S    S  E  R  L    Q  E  K    K  S  W

2241 ATCCAGGCCC TGGGGGTCTG CCGGGAGTTG GGGGCCCAGC TGCTGAGTCT GGCCAGCTAT GAGGAGGAGC
 697  I  Q  A  L   G  V  C    R  E  L    G  A  Q  L    L  S  L    A  S  Y    E  E  E  H

2311 ACTTTGTGGC CCACATGCTC AACAAGATCT TTGGTGAGTC AGAGCCTGAG AGCCATGAGC AGCACTGGTT
 721  F  V  A   H  M  L    N  K  I  F    G  E  S    E  P  E    S  H  E  Q    H  W  F

2381 TTGGATTGGC CTGAACCGCA GAGACCCTAG AGAGGGTCAC AGCTGGCGCT GGAGCCGACGG TCTAGGGTTT
 744  W  I  G   L  N  R  R    D  P  R    E  G  H    S  W  R  W    S  D  G    L  G  F

2451 TCCTACCACA ATTTTGCCCG GAGCCGACAT GATGACGATG ATATCCGAGG CTGTGCAGTG CTGGACCTGG
 767  S  Y  H  N   F  A  R    S  R  H    D  D  D  D    I  R  G    C  A  V    L  D  L  A

2521 CCTCCCTGCA GTGGGTACCC ATGCAGTGCC AGACGCAGCT TGACTGGATC TGCAAGATCC CTAGAGGTGT
 791  S  L  Q   W  V  P    M  Q  C  Q    T  Q  L    D  W  I    C  K  I  P    R  G  V

2591 GGATGTGCGG GAACCAGACA TTGGTCGACA AGGCCGTCTG GAGTGGGTAC GAGCTTCAGGA GGCCGAGTAC
 814  D  V  R   E  P  D  I    G  R  Q    G  R  L    E  W  V  R    F  Q  E    A  E  Y

2661 AAGTTTTTTG AGCACCACTC CTCGTGGGCG CAGGCACAGC GCATCTGCAC CTGGTTCCAG GCAGATCTGA
 837  K  F  F  E   H  H  S    S  W  A    Q  A  Q  R    I  C  T    W  F  Q    A  D  L  T

2731 CCTCCGTTCA CAGCCAAGCA GAACTGGGCT TCCTGGGGCA AAACCTGCAG AAGCTGTCCT CAGACCAGGA
 861  S  V  H   S  Q  A    E  L  G  F    L  G  Q    N  L  Q    K  L  S  S    D  Q  E

2801 GCAGCACTGG TGGATCGGCC TGCACACCTT GGAGAGTGAC GGACGCTTCA GGTGGACAGA TGGTTCTATT
 884  Q  H  W   W  I  G  L    H  T  L    E  S  D    G  R  F  R    W  T  D    G  S  I
```

FIG. 2D

| | | | | | | | |
|---|---|---|---|---|---|---|---|
| 2871 907 | ATAAACTTCA I N F I | TCTCTTGGGC S W A | ACCGGGAAAA P G K | CCTAGACCCA P R P I | TTGGCAAGGA G K D | CAAGAAGTGT K K C | GTATACATGA V Y M T |
| 2941 931 | CAGCCAGACA A R Q | AGAGGACTGG E D W | GGGGACCAGA G D Q R | CCTAGACCCA | GGCTTTGCCC A L P | TACATCTGTA Y I C K | AGCGCAGCAA R S N |
| 3011 954 | TAGCTCTGGA S S G | GAGACTCAGC E T Q P | CCCAAGACTT Q D L | GCCACCTTCA P P S | GCCTTAGGAG A L G G | GCTGCCCCTC C P S | CGGTTGGAAC G W N |
| 3081 977 | CAGTTCCTCA Q F L N | ATAAGTGTTT K C F | CCGAATCCAG R I Q | GGCCAGGACC G Q D P | CCCAGGACAG Q D R | GGTGAAATGG V K W | TCAGAGGCAC S E A Q |
| 3151 1001 | AGTTCTCCTG F S C | TGAACAGCAA E Q Q | GAAGCCCAGC E A Q L | TGGTCACCAT V T I | TGCAAACCCC A N P | TTAGGGCAAG L G Q A | CATTTATCAC F I T |
| 3221 1024 | AGCCAGCCTC A S L | CCCAACGTGA P N V T | CCTTTGACCT F D L | TTGGATTGGC W I G | CTGCATGCCT L H A S | CTCAGAGCCT Q R D | CTTCCAGTGG F Q W |
| 3291 1047 | ATTGAACAAG I E Q E | AACCCCTGCT P L L | CTATACCAAC Y T N | TGGGCACCAG W A P G | GAGAGCCCTC E P S | TGGCCCCAGC G P S | CCTGCTCCCA P A P S |
| 3361 1071 | GTGGCACCAA G T K | GCCGACCAGC P T S | TCCTGCACAC C A V I | TGGGCACCAG L H S | CCCCTCAGCC P S A | CACTTCACTG H F T G | GCCGCTGGGA R W D |
| 3431 1094 | TGATCGGAGC D R S C | TGCACAGAGG T E E | AGACGCCATG T H G | CTTCATCTGC F I C | CAGAAGGCA Q K G T | CAGACCCCTC D P S | GCTAAGCCCA L S P |
| 3501 1117 | TCCCCAGCAG S P A A | CAACACCCCC T P P | TGCCCCCGGC A P G | GCTGAGCTCT A E L S | CCTATCTCAA Y L N | CCACACCTTC H T F | CGGCTGCTGC R L L Q |

FIG. 2E

```
3571 AGAAGCCACT GCGCTGGAAA GATGCTCTCC TGCTGTGTGA GAGCCGAAAT GCCAGCCTGG CACACGTGCC
1141  K  P  L    R  W  K    D  A  L  L    C  E       S  R  N    A  S  L  A    H  V  P

3641 CGATCCCTAC ACACAAGCCT TCCTCACACA GGCTGCACGG GGGCTGCAAA CACCACTGTG GATCGGGCTG
1164  D  P  Y    T  Q  A  F    L  T  Q    A  A  R    G  L  Q  T    P  L  W    I  G  L

3711 GCCAGTGAGG AGGGCTCACG GAGGTATTCC TGGCTCTCAG AGGAGCCTCT GAATTATGTG AGCTGGCAAG
1187  A  S  E  E    G  S  R    R  Y  S    W  L  S  E    E  P  L    N  Y  V    S  W  Q

3781 ATGAGGAGCC CCAGCACTCG GAGGCTGTG CCTACGTGGA TGTGGATGGA GGGCACCCAC CCACGAGCTG
1211  E  E  P    Q  H  S    G  G  C  A    Y  V  D    V  D  G    G  H  P  P    T  S  C

3851 TGATACCAAG CTGCAGGGGG CAGTGTGTGG GGTGAGCAGG GGGCACCCAC CCCGAAGGAT AAACTACCGT
1234  D  T  K    L  Q  G  A    V  C  G    V  S  R    G  H  P  P    R  R  I    N  Y  R

3921 GGCAGCTGTC CTCAGGGCTT GGCTGACTCG CCTTCAGGGA GCATTGCTAT TCTTTCCACA
1257  G  S  C  P    Q  G  L    A  D  S    S  W  I  P    F  R  E    H  C  Y    S  F  H  M

3991 TGGAGGTGCT GTTGGGCCAC AAGGAGGCGC TGCAGCGCTG TCAGAAAGCT GGTGGGACGG TTCTGTCCAT
1281  E  V  L    L  G  H    K  E  A  L    Q  R  C    Q  K  A    G  G  T  V    L  S  I

4061 TCTTGATGAG ATGGAGAATG TGTTTGTCTG GGAGCACCTG CAGACAGCTG AAGCCCAAAG TCGAGGTGCC
1304  L  D  E    M  E  N  V    F  V  W    E  H  L    Q  T  A  E    A  Q  S    R  G  A

4131 TGGTTGGGCA TGAACTTCAA CCCCAAAGGA CCCAAGGGA AGCCCAAGA TCTGGCAAGA CAACACAGCT GTGAACTATT
1327  W  L  G  M    N  F  N    P  K  G    P  K  G    T  L  V    W  Q  D    N  T  A    V  N  Y  S

4201 CTAACTGGGG GCCCCCTGGC CTGGGCCCTA GCATGCTAAG CCACAACAGC TGCTACTGGA TCCAGAGCAG
1351  N  W  G    P  P  G    L  G  P  S    M  L  S    H  N  S    C  Y  W  I    Q  S  S
```

FIG. 2F

```
4271 CAGCGGACTG TGGCGCCCCG GGGCTTGTAC CAACATCACC ATGGGAGTTG TCTGCAAGCT CCCTAGAGTG
1374        S  G  L     W  R  P  G     A  C  T     N  I  T     M  G  V  V     C  K  L     P  R  V

4341 GAAGAGAACA GCTTCTTGCC ATCAGCAGCC CTCCCCGAGA GCCCGGTTGC CCTGGTGGTG GTGCTGACAG
1397  E  E  N  S     F  L  P     S  A  A     L  P  E  S     P  V  A     L  V  V     V  L  T  A

4411 CGGTGCTGCT CCTCCTGGCC TTGATGACGG CAGCCCTCAT CCTCTACCGG CGCCGACAGA GTGCGGAGCG
1421  V  L  L     L  L  A     L  M  T  A     A  L  I     L  Y  R     R  R  Q  S     A  E  R

4481 TGGGTCCTTC GAGGGGGCCC GCTACAGTCG CAGCAGCCAC TCTGGCCCCG CAGAGGCCAC CGAGAAGAAC
1444  G  S  F     E  G  A  R     Y  S  R     S  S  H     S  G  P  A     E  A  T     E  K  N

4551 ATTCTGGTGT CTGACATGGA AATGAACGAA CAGCAAGAAT AGAGCCAAGG GCGTGGTCGG GGTGGAGCCA
1467  I  L  V  S     D  M  E     M  N  E     Q  Q  E  Q

4621 AAGCGGGGGA GGCAGGCAGG CCCAGTTGTC GAGCGGGTAA GGCAGGGGCC CCAGGTCAGC AGGCCCCCAT

4691 CACCCATCAG CCCAGTTGTC GGGAGTACCC AGCCTACCAT AGAGGCTAGG GGGTGCCGGG GGCATAGCTT

4761 GCCATGGGGT GGGAGTACCC AGCCTACCAT AGAGGCTAGG CTGAGACTTG GCAGTGGGTC ATGTTCCCCT

4831 TTCCCTTGGG CCTGGGATCG TGTCACCTGG GAGGCAATA  TGAGAAGGGA

4901 CATGAGCTTA TTCATGTCTT TTCCTCCCCA GATCCCTGAG CCTAAACCTG CTGACCTGCA GCCTAGGATT

4971 CTTTCCTATC TGTAGGCCTG GAAAGCCTGC CCCGTCCCTT GGGGTGGCTC TCTGTCACCT CTCCTACTCG

5041 GCTACATCAG TTCTGTCTCC TCACCCTGCC CTCGTGCCTT TTTTCCACC  CAGTGCCCTCC TTCTGAGCCA
```

FIG. 2G

```
5111  TGGCCCTGGG ACTTGGGTGA TCTCTCTCTC TCTCTCTCTC TCTCTCTTTC
5181  TCTCTGGGTG GGGGTCAGCT GAAGAGGCTG GCCAAGCATC TGTCACTCCT GAATGGACCT
5251  AGGGTATGGC AGGAGGGAGC CTAGGTGGCT CAGGTGTACA AACCAGGGCA CCGGTGTGGT GTGCCTGCTG GTGCCTGCTGGA
5321  GTAGAGATGG AACTTCGGAG AGACACCTTA TCCACTCACA GGGTGTCATC TCCTGCTGGT CAGGGGAGGG
5391  CTCTGTCCTT GAAAGAGTCC CCTGTGGGGA CCAAAATAAG TTCCCTAATG TCTCCGGCTT CTGGCTCTGG
5461  CTTGGAGAGA GGGAAGATGG TTTGGAGGGG GAGGGGCGCT GGTGAGGCTG TAACCTGGGA CAGCACCAGG
5531  TGCTACCATC TGGTGTGGCC TAGGAGACCA ACTCATGGAA CCGCTCAGCA CCTTTTTCCA GAGGAGAGTC
5601  CCAGCCAGGA TGGAGAGTGC CAGTCCCCGT GTCCCAGTGC AGGACGATGT GAACAAAAAC TCAAAGCGGA
5671  CCCTCTATTG TAGTTCTTGA CTCTCGAAAT GTGCTACTAT TGTTTGTCTT TTTTTTTTTT TTTAAAGCCG
5741  GGAAAAGAGA AAAGAATAG CCCCCAAATA AAAACCTTCC AGAGGCTTGA GAAGTCCAAA AAAAAAAAAA
5811  AAAAAAAGTC GACGCGGCCG CGAATTC
```

FIG. 2H signal sequence

| | |
|---|---|
| novel lectin | MVPIRPALA-PWPRHLLRCVLLLG-GLRLGHPADSAAALLEPDVFLIFSQ |
| murine mannose | ----------MRLLLL------LAFISVIPVSVQLLDARQFLIYNE |
| murine PLA2 | MVQWLAMLQLLWLQQLLLGIHQGIAQDLTHIQEPSLEWRDKGIFIHQSE |
| murine DEC205 | --MRTGRVTPGLAAGLLLLR---SFGLVEPSESS---GNDPFTIVHE |

| | |
|---|---|
| novel lectin | GMQGCLEAQGVQVRVTPFCNASLPAQRWKWVSRNRLFNLGATQCLGTGWP |
| murine mannose | DHKRCVDALSAISVQTATCNPEAESQKFRWVSDSQIMSVAFKLCLGV--P |
| murine PLA2 | SLKTCIQA-GKSVLTLENCKQPNEHMLWKWVSDDHLFNVGGSGCLGLN-- |
| murine DEC205 | NTGKCIQPLSDWV-VAQDCS-GTNNMLWKWVSQHRLFHLESQKCLGLD-- | cysteine rich

| | |
|---|---|
| novel lectin | VTNTTVSLGMYECDREALSLRWQCSYTRGPVVPASGGSCKQCIQAWHLER |
| murine mannose | SKTDWASVTLYACDSKSEYQKWECKNDTLFGIKGTELYFNYGNRQEKNIK |
| murine PLA2 | ISALEQPLKLYECDSTLISLRWHC-----DRKMIEGPLQYKVQVKS-DNTV |
| murine DEC205 | ITKATDNLRMFSCDSTVM-LWWKC-----EHHSLYTAAQYRLALKDGYAVA |

FN II

| | |
|---|---|
| novel lectin | GDQTRS--GHWNIY-GSEEDLCARPYYEVYTIQGNSHGKPCTIPFKYDNQ |
| murine mannose | LYKGSGLWSRWKVY-GTTDDLCSRGYEAMYSLLGNANGAVCAFPFKFENK |
| murine PLA2 | VARKQI--HRWIAYTSSGGDICEHPSRDLYTLKGNAHGMPCVFPFQEKGH |
| murine DEC205 | NTNTS---DVWKK-GGSEENLCAQPYHEIYTRDGNSYGRPCEFPFLIGET |

| | |
|---|---|
| novel lectin | WFHGCTSTGREDGHLWCATTQDYGKDERWGFCPIKSND----CETFWDKDQ |
| murine mannose | WYADCTSAGRSDGWLWCGTTTDYDKDKLFGFCPLHFEG----SERLWNKDP |
| murine PLA2 | WHHDCIREGQKEHLLWCATTSRYEEDEKWGFCPDPTSMKVFCDATWQRNG |
| murine DEC205 | WYHDCIHDEDHSG-PWCATTLSYEYDQKWGICLLPESG----CEGNWEKNE |

```
novel lectin       EGRWNDSPCNQSLPSICKKAG-RLSQGAAEEDHDCRKGWTWHSPSCYWLG
murine mannose     DGYWADRACEQPLGYICKMVSQSHAVVPEGADKGCRKGWKRHGFYCYLIG
murine PLA2        DGRWKVKDCKERLFYICKKAG----QVPADEQSGCPAGWERHGRFCYKID
murine DEC205      LGQWKVQSCEKKLRYVCKKKGEITKDAESDKLCPPDEGWKRHGETCYKIY novel lectin       EDQVIYSDARRLCTDHGSQLVTITNRFEQAFVSSLIYNW---E-GEYFWTA
murine mannose     STLSTFTDANHTCTNEKAYLTTVEDRYEQAFLTSLVGLR--P-EKYFWTG
murine PLA2        TVLRSFEEASSGYY-CSPALTITSRFEQAFITSLISSVAEK-DSYFWIA
murine DEC205      EKEAPFGTN----CN-------LTITSRFEQEFLNYMMKNYDKSLRKYFWTG

CRD-3 novel lectin       LQDLNSTGSFRW-LSGDE----VIYTHWNRDQPGYRRGGCVALATGSAMGL
murine mannose     LSDVQNKGTFRW-TVDEQ----VQFTHWNADMPG-IRKAGCVAMKTGVAGGL
murine PLA2        LQDQNNTGEYTW-KTVGQREPVQYTYWNTRQPS-NRGGCVVRGGSSLGR
murine DEC205      LRDPDSRGEYSWAVAQGVKQAVTFSNWNFLEEA-SPGGCVAMSTGKTLGK novel lectin       WEVKNCTSFRARYICRQSLGTPVTPELPGEDPTPSLTGSCPQGWVSDPKL
murine mannose     WDVLSCEE-KAKFVCKHWAEGVTRPPEPTTTPEP----KCPENWGTTSKT
murine PLA2        WEVKDCSDFKAMSLCKTPVKIWEKTELEERWPFH----PCYMDWESATGL
murine DEC205      WEVKNCRSFRALSICKK-VSEPQEEEAAPKPDD----PCPEGWHTFPSS novel lectin       RHCYKVFSSERLQEKKSWIQALGVCRELGAQLLSLASYEEEHFVAHMLNK
murine mannose     SMCFKLYAKGK-HEKKTWFESRDFCKAIGGELASIKSKDEQQVIWRLITS
murine PLA2        ASCFKVFHSEKVLMKRSWREAEAFCEEFGAHLASFAHIEEENFVNELLHS
murine DEC205      LSCYKVFHIERIVRKRNWEEAERFCQALGAHLPSFSRREIKDFVHLLKD
```

| | |
|---|---|
| novel lectin | SNSSGETQPQDLPPSALGGCPSGWNQELNKCFRIQ-GQDPQDRVKWSEAQ |
| murine mannose | HNSSINATAMPTPTTPGGCKEGWHLYKNKCFKI-FGFANEEKKSWQDAR |
| murine PLA2 | VKIW--VIEKEKPPTQPGTCPKGWLYFNYKCFLVTIPKDPRELKTWTGAQ |
| murine DEC205 | YNVS-SLEKYSPDPAAKVQCTEKWIPFEQNKCFL----KVNSGPVTFSQAS |

| | |
|---|---|
| novel lectin | FSCEQQEAQLVTIANPLGQAFITASLPNVTFDLWIGLH--ASQRDFQWIE |
| murine mannose | QACKGLKGNLVSIENAQEQAFVTYHMRDSTFNAWTGLNDINAEHMELWTA |
| murine PLA2 | EFCVAKGGTLVSIKSELEQAFITMNLFGQTTNVWIGLQ--STNHE-KWVN |
| murine DEC205 | GICHSYGGTLPSVLSRGEQDFISLLEMEASLWIGLRWTAYERINRWTD |

CRD-6

| | |
|---|---|
| novel lectin | QEPLLYTNWAPGEPSGPSPAPSGT--KPTS--CAVILHSPSAHFTGRWDD |
| murine mannose | GQGVHYTNWGKGYPGGRRSSLSYE---DA-DCVVIGGNSRE-AGTWMD |
| murine PLA2 | GKPLVYSNWSPSDIINIPSYNTTEFQKHIP-LCALMSSNENFHFTGKWYF |
| murine DEC205 | NRELTYSNFHPLLVGRRLSIPTNFFDDESHFHCALILNLKKSPLTGTWNF |

| | |
|---|---|
| novel lectin | RSCTEETHGFICQKGTDPSLSPSPAATPPAPGAELSYLNHTFRLLQKPLR |
| murine mannose | DTC-DSKQGYICQTQTDPSLPVSPTTPK--DGFVTYGKSSYSLMKLKLP |
| murine DEC205 | DDCGKEGYGFVCEKMQDTLEHHVNVSDTSAIPSTLEYGNRTYKIIRGNMT |
| murine PLA2 | TSCSERHSLSLCQKYSETEDGQPWENTSK---TVKYLNNLYKIISKPLT |

CRD-7

| | |
|---|---|
| novel lectin | WKDALLCESRNASLAHVPDDPYTQAFLTQAARGLQTPLWIGLASEEGSRR |
| murine mannose | WHEAGTYCKDHTSLLASILDPYSNAFAWMKMHPFNVPIWIALNSLTNNE |
| murine PLA2 | WYAAGKSCRMHRAELASIPDAFHQAFLTVLLSRLGHTHWIGLSTTDNGQT |
| murine DEC205 | WHGALKECMKEKMRLVSITDPYQQAFLAVQATLRNSSFWIGLSSQDDELN |

```
novel lectin      MGVVCKL-PRVEENSFLPS------------------AALPESPVALVVVLTAVLL
murine mannose    KGFICKMPKIIDPVTTHSSITTKADQRKMDPQPKGSSKAAGVVTVVLLIV
murine PLA2       KGFICKMEAGIPAVTAQEE-----------------KGLSHSIVPVTVTLTLIIA
murine DEC205     ETLHFYQHSISACKIEMVD--------------YEDKHNYTGIALFAVLCL
                                                              ₍₂₇₃ AA DEC250

TMD
novel lectin      LLALMTAALILYRRR--QSAERGSFEGARYSRSSHSGPAEATEKNILVSD
murine mannose    IGAGVAAYFFYKKRHALHIPQEATFENTLYFNS-NLSPGT-SDTKDLMGN
murine PLA2       LGIFMLCFWIYKQKS--DIFQRLTGSRGSYPTLNFSTAH-LEENILISD
murine DEC205     LGLISLAIWFLLQRS--HI-RWTGFSSVRYEHGTN------EDEVMLPS novel lectin      MEMNEQQE-----
murine mannose    IEQNEHAII----
murine PLA2       LEKNTNDEEVRDAPATESKRGHKGRPICISP
murine DEC205     FHD----------
```

FIG. 3G

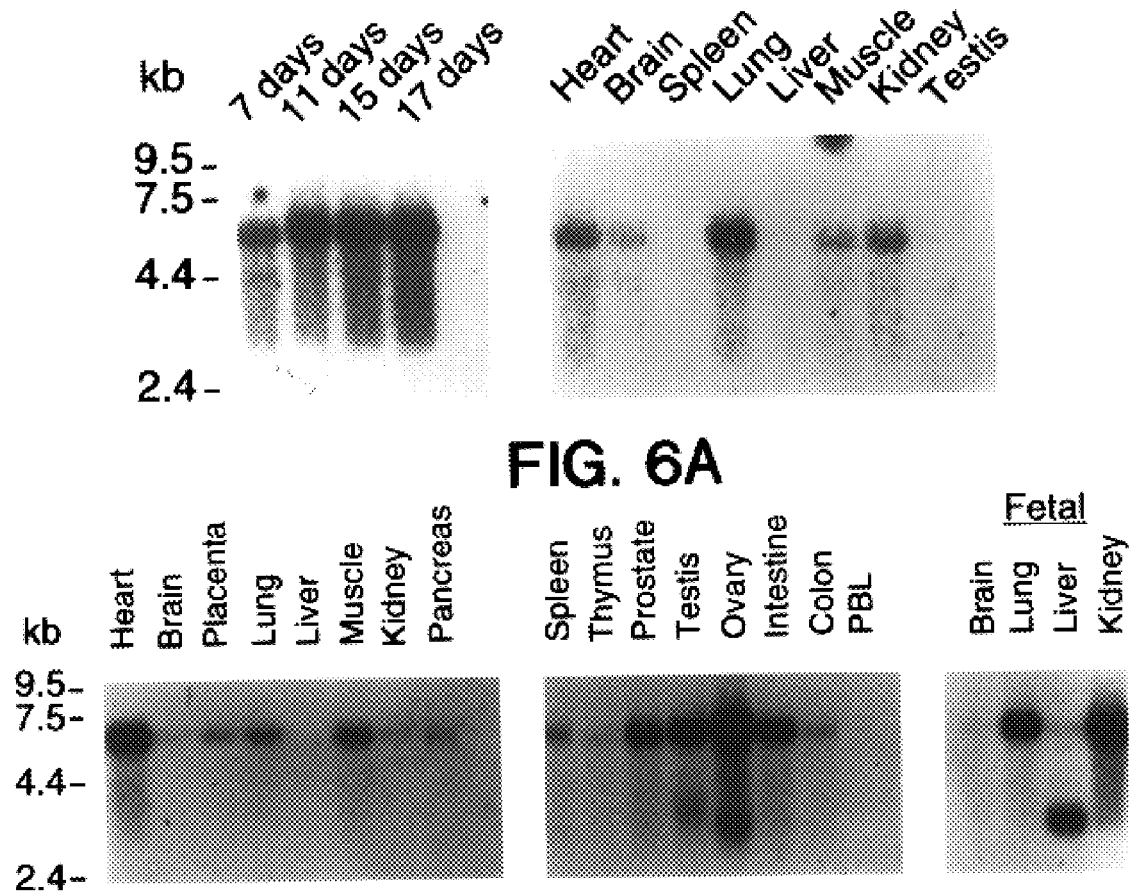
FIG. 6A
FIG. 6B
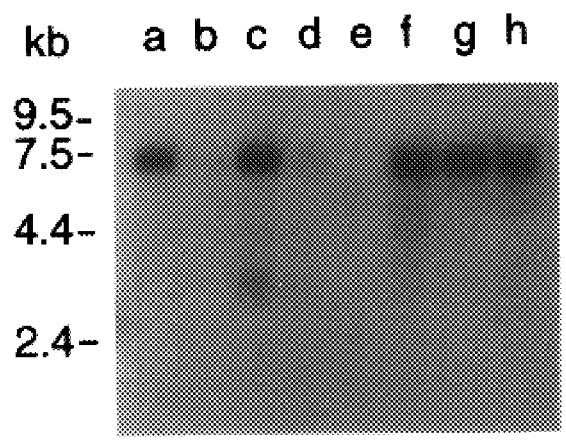
FIG. 6C

MVPIRPALAPWPRHLLRCVLLLGGLRLGHPADSAAALLEPDVFLIFSQGMQGCLEAQGVQ
VRVTPVCNASLPAQRWKWVSRNRLFNLGATQCLGTGWPVTNTTVSLGMYECDREALSLRM
AVSYTRGPVVPASGGSCKQCIQAWHLERGDQTRSGHWNIYGSEEDLCARPYYEVYTIQGN
SHGKPCTIPFKYDNQWFHGCTSTGREDGHLWCATTQDYGKDERWGFCPIKSNDCETFWDK
DQLTDSCYQFNEQSTLSWREAWASCEQQGADLLSITEIHEQTYINGLLTGYSSTLWIGLN
DLDTSGGWQWSDNSPLKYLNWESDQPDNPGEENCGVIRTESSGGWQNHDCSIALPYVCKK
KPNATVEPIQPDRWTNVKVECDPSWQPFQGHCYRLQAEKRSWQESKRACLRGGDLLSIH
SMAELEFITKQIKQEVEELWIGLNDLKLQMNFEWSDGSLVSFTHWHPFEPNNFRDSLEDC
VTIWGPEGRWNDSPCNQSLPSICKKAGRLSQGAAEEDHDCRKGWTWHSPSCYWLGEDQVI
YSDARRLCTDHGSQLVTITNRFEQAFVSSLIYNWEGEYFWTALQDLNSTGSFRWLSGDEV
IYTHWNRDQPGYRRGGCVALATGSAMGLWEVKNCTSFRARYICRQSLGTPVTPELPGPDP
TPSLTGSCPQGWVSDPKLRHCYKVFSSERLQEKKSWIQALGVCRELGAQLLSLASYEEEH
FVAHMLNKIFGESEPESHEQHWFWIGLNRRDPREGHSWRWSDGLGFSYHNFARSRHDDDD
IRGCAVLDLASLQWVPMQCQTQLDWICKIPRGVDVREPDIGRQRLEWVRFQEAEYKFFE
HHSSWAQAQRICTWFQADLTSVHSQAELGFLGQNLQKLSSDQEQHWWIGLHTLESDGRFR
WTDGSIINFISWAPGKPRPIGKDKKCVYMTARQEDWGDQRCHTALPYICKRSNSSGETQP
QDLPPSALGGCPSGWNQFLNKCFRIQGQDPQDRVKWSEAQFSCEQQEAQLVTIANPLEQA
FITASLPNVTFDLWIGLHASQRDFQWIEQEPLLYTNWAPGEPSGPSPAPSGTKPTSCAVI
LHSPSAHFTGRWDDRSCTEETHGFICQKGTDPSLSPSPAATPPAPGAELSYLNHTFRLLQ
KPLRWKDALLCESRNASLAHVPDPYTQAFLTQAARGLQTPLWIGLASEEGSRRYSWLSE
EPLNYVSWQDEEPQHSGGCAYVDVDGTWRTTSCDTKLQGAVCGVSRGPPPRRINYRGSCP
QGLADSSWIPFREHCYSFHMEVLLGHKEALQRCQKAGGTVLSILDEMENVFVWEHLQTAE
AQSRGAWLGMNFNPKGGTLVWQDNTAVNYSNWGPPGLGPSMLSHNSCYWIQSSSGLWRPG
ACTNITMGVVCKLPRVEENSFLPSAALPESPVALVVLTAVLLLLALMTAALILYRRQS
AERGSFEGARYSRSSHSGPAEATEKNILVSDMEMNEQQE

FIG. 9

TYPE C LECTINS

This is a non-provisional continuation application filed under 37 C.F.R. 1.53 (b)(1), claiming priority under 35 U.S.C. 119 (e) to provisional application Ser. No. 60/052, 524, converted from non-provisional application Ser. No. 08/637,021 filed Apr. 24, 1996.

FIELD OF THE INVENTION

The present invention concerns novel type C lectins. More particularly, the invention relates to new members of the endocytic type C lectin family and functional derivatives of such novel polypeptides.

BACKGROUND OF THE INVENTION

The recognition of carbohydrates by lectins has been found to play an important role in various aspects of eukaryotic physiology. A number of different animal and plant lectin families exist, but it is the calcium dependent, or type C, lectins that have recently garnered the most attention. For example, the recognition of carbohydrate residues on either endothelial cells or leukocytes by the selectin family of calcium dependent lectins has been found to be of profound importance to the trafficking of leukocytes to inflammatory sites. Lasky, L., *Ann. Rev. Biochem.*, 64 113–139 (1995). The biophysical analysis of these adhesive interactions has suggested that lectin-carbohydrate binding evolved in this case to allow for the adhesion between leukocytes and the endothelium under the high shear conditions of the vasculature. Alon et al., *Nature* (1995) in press. Thus, the rapid on rates of carbohydrate recognition by such lectins allows for a hasty acquisition of ligand, a necessity under the high shear of the vascular flow. The physiological use of type C lectins in this case is also supported by the relatively low affinities of these interactions, a requirement for the leukocyte rolling phenomenon that has been observed to occur at sites of acute inflammation. The crystal structures of the mannose binding protein (Weis et al., *Science* 254, 1608–1615 [1991]; Weis et al., *Nature* 360 127–134 [1992]) and E-selectin (Graves et al., *Nature* 367 (6463), 532–538 [1994]), together with various mutagenesis analyses (Erbe et al., *J. Cell. Biol.* 119(1), 215–227 [1992]; Drickamer, *Nature* 360, 183–186 [1992]; Iobst et al., *J. Biol. Chem.* 169(22), 15505–15511 [1994]; Kogan et al., *J. Biol. Chem.* 270(23), 14047–14055 [1995]), is consistent with the supposition that the type C lectins are, in general, involved with the rapid recognition of clustered carbohydrates. Together, these data suggest that type C lectins perform a number of critical physiological phenomena through the rapid, relatively low affinity recognition of carbohydrates.

While a number of different type C lectin families are known, a particularly unusual group is that represented by the macrophage mannose (Taylor et al., *J. Biol. Chem.* 265(21), 12156–62 [1990]; Harris et al., *Blood* 80(9), 2363–73 [1992]), phospholipase A2 (Ishizaki et al., *J. Biol. Chem.* 269(8), 5897–904 [1994]; Lambeau et al., *J. Biol. Chem.* 269(3), 1575–8 [1994]; Higashino et al., *Eur. J. Biochem.* 225(1), 375–82 [1994]) and DEC 205 (Jiang et al., *Nature* 375(6527), 151–5 [1995]) receptors. While most of the members of the type C lectin group contain only a single carbohydrate binding domain, these three receptors contain either 8 (macrophage mannose and phospholipase A2 receptors) or 10 (DEC 205 receptor) lectin domains, and it is likely that these domains cooperate with each other to enhance ligand avidity (Taylor et al., *J. Biol. Chem.* 267(3), 1719–20 [1992]; Taylor et al., *J. Biol. Chem.* 268(1), 399–404 [1993]). All three of these molecules appear to be type 1 transmembrane proteins, and they all appear to mediate various endocytic phenomena. Accordingly, this family will hereafter be referred to as the endocytic type C lectin family (Harris et al, supra; Jiang et al., supra; Zvaritch et al., *J. Biol. Chem.* 271(1), 250–7 [1996]). The endocytic mechanism is particularly important in the case of the macrophage mannose receptor, expressed predominately on macrophages and liver endothelium (Harris et al., supra), and the DEC 205 receptor (Jiang et al. supra), expressed specifically on dendritic and thymic epithelial cells. Thus, both of these receptors appear to mediate the endocytosis of large particulate (ie. pathogens such as yeast) (the macrophage mannose receptor) or highly glycosylated molecular (the DEC 205 receptor) complexes. In both cases, the endocytosis of glycosylated complexes by these receptors is involved with the transport of either particles or glycoproteins to the endosomal pathway where they are degraded and, in the case of the DEC 205 receptor, efficiently presented to cells of the immune system by the dendritic or thymic epithelial cells (Jiang et al, supra). It therefore seems likely that both of these receptors are involved with the presentation of highly glycosylated structures to immune cells to allow for efficient responses against pathogenic organisms. Interestingly, the phospholipase A2 receptor is also likely to be involved with the endocytic uptake of extracellular proteins, although in this case it appears to be an endogenous protein, ie. one or more phospholipases (Ishizaki et al., supra; Lambeau et al., supra; Higashino et al., supra; Zvaritch et al., supra). The exact biological function of this receptor, other than as a high affinity mediator of phospholipase binding, is unknown, and its tissue expression pattern appears to be far broader than that of the other two receptors in this family (Higishino et al., supra). In addition, it is not clear that the binding of phospholipase to this receptor is mediated by protein-carbohydrate interactions, although this receptor is clearly capable of binding glycosylated proteins (Lambeau et al., supra). In summary, all three of the known members of this family of type C lectins appear to be involved with the binding and uptake of either large particulate or molecular complexes into the endocytic pathway of the cell, and in the case of both the macrophage mannose and DEC 205 receptors, these interactions appear to be via protein-carbohydrate recognition.

SUMMARY OF THE INVENTION

The present invention is based on the identification, recombinant production and characterization of a novel member of the family of endocytic type C lectins. More specifically, the invention concerns a novel polypeptide comprising a region which shows a distant (~23%) homology to a region of the E-selectin lectin domain. In analyzing the homologous sequence motif, we have surprisingly found that, despite the low degree of homology, the residues that were identical with residues in the E-selectin lectin domain were included in the subset of amino acids that are conserved in the vast majority of type C lectins. Based upon this observation and further findings which will be described hereinafter, the novel protein has been identified as a new member of the family of endocytic type C lectins. The novel protein contains domains that are distantly related, but similar in overall structure, to those found in the other members of this lectin family. In addition, it appears to be expressed specifically in some highly endothelialized regions of the embryo and adult as well as by actively growing and differentiating chondrocytes in the embryo.

These data suggest that this lectin represents a novel member of the endocytic lectin family that may be involved with the endocytosis of glycosylated complexes by the endothelium as well as by chondrocytes during cartilage formation.

In one aspect, the present invention concerns novel isolated mammalian type C lectins closely related to the macrophage mannose receptor, the phospholipase A2 receptor and the DEC 205 receptor, all members of the family of type C lectins containing multiple lectin domains which mediate endocytosis, and functional derivatives of the novel type C lectins. The native polypeptides within the scope of the present invention are characterized by containing a signal sequence, a cysteine rich domain, a fibronectin type II domain, 8 type C lectin domains, a transmembrane domain and a short cytoplasmic domain. The present invention specifically includes the soluble forms of the new receptor molecules, which are devoid of an active transmembrane domain and optionally of all or part of the cytoplasmic domain.

In a particular embodiment, the invention concerns isolated type C lectins selected from the group consisting of (1) a polypeptide comprising the amino acid sequence shown in FIG. 2 (SEQ. ID. NO: 2);

(2) a polypeptide comprising the amino acid sequence shown in FIG. 9 (SEQ. ID. NO: 4);

(3) a further mammalian homologue of polypeptide (1) or (2);

(4) a soluble form of any of the polypeptides (1)–(3) devoid of an active transmembrane domain; and (5) a derivative of any of the polypeptides (1)–(3), retaining the qualitative carbohydrate recognition properties of a polypeptide (1), (2) or (3).

The native type C lectins of the present invention are glycoproteins. The present invention encompasses variant molecules unaccompanied by native glycosylation or having a variant glycosylation pattern.

In a further embodiment, the invention concerns an antagonist of a novel type C lectin of the present invention.

The invention further concerns a nucleic acid molecule encoding a novel type C lectin of the present invention, vectors containing such nucleic acid, and host cells transformed with the vectors. The nucleic acid preferably encodes at least the fibronectin type II domain and the first three lectin domains of a native or variant type C lectin of the present invention. The invention further includes nucleic acid hybridizing under stringent condition to the complement of a nucleic acid encoding a native type C lectin of the present invention, and encoding a protein retaining the qualitative carbohydrate binding properties of a native type C lectin herein.

In another aspect, the invention concerns a process for producing a type C lectin as hereinabove defined, which comprises transforming a host cell with nucleic acid encoding the desired type C lectin, culturing the transformed host cell and recovering the type C lectin produced from the host cell culture.

In a further aspect, the invention concerns an antibody capable of specific binding to a type C lectin of the present invention, and to a hybridoma cell line producing such antibody.

In a still further aspect, the invention concerns an immunoadhesin comprising a novel type C lectin sequence as hereinabove described fused to an immunoglobulin sequence. The type C lectin sequence is preferably a transmembrane-domain deleted form of a native or variant polypeptide fused to an immunoglobulin constant domain sequence, and comprises at least the fibronectin type II domain and a carbohydrate recognition (lectin) domain of a native type C lectin of the present invention. In another preferred embodiment, the type C lectin sequence present in the immunoadhesin shows at least about 80% sequence homology with the fibronectin type II domain and/or with at least one of the first three carbohydrate recognition domains of a native type C lectin of the present invention. The immunoglobulin constant domain sequence preferably is that of an IgG-1, IgG-2 or IgG-3 molecule.

The invention further concerns pharmaceutical compositions comprising a type C lectin as hereinabove defined in admixture with a pharmaceutically acceptable carrier.

BRIEF DESCRIPTION OF THE DRAWINGS

FIG. 1. Sequence homology between the E-selectin lectin domain and an EST. Shown is the homologous sequence (T11885) (SEQ. ID. NO: 9) derived from a search of the expressed sequence tag (EST) database with the E-selectin lectin domain (SEQ. ID. NO: 8). The region of homology was found within amino acids 10–77 of the E-selectin lectin domain.

FIGS. 2A–2H. The DNA and derived protein sequence of the cDNA encoding the E-selectin homologous murine sequence. Illustrated is the entire DNA sequence (SEQ. ID. NO: 1) and derived protein sequence (SEQ. ID. NO: 2) of the murine cDNA clones and RACE products derived using the T11885 DNA sequence as a probe. The region homologous to the original EST stretches from amino acids 995 to 1,061.

FIGS. 3A–3G. Protein homologies between the novel type C lectin (SEQ. ID. NO: 2), the macrophage mannose receptor (SEQ. ID. NO: 5), the phospholipase A2 receptor (SEQ. ID. NO: 7) and the DEC 205 receptor (SEQ. ID. NO: 6). Illustrated are the conserved residues in the three members of the endocytic type C lectin family (boxed). Overlined are shown the signal sequence, cysteine rich, fibronectin type II, type C lectin, transmembrane and cytoplasmic domains. The ninth and tenth type C lectin domains of the DEC 205 receptor were deleted to allow for a clearer alignment.

FIGS. 5A–5C. Genomic blot probed with the novel receptor cDNA and the genomic structure of the gene encoding the novel receptor. A. A "zoo blot" containing genomic DNAs isolated from various organisms and digested with EcoR1 was probed with the original EST fragment isolated by PCR from the heart library. B. The top of the figure illustrates the domain structure of the novel type C lectin and the approximate sites determined by dot blotting and pcr analysis for each intron (arrowheads). Below is shown the genomic locus with each exon defined as a small box.

FIGS. 6A–6C. Northern blot analysis of human and murine tissues and cell lines for expression of the transcript encoding the novel type C lectin. A. A commercial northern blot containing either whole murine fetal RNA (left panel) or RNA derived from adult murine tissues was probed with the original EST derived fragment isolated from the murine heart cDNA library. B. A commercial northern blot containing RNA isolated from various adult or fetal human tissues was probed with the original EST derived from the human heart cDNA library. C. A commercial blot containing RNA isolated from: a. promyelocytic leukemia-HL-60, b. Hela cell-S3, c. chronic myelogenous leukemia-K-562, d. lymphoblastic leukemia-MOLT-4, e. Burkitt's lymphoma-Raji, f. colorectal adenocarcinoma-SW480, g. lung carcinoma-A549 and h. melanoma-G361 human tumor cell lines was probed with the original EST derived from the human heart cDNA library.

FIG. 9. The DNA and derived protein sequences of the novel human type C lectin (SEQ. ID. NOS: 3 and 4).

DETAILED DESCRIPTION OF THE INVENTION

A. Definitions

The phrases "novel type C lectin" and "novel endocytic type C lectin" are used interchangeably and refer to new native members of the family of endocytic type C lectins, which are expressed specifically in some highly endothelialized regions of the embryo and adults, and in actively growing and differentiating chondrocytes in the embryo, and to functional derivatives of such native polypeptides.

Figure 3B:
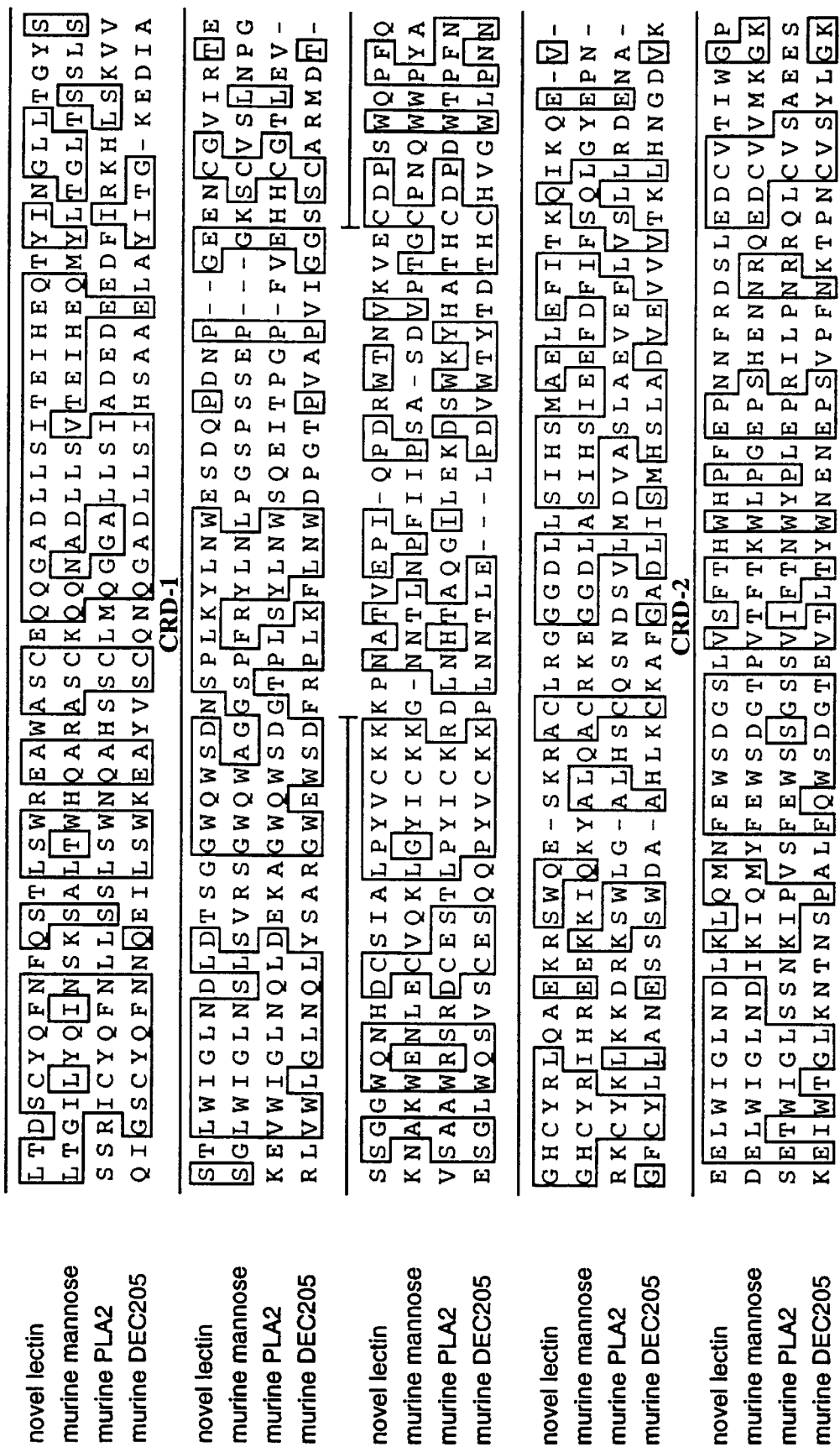
Figure 3D:
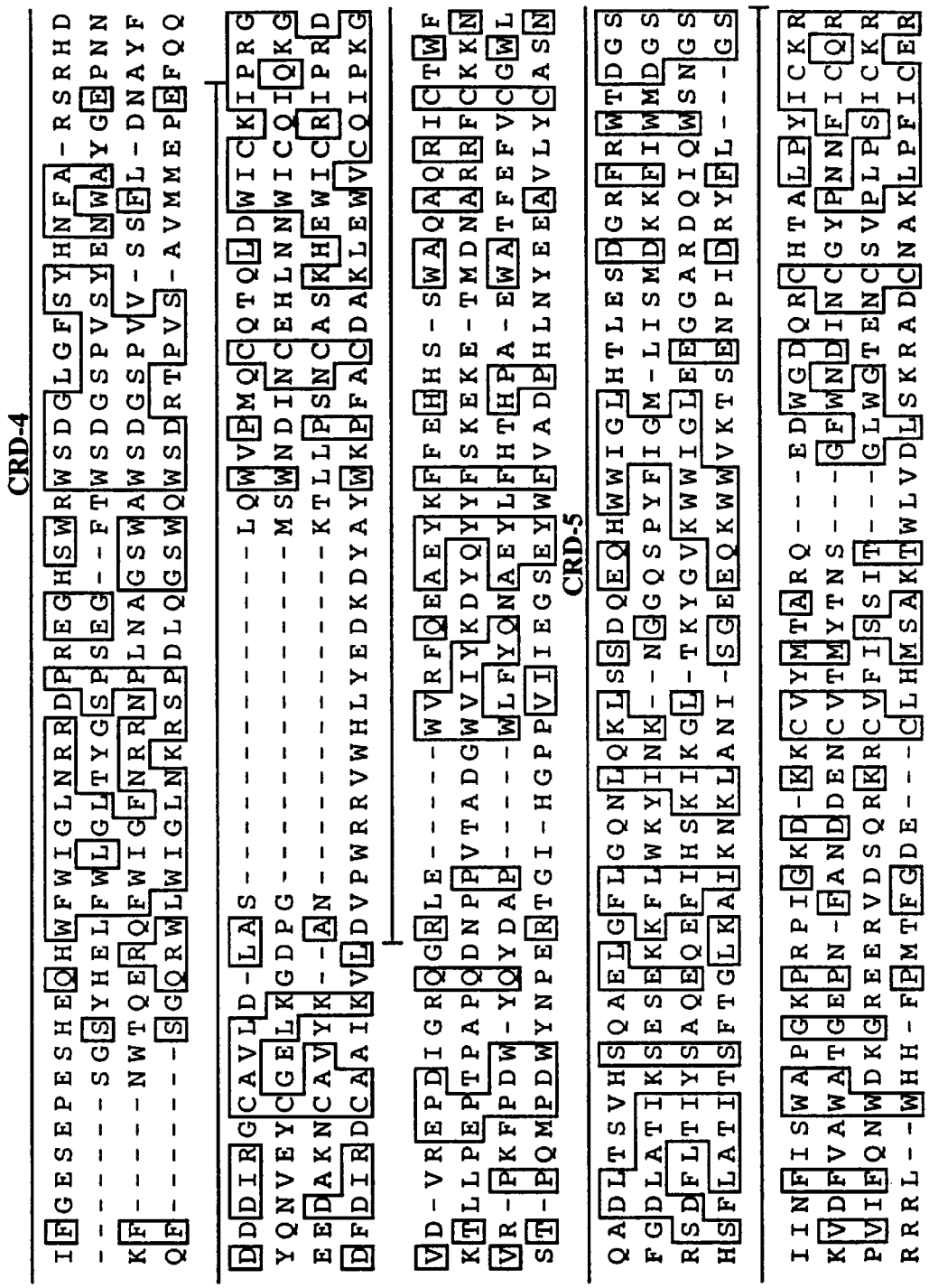
Figure 3F:
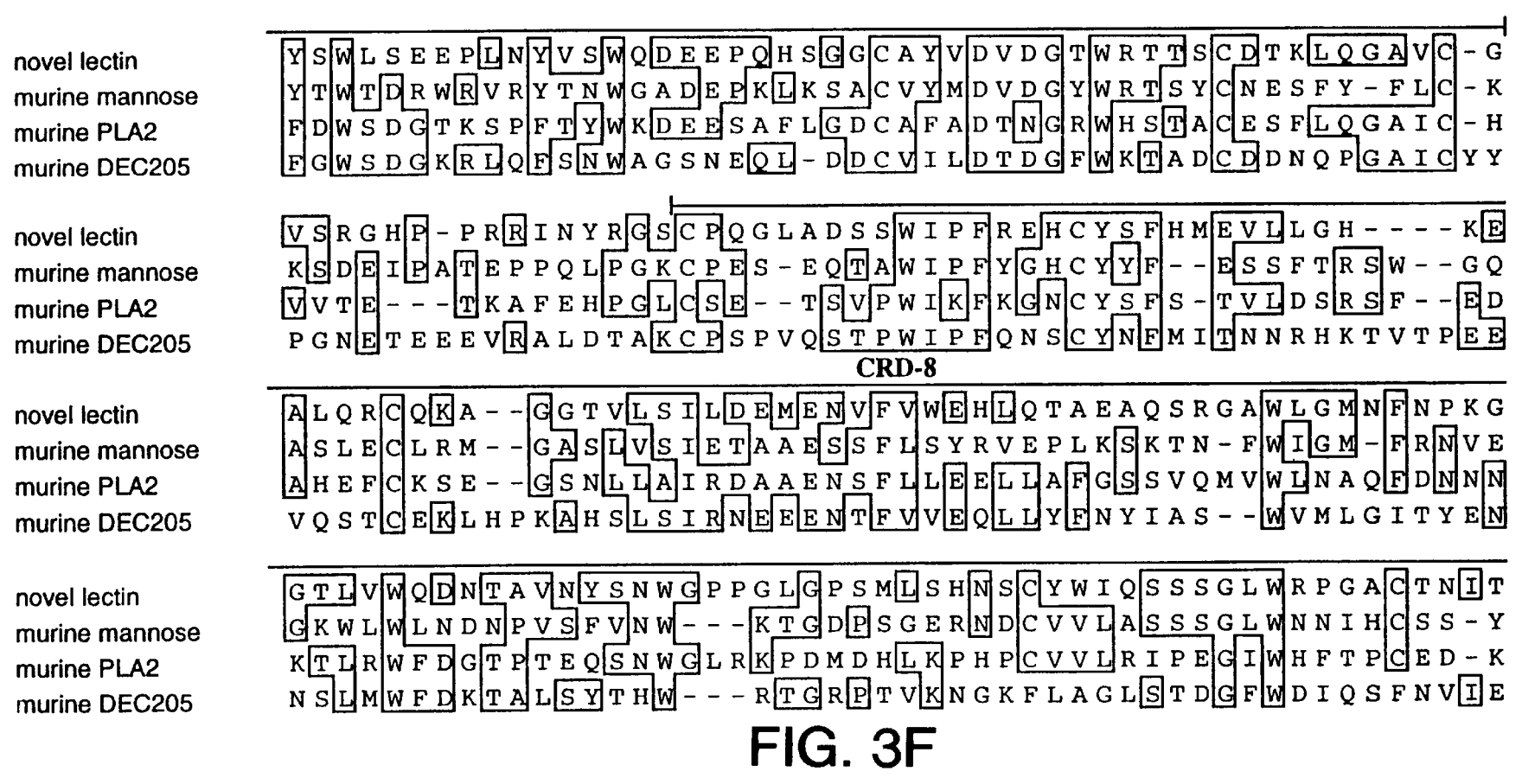

The terms "native (novel) endocytic type C lectin" and "native (novel) type C lectin" in this context refer to novel naturally occurring endocytic type C lectin receptors, comprising a cysteine rich domain, a fibronectin type II domain, multiple type C lectin domains, a transmembrane domain and a cytoplasmic domain, with or without a native signal sequence, and naturally occurring soluble forms of such type C lectin receptors, with or without the initiating methionine, whether purified from native source, synthesized, produced by recombinant DNA technology or by any combination of these and/or other methods. The native type C lectins of the present invention specifically include the murine type C lectin, the amino acid sequence of which is shown in FIGS. 2A–2H (SEQ. ID. NO: 2), and the human type C lectin having the amino acid sequence shown in FIG. 9 (SEQ. ID. NO: 4), and further mammalian homologues of these native receptors. The novel native murine and human type C lectins of the present invention are about 1480 amino acids in length, and comprise a signal sequence (amino acids 1–36), a cysteine-rich domain (from about amino acid position 37 to about amino acid position 174), a fibronectin type II domain (from about amino acid position 175 to about amino acid positions 229), eight carbohydrate recognition (lectin) domains (CRDs) (CRD1: about aa 234–360; CRD2: about aa 381–507; CDR3: about aa 520–645; CRD4: about aa 667–809; CRD5: about aa 824–951; CRD6: about aa 970–1108; CRD7: about aa 1110–1243; CRD8: about aa 1259–1393); a transmembrane domain (from about amino acid position 1410 to about amino acid position 1434); and a cytoplasmic domain, extending to the C-terminus of the molecule. The boundaries of these domain are indicated in FIG. 3 for the novel murine type C lectin sequence.

The terms "soluble form", "soluble receptor", "soluble type C lectin", "soluble endocytic type C lectin", and grammatical variants thereof, refer to variants of the native or variant type C lectins of the present invention which are devoid of a functional transmembrane domain. In the soluble receptors the transmembrane domain may be deleted, truncated or otherwise inactivated such that they are not capable of cell membrane anchorage. If desired, such soluble forms of the type C lectins of the present invention might additionally have their cytoplasmic domains fully or partially deleted or otherwise inactivated.

Figure 4:
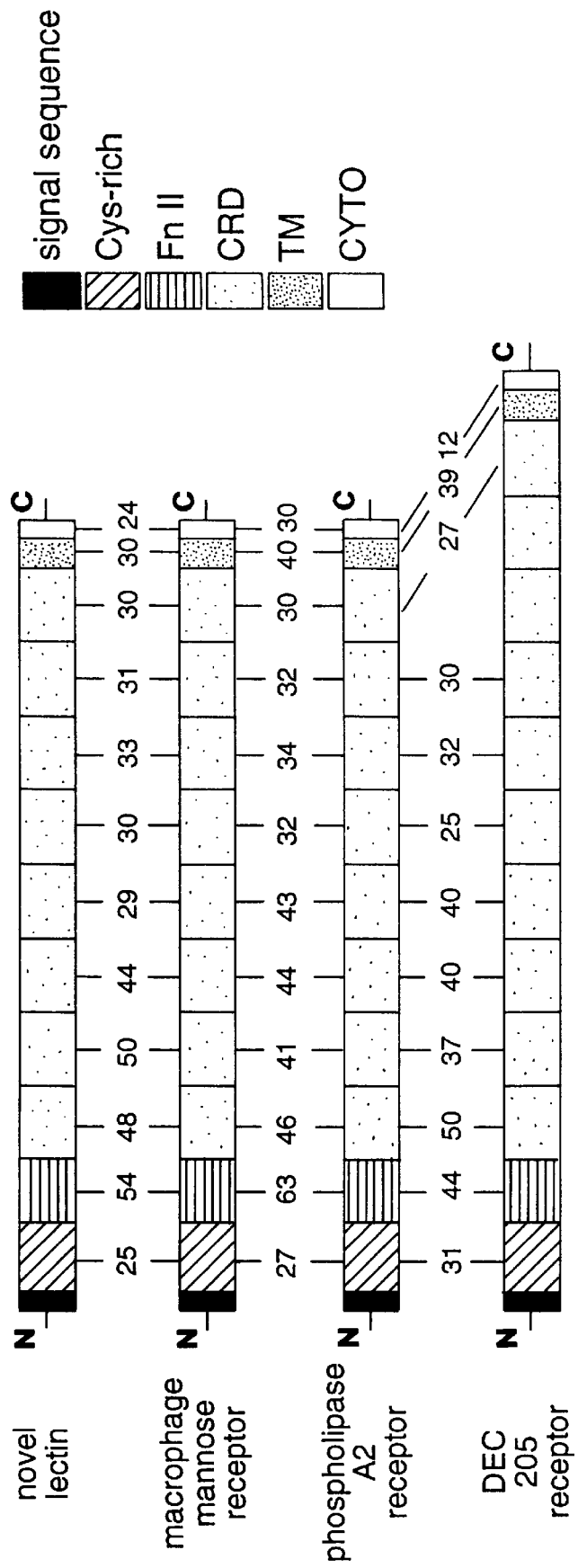
FIG. 4. Domain homologies and relative percent conservation between the novel lectin, the macrophage mannose receptor, the phospholipase A2 receptor and the DEC 205 receptor. Illustrated are the various domains and the percent conservation between these domains in the novel type C lectin and the other three members of the endocytic type C lectin family. The domains are as follows: Cys-rich: cysteine rich, Fn II: fibronectin type 2, CRD: carbohydrate recognition domain (type C lectin), TM: transmembrane, CYTO: cytoplasmic.

A "functional derivative" of a polypeptide is a compound having a qualitative biological activity in common with the native polypeptide. Thus, a functional derivative of a native novel type C lectin of the present invention is a compound that has a qualitative biological activity in common with such native lectin. "Functional derivatives" include, but are not limited to, fragments of native polypeptides from any animal species (including humans), derivatives of native (human and non-human) polypeptides and their fragments, and peptide and non-peptide analogs of native polypeptides, provided that they have a biological activity in common with a respective native polypeptide. "Fragments" comprise regions within the sequence of a mature native polypeptide. The term "derivative" is used to define amino acid sequence and glycosylation variants, and covalent modifications of a native polypeptide. "Non-peptide analogs" are organic compounds which display substantially the same surface as peptide analogs of the native polypeptides. Thus, the non-peptide analogs of the native novel type C lectins of the present invention are organic compounds which display substantially the same surface as peptide analogs of the native type C lectins. Such compounds interact with other molecules in a similar fashion as the peptide analogs, and mimic a biological activity of a native type C lectin of the present invention. Preferably, amino acid sequence variants of the present invention retain at least one domain or a native type C lectin, or have at least about 60% amino acid sequence identity, more preferably at least about 70% amino acid sequence identity, even more preferably at least about 80% amino acid sequence identity, most preferably at least about 90% amino acid sequence identity with a domain of a native type C lectin of the present invention. The amino acid sequence variants preferably show the highest degree of amino acid sequence homology with the fibronectin type II or the lectin-like domain(s), preferably the first three lectin-like (carbohydrate-binding) domains of native type C lectins of the present invention. These are the domains which show the highest percentage amino acid conservation between the novel type C lectins of the present invention and other members of the endocytic type C lectin family (FIG. 4).

The terms "covalent modification" and "covalent derivatives" are used interchangeably and include, but are not limited to, modifications of a native polypeptide or a fragment thereof with an organic proteinaceous or non-proteinaceous derivatizing agent, fusions to heterologous polypeptide sequences, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)]. Covalent derivatives/modifications specifically include fusion proteins comprising native type C lectin sequences of the present invention and their amino acid sequence variants, such as immunoadhesins, and N-terminal fusions to heterologous signal sequences.

The term "biological activity" in the context of the present invention is defined as the possession of at least one adhesive, regulatory or effector function qualitatively in common with a native polypeptide. Preferred functional derivatives within the scope of the present invention are unified by retaining the qualitative carbohydrate recognition properties of a native endocytic type C lectin of the present invention.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

The term "agonist" is used to refer to peptide and non-peptide analogs of the native type C lectins of the present invention and to antibodies specifically binding such native type C lectins provided that they retain at least one biological activity of a native type C lectin. Preferably, the agonists of the present invention retain the qualitative carbohydrate recognition properties of the native type C lectin polypeptides.

The term "antagonist" is used to refer to a molecule inhibiting a biological activity of a native type C lectin of the present invention. Preferably, the antagonists herein inhibit the carbohydrate-binding of a native type C lectin of the present invention. Preferred antagonists essentially completely block the binding of a native type C lectin to a carbohydrate structure to which it otherwise binds.

Ordinarily, the terms "amino acid" and "amino acids" refer to all naturally occurring L-α-amino acids. In some embodiments, however, D-amino acids may be present in the polypeptides or peptides of the present invention in order to facilitate conformational restriction. For example, in order to facilitate disulfide bond formation and stability, a D amino acid cysteine may be provided at one or both termini of a peptide functional derivative or peptide antagonist of the native type C lectins of the present invention. The amino acids are identified by either the single-letter or three-letter designations:

| | | | | | |
|---|---|---|---|---|---|
| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed.

"Antibodies (Abs)" and "immunoglobulins (Igs)" are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651–663 [1985]; Novotny and Haber, *Proc. Natl. Acad. Sci. USA* 82, 4592–4596 [1985]).

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Natl. Acad. Sci. USA* 81, 6851–6855 [1984]).

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 [1986]; Reichmann et al., *Nature* 332, 323–329 [1988]; EP-B-239 400 published Sep. 30, 1987; Presta, *Curr. Op. Struct. Biol.* 2 593–596 [1992]; and EP-B-451 216 published Jan. 24, 1996).

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector", "expression vector" and "vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published May 4, 1988, or via deoxynucleoside H-phosphanate intermediates as described by Froehler et al., *Nucl. Acids Res.* 14, 5399 (1986). They are then purified on polyacrylamide gels.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/ 0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC and 0.1% SDS. Yet another example is hybridization using a buffer of 10% dextran sulfate, 2× SSC (sodium chloride/sodium citrate) and 50% formamide at 55° C., followed by a high-stringency wash consisting of 0.1× SSC containing EDTA at 55° C.

"Immunoadhesins" or "type C lectin—immunoglobulin chimeras" are chimeric antibody-like molecules that combine the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig-" or "Fc-fusion protein", or "receptor-globulin."

B. Production of the novel type C lectins by recombinant DNA technology

1. Identification and isolation of nucleic acid encoding the novel type C lectins The native endocytic type C lectins of the present invention may be isolated from cDNA or genomic libraries. For example, a suitable cDNA library can be constructed by obtaining polyadenylated mRNA from cells known to express the desired type C lectin, and using the mRNA as a template to synthesize double stranded cDNA. Suitable sources of the mRNA are highly endothelialized regions of embryonic and adult mammalian tissues, and differentiating chondrocytes in the embryo. mRNA encoding native type C lectins of the present invention is expressed, for example, in human fetal lung, kidney, and liver tissues; adult murine heart, lung, kidney, brain, and muscle tissues; adult human heart, prostate, testis, ovary, intestine, brain, placenta, lung, kidney, pancrease, spleen, thymus and colon tissues. The gene encoding the novel type C lectins of the present invention can also be obtained from a genomic library, such as a human genomic cosmid library, or a mouse-derived embryonic cell (ES) genomic library.

Libraries, either cDNA or genomic, are then screened with probes designed to identify the gene of interest or the protein encoded by it. For cDNA expression libraries, suitable probes include monoclonal and polyclonal antibodies that recognize and specifically bind to a type C lectin receptor. For cDNA libraries, suitable probes include carefully selected oligonucleotide probes (usually of about 20–80 bases in length) that encode known or suspected portions of a type C lectin polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual,* New York, Cold Spring Harbor Laboratory Press, 1989.

If DNA encoding an enzyme of the present invention is isolated by using carefully selected oligonucleotide sequences to screen cDNA libraries from various tissues, the oligonucleotide sequences selected as probes should be sufficient in length and sufficiently unambiguous that false positives are minimized. The actual nucleotide sequence(s) is/are usually designed based on regions which have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding the novel type C lectins can also be identified and isolated by other known techniques of recombinant DNA technology, such as by direct expression cloning, or by using the polymerase chain reaction (PCR) as described in U.S. Pat. No. 4,683,195, issued Jul. 28, 1987, in section 14 of Sambrook et al., supra, or in Chapter 15 of *Current Protocols in Molecular Biology,* Ausubel et al. eds., Greene Publishing Associates and Wiley-Interscience 1991. The use of the PCR technique to amplify a human heart and a mouse heart cDNA library is described in the examples.

Once cDNA encoding a new native endocytic type C lectin from one species has been isolated, cDNAs from other species can also be obtained by cross-species hybridization. According to this approach, human or other mammalian cDNA or genomic libraries are probed by labeled oligo-nucleotide sequences selected from known type C lectin sequences (such as murine or human sequences) in accord with known criteria, among which is that the sequence should be sufficient in length and sufficiently unambiguous that false positives are minimized. Typically, a $^{32}P$-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. Hybridization is preferably performed under "stringent conditions", as hereinabove defined.

Once the sequence is known, the gene encoding a particular type C lectin can also be obtained by chemical synthesis, following one of the methods described in Engels and Uhlmann, *Agnew. Chem. Int. Ed. Engl.* 28, 716 (1989). These methods include triester, phosphite, phosphoramidite and H-phosphonate methods, PCR and other autoprimer methods, and oligonucleotide syntheses on solid supports.

2. Cloning and expression of nucleic acid encoding the novel type C lectins

Once the nucleic acid encoding a novel type C lectin is available, it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence. Construction of suitable vectors containing one or more of the above listed components, the desired coding and control sequences, employs standard ligation techniques. Isolated plasmids or DNA fragments are cleaved, tailored, and religated in the form desired to generate the plasmids required. For analysis to confirm correct sequences in plasmids constructed, the ligation mixtures are commonly used to transform *E. coli* cells, e.g. *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9, 309 (1981) or by the method of Maxam et al., *Methods in Enzymology* 65, 499 (1980).

The polypeptides of the present invention may be expressed in a variety of prokaryotic and eukaryotic host cells. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., i Bio/Technology 6, 47–55 (1988); Miller et al., in *Genetic Engineering,* Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the type C lectin DNA. During incubation of the plant cell culture with *A. tumefaciens,* the DNA encoding a type C lectin is transferred to the plant cell host such that it is transfected, and will, under appropriate conditions, express the type C lectin DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture,* Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells (BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly useful in the practice of this invention are expression vectors that provide for the transient expression in mammalian cells of DNA encoding a novel type C lectin herein. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a native type C lectin herein.

Other methods, vectors, and host cells suitable for adaptation to the synthesis of the type C lectins in recombinant vertebrate cell culture are described in Getting et al., *Nature* 293, 620–625 (1981); Mantel et al., *Nature* 281, 40–46 (1979); Levinson et al.; EP 117,060 and EP 117,058. Particularly useful plasmids for mammalian cell culture expression of the type C lectin polypeptides are pRK5 (EP 307, 247), or pSVI6B (PCT Publication No. WO 91/08291).

Other cloning and expression vectors suitable for the expression of the type C lectins of the present invention in a variety of host cells are, for example, described in EP 457,758 published Nov. 27, 1991. A large variety of expression vectors is now commercially available. An exemplary commercial yeast expression vector is pPIC.9 (Invitrogen), while an commercially available expression vector suitable for transformation of *E. coli* cells is PET15b (Novagen).

C. Culturing the Host Cells

Prokaryote cells used to produced the type C lectins of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat. Nos. 4,767,704; 4,657,866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the type C lectins of this invention may be produced by homologous recombination, or with recombinant production methods utilizing control elements introduced into cells already containing DNA encoding the particular type C lectin.

D. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. A particularly sensitive staining technique suitable for use in the present invention is described by Hse et al., *Am. J. Clin. Pharm.* 75, 734–738 (1980).

Antibodies useful for immunohistochemical staining and/or assay of sample fluids may be either monoclonal or polyclonal, and may be prepared in any animal. Conveniently, the antibodies may be prepared against a native type C lectin polypeptide, or against a synthetic peptide based on the DNA sequence provided herein as described further hereinbelow.

E. Amino Acid Sequence Variants of a native type C lectins

Amino acid sequence variants of native type C lectins are prepared by methods known in the art by introducing appropriate nucleotide changes into a native type C lectin DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the native type C lectin, the amino acid sequence variants of type C lectins are preferably constructed by mutating the DNA, either to arrive at an allele or an amino acid sequence variant that does not occur in nature.

One group of mutations will be created within the fibronectin type II domain or within one or more of the type C lectin domains (preferably within the lectin-like domains 1–3) of a novel native type C lectin of the present invention. These domains are believed to be functionally important, therefore, alterations, such as non-conservative substitutions, insertions and/or deletions in these regions are expected to result in genuine changes in the properties of the native receptor molecules. The tyrosine residue at position 1451 of the novel murine and human type C lectins and the surrounding amino acids are also believed to have a functional significance, since this tyrosine is conserved in type C lectins, and has been previously found to be important for the endocytosis of the phospholipase A2 receptor. Accordingly, amino acid alterations in this region are also believed to result in variants with properties significantly different from the corresponding native polypeptides. Non-conservative substitutions within these functionally important domains may result in variants which loose the carbohydrate recognition and binding ability of their native counterparts, or have increased carbohydrate recognition properties or enhanced selectivity as compared to the corresponding native proteins.

Alternatively or in addition, amino acid alterations can be made at sites that differ in novel type C lectins from various species, or in highly conserved regions, depending on the goal to be achieved. Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3. One helpful technique is called "alanine scanning" (Cunningham and Wells, *Science* 244, 1081–1085 [1989]).

In yet another group of the variant type C lectins of the present invention, one or more of the functionally less significant domains may be deleted or inactivated. For example, the deletion or inactivation of the transmembrane domain yields soluble variants of the native proteins. Alternatively, or in addition, the cytoplasmic domain may be deleted, truncated or otherwise altered.

Naturally-occurring amino acids are divided into groups based on common side chain properties:
(1) hydrophobic: norleucine, met, ala, val, leu, ile;
(2) neutral hydrophobic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another. Substantial changes in function or immunological identity are made by selectin substitutions that are less conservative, i.e. differ more significantly in their effect on maintaining (a) the structure of the polypeptide backbone in the area of substitution, for example as a sheet or helical conformation, (b) the charge or hydrophobicity of the molecule at the target site or (c) the bulk of the side chain. The substitutions which in general are expected to produce the greatest changes in the properties of the novel native type C lectins of the present invention will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g. glycine.

Substitutional variants of the novel type C lectins of the present invention also include variants where functionally homologous (having at least about 40%–50% homology) domains of other protens are substituted by routine methods for one or more of the above-identified domains within the novel type C lectin structure. For example, the cysteine-rich domain, the fibronectin type II domain, or one or more of the first three carbohydrate recognition (CDR) domain of a novel type C lectin of the present invention can be replaced by a corresponding domain of a macrophage mannose receptor, a phospholipase A2 receptor or a DEC 205 receptor.

Amino acid sequence deletions generally range from about 1 to 30 residues, more preferably about 1 to 10 residues, and typically are contiguous. Typically, the transmembrane and cytoplasmic domains, or only the cytoplasmic domains are deleted. However, deletion from the C-terminal to any other suitable N-terminal to the transmembrane region which preserves the biological activity or immunological cross-reactivity of a native type C lectin is suitable.

A preferred class of substitutional and/or deletional variants of the present invention are those involving a transmembrane region of a novel type C lectin molecule. Transmembrane regions are highly hydrophobic or lipophilic domains that are the proper size to span the lipid bilayer of the cellular membrane. They are believed to anchor the lectin in the cell membrane, and allow for homo- or heteropolymeric complex formation. Inactivation of the transmembrane domain, typically by deletion or substitution of transmembrane domain hydroxylation residues, will facilitate recovery and formulation by reducing its cellular or membrane lipid affinity and improving its aqueous solubility. It the transmembrane and cytoplasmic domains are deleted one avoids the introduction of potentially immunogenic epitops, wither by exposure of otherwise intracellular polypeptides that might be recognized by the body as foreign or by insertion of heterologous polypeptides that are potentially immunogenic. Inactivation of the membrane binding function is accomplished by deletion of sufficient residues to produce a substantially hydrophilic hydropathy profile at this site or by substituting with heterologous residues which accomplish the same result.

A principle advantage of the transmembrane inactivated variants of the type C lectins of the present invention is that they may be secreted into the culture medium of recombinant hosts. These variants are soluble in body fluids such as blood and do not have an appreciable affinity for cell membrane lipids, thus considerably simplifying their recovery from recombinant cell culture. As a general proposition, such soluble variants will not have a functional transmembrane domain and preferably will not have a functional cytoplasmic domain. For example, the transmembrane domain may be substituted by any amino acid sequence, e.g. a random or predetermined sequences of about 5 to 50 serine, threonine, lysine, arginine, glutamine, aspartic acid and like hydrophilic residues, which altogether exhibit a hydrophilic hydropathy profile. Like the deletional (truncated) soluble variants, these variants are secreted into the culture medium of recombinant hosts.

Amino acid insertions include amino- and/or carboxylterminal fusions ranging in length from one residue to polypeptides containing a hundred or more residues, as well as intrasequence insertions of single or multiple amino acid residues. Intrasequence insertions (i.e. insertions within the novel type C lectin amino acid sequence) may range generally from about 1 to 10 residues, more preferably 1 to 5 residues, more preferably 1 to 3 residues. Examples of terminal insertions include the type C lectins with an N-terminal methionyl residue, an artifact of its direct expression in bacterial recombinant cell culture, and fusion of a heterologous N-terminal signal sequence to the N-terminus of the type C lectin molecule to facilitate the secretion of the mature type C lectin from recombinant host cells. Such signal sequences will generally be obtained from, and thus homologous to, the intended host cell species. Suitable sequences include STII or Ipp for *E. coli*, alpha factor for yeast, and viral signals such as herpes gD for mammalian cells.

Other insertional variants of the native type C lectin molecules include the fusion of the N- or C-terminus of the type C lectin molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Further insertional variants are immunologically active derivatives of the novel type C lectines, which comprise the lectin and a polypeptide containing an epitope of an immunologically competent extraneous polypeptide, i.e. a polypeptide which is capable of eliciting an immune response in the animal to which the fusion is to be administered or which is capable of being bound by an antibody raised against an extraneous polypeptide. Typical examples of such immunologically competent polypeptides are allergens, autoimmune epitopes, or other potent immunogens or antigens recognized by pre-existing antibodies in the fusion recipient, including bacterial polypeptides such as trpLE, β-glactosidase, viral polypeptides such as herpes gD protein, and the like.

Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into novel type C lectin molecule or fragment thereof by (a) peptide bond(s). These products therefore consist of a linear polypeptide chain containing the type C lectin epitope and at least one epitope foreign to the type C lectin. It will be understood that it is within the scope of this invention to introduce the epitopes anywhere within a type C lectin molecule of the present invention or a fragment thereof. These immunogenic insertions are particularly useful when formulated into a pharmacologically acceptable carrier and administered to a subject in order to raise antibodies against the type C lectin molecule, which antibodies in turn are useful as diagnostics, in tissue-typing, or in purification of the novel type C lectins by immunoaffinity techniques known per se. Alternatively, in the purification of the type C lectins of the present invention, binding partners for the fused extraneous polypeptide, e.g. antibodies, receptors or ligands, are used to adsorb the fusion from impure admixtures, after which the fusion is eluted and, if desired, the novel type C lectin is recovered from the fusion, e.g. by enzymatic cleavage.

Since it is often difficult to predict in advance the characteristics of a variant type C lectin, it will be appreciated that some screening will be needed to select the optimum variant.

After identifying the desired mutation(s), the gene encoding a type C lectin variant can, for example, be obtained by chemical synthesis as hereinabove described. More preferably, DNA encoding a type C lectin amino acid sequence variant is prepared by site-directed mutagenesis of DNA that encodes an earlier prepared variant or a nonvariant version of the type C lectin. Site-directed (site-specific) mutagenesis allows the production of type C lectin variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 153, 3 [1987]) may be employed to obtain single-stranded DNA. Alternatively, nucleotide substitutions are introduced by synthesizing the appropriate DNA fragment in vitro, and amplifying it by PCR procedures known in the art.

The PCR technique may also be used in creating amino acid sequence variants of a novel type C lectin. In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 μl. The reaction mixture is overlayered with 35 μl mineral oil. The reaction is denatured for 5 minutes at 100° C., placed briefly on ice, and then 1 μl *Thermus aquaticus* (Taq) DNA polymerase (5 units/l), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)].

Additionally, the so-called phagemid display method may be useful in making amino acid sequence variants of native or variant type C lectins or their fragments. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, the preferred coat protein is the M13 Phage gene III coat protein. The preferred host is *E coli*, and protease-deficient strains of *E. coli*.

Further details of the foregoing and similar mutagenesis techniques are found in general textbooks, such as, for example, Sambrook et al., supra, and *Current Protocols in Molecular Biology*, Ausubel et al. eds., supra.

F. Glycosylation variants

Glycosylation variants are included within the scope of the present invention. They include variants completely lacking in glycosylation (unglycosylated), variants having at least one less glycosylated site than the native form (deglycosylated) as well as variants in which the gycosylation has been changed. Included are deglycosylated and unglycosylated amino acid sequences variants, deglycosylated and unglycosylated native type C lectins, and other glycosylation variants. For example, substitutional or deletional mutagenesis may be employed to eliminate the N- or O-linked glycosylation sites in the a native or variant type C lectin of the present invention, e.g. the asparagine residue may be deleted or substituted for another basic residue such as lysine or histidine. Alternatively, flanking residues making up the glycosylation site may be substituted or deleted, eventhough the asparagine residues remain unchanged, in order to prevent glycosylation by eliminating the glycosylation recognition site.

Additionally, unglycosylated type C lectins which have the glycosylation sites of a native molecule may be produced in recombinant prokaryotic cell culture because prokaryotes are incapable of introducing glycosylation into polypeptides.

Glycosylation variants may be produced by selecting appropriate host cells or by in vitro methods. Yeast and insect cells, for example, introduce glycosylation which varies significantly from that of mammalian systems. Similarly, mammalian cells having a different species (e.g. hamster, murine, porcine, bovine or ovine), or tissue origin (e.g. lung, liver, lymphoid, mesenchymal or epidermal) than the source of the type C lectin are routinely screened for the ability to introduce variant glycosylation as characterized for example by elevated levels of mannose or variant ratios of mannose, fucose, sialic acid, and other sugars typically found in mammalian glycoproteins. In vitro processing of the type C lectin typically is accomplished by enzymatic hydrolysis, e.g. neuraminidate digestion.

G. Covalent Modifications

Covalent modifications of the novel type C lectins of the present invention are included within the scope herein. Such modifications are traditionally introduced by reacting targeted amino acid residues of the type C lectins with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the type C lectin, or for the preparation of anti-type C lectin antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intramolecular aggregates of the type C lectins with polypeptides as well as for cross-linking the type C lectin polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the $\alpha$-amino groups of lysine, arginine, and histidine side chains [T. E. Creighton, *Proteins: Structure and Molecular Properties,* W. H. Freeman & Co., San Francisco, pp. 79–86 (1983)].

Further derivatives of the type C lectins herein are the so called "immunoadhesins", which are chimeric antibody-like molecules combining the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig-" or "Fc-fusion protein", or "receptor-globulin."

To date, more than fifty immunoadhesins have been reported in the art. Immunoadhesins reported in the literature include, for example, fusions of the T cell receptor (Gascoigne et al., *Proc. Natl. Acad. Sci. USA* 84, 2936–2940 [1987]); CD4 (Capon et al, *Nature* 337, 525–531 [1989]; Traunecker et al., *Nature* 339, 68–70 [1989]; Zettmeissl et al., *DNA Cell Biol. USA* 9, 347–353 [1990]; Byrn et al., *Nature* 344, 667–670 [1990]); L-selectin (homing receptor) (Watson et al., *J. Cell. Biol.* 110, 2221–2229 [1990]; Watson et al., *Nature* 349, 164–167 [1991]); E-selectin [Mulligan et al., *J. Immunol.* 151, 6410–17 [1993]; Jacob et al., *Biochemistry* 34, 1210–1217 [1995]); P-selectin (Mulligan et al., supra; Hollenbaugh et al., *Biochemistry* 34, 5678–84 [1995]); ICAM-1 (Stauton et al., *J. Exp. Med.* 176, 1471–1476 [1992]; Martin et al., *J. Virol.* 67, 3561–68 [1993]; Roep et al., *Lancet* 343, 1590–93 [1994]); ICAM-2 (Damle et al., *J. Immunol.* 148, 665–71 [1992]); ICAM-3 (Holness et al., *J. Biol. Chem.* 270, 877–84 [1995]); LFA-3 (Kanner et al., *J. Immunol.* 148, 2–23–29 [1992]); L1 glycoprotein (Doherty et al., *Neuron* 14, 57–66 [1995]); TNF-R1 (Ashkenazi et al., *Proc. Natl. Acad. Sci. USA* 88, 10535–539 [1991]; Lesslauer et al., *Eur. J. Immunol.* 21, 2883–86 [1991]; Peppel et al., *J. Exp. Med.* 174, 1483–1489 [1991]); TNF-R2 (Zack et al., *Proc. Natl. Acad. Sci. USA* 90, 2335–39 [1993]; Wooley et al., *J. Immunol.* 151, 6602–07 [1993]); CD44 [Aruffo et al., *Cell* 61, 1303–1313 (1990)]; CD28 and B7 [Linsley et al., *J. Exp. Med.* 173, 721–730 (1991)]; CTLA-4 [Lisley et al., *J. Exp. Med.* 174, 561–569 (1991)]; CD22 [Stamenkovic et al., *Cell* 66. 1133–1144 (1991)]; NP receptors [Bennett et al., *J. Biol. Chem.* 266, 23060–23067 (1991)]; IgE receptor α [Ridgway and Gorman, *J. Cell. Biol.* 115, abstr. 1448 (1991)]; HGF receptor [Mark, M. R. et al., 1992, *J. Biol. Chem.* submitted]; IFN-γR α- and β-chain [Marsters et al., *Proc. Natl. Acad. Sci. USA* 92, 5401–05 [1995]); trk-A, -B, and -C (Shelton et al., *J. Neurosci.* 15, 477–91 [1995]); IL-2 (Landolfi, *J. Immunol.* 146, 915–19 [1991]); IL-10 (Zheng et al., *J. Immunol.* 154, 5590–5600 [1995]).

The simplest and most straightforward immunoadhesin design combines the binding region(s) of the 'adhesin' protein with the hinge and Fc regions of an immunoglobulin heavy chain. Ordinarily, when preparing the lectin-immunoglobulin chimeras of the present invention, nucleic acid encoding the desired type C lectin polypeptide will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the lectin-immunoglobulin chimeras.

In a preferred embodiment, the sequence of a native, mature lectin polypeptide, or a soluble (transmembrane domain-inactivated) form thereof, is fused to the N-terminus of the C-terminal portion of an antibody (in particular the Fc domain), containing the effector functions of an immunoglobulin, e.g. IgG-1. It is possible to fuse the entire heavy chain constant region to the lectin sequence. However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. In a particularly preferred embodiment, the type C lectin sequence (full length or soluble) is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the lectin-immunoglobulin chimeras are assembled as multimers, and particularly as homodimers or -tetramers (WO 91/08298). Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled lectin-immunoglobulin chimeras within the scope herein are schematically diagrammed below:

(a) $AC_L$-$AC_L$;

(b) $AC_H$-[$AC_H$, $AC_L$-$AC_H$, $AC_L$-$V_HC_H$, or $V_LC_L$-$AC_H$];

(c) $AC_L$-$AC_H$-[$AC_L$-$AC_H$, $AC_L$-$V_HC_H$, $V_LC_L$-$AC_H$, or $V_LC_L$-$V_HC_H$];

(d) $AC_L$-$V_HC_H$-[$AC_H$, or $AC_L$-$V_HC_H$, or $V_LC_L$-$AC_H$];

(e) $V_LC_L$-$AC_H$-[$AC_L$-$V_HC_H$, or $V_LC_L$-$AC_H$]; and (f) $[A\text{-}Y]_n$-$[V_LC_L\text{-}V_HC_H]_2$, wherein each A represents identical or different novel type C lectin polypeptide amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the type C lectin amino acid sequences can be inserted between immunoglobulin heavy chain and light chain sequences such that an immunoglobulin comprising a chimeric heavy chain is obtained. In this embodiment, the type C lectin polypeptide sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., *Mol. Immunol.* 28, 1027–1037 (1991).

Although the presence of an immunoglobulin light chain is not required in the immunoadhesins of the present invention, an immunoglobulin light chain might be present either covalently associated to an type C lectin-immunoglobulin heavy chain fusion polypeptide, or directly fused to the type C lectin polypeptide. In the former case, DNA encoding an immunoglobulin light chain is typically coexpressed with the DNA encoding the type C lectin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Method suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG-1 and IgG-3 immunoglobulin sequences is preferred. A major advantage of using IgG-1 is that IgG-1 immunoadhesins can be purified efficiently on immobilized protein A. In contrast, purification of IgG-3 requires protein G, a significantly less versatile medium. However, other structural and functional properties of immunoglobulins should be considered when choosing the Ig fusion partner for a particular immunoadhesin construction. For example, the IgG-3 hinge is longer and more flexible, so it can accommodate larger 'adhesin' domains that may not fold or function properly when fused to IgG-1. While IgG immunoadhesins are typically mono- or bivalent, other Ig subtypes like IgA and IgM may give rise to dimeric or pentameric structures, respectively, of the basic Ig homodimer unit. Multimeric immunoadhesins are advantageous in that they can bind their respective targets with greater avidity than their IgG-based counterparts. Reported examples of such structures are CD4-IgM (Traunecker et al., supra); ICAM-IgM (Martin et al., *J. Virol.* 67, 3561–68 [1993]); and CD2-IgM (Arulanandam et al., *J. Exp. Med.* 177, 1439–50 [1993]).

For type C lectin-Ig immunoadhesins, which are designed for in vivo application, the pharmacokinetic properties and the effector functions specified by the Fc region are important as well. Although IgG-1, IgG-2 and IgG-4 all have in vivo half-lives of 21 days, their relative potencies at activating the complement system are different. IgG-4 does not activate complement, and IgG-2 is significantly weaker at complement activation than IgG-1. Moreover, unlike IgG-1, IgG-2 does not bind to Fc receptors on mononuclear cells or neutrophils. While IgG-3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG-1 has only four serologically-defined allotypic sites, two of which (G1m and 2) are located in the Fc region; and one of these sites G1m1, is non-immunogenic. In contrast, there are 12 serologically-defined allotypes in IgG-3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

Type C lectin-Ig immunoadhesins are most conveniently constructed by fusing the cDNA sequence encoding the type C lectin portion in-frame to an Ig cDNA sequence. However, fusion to genomic Ig fragments can also be used (see, e.g. Gascoigne et al., *Proc. Natl. Acad. Sci. USA* 84, 2936–2940 [1987]; Aruffo et al., *Cell* 61, 1303–1313 [1990]; Stamenkovic et al., *Cell* 66, 1133–1144 [1991]). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques.

Other derivatives of the novel type C lectins of the present invention, which possess a longer half-life than the native molecules comprise the lectin or a lectin-immunoglobulin chimera, covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogenous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the novel type C lectin or to the lectin-immunoglobulin chimeras though a multifunctional crosslinking agent which reacts with the polymer and one or more amino acid or sugar residues of the type C lectin or lectin-immunoglobulin chimera to be linked. However, it is within the scope of the invention to directly crosslink the polymer by reacting a derivatized polymer with the hybrid, or via versa.

The covalent crosslinking site on the type C lectin or lectin-Ig includes the N-terminal amino group and epsilon amino groups found on lysine residues, as well as other amino, imino, carboxyl, sulfhydryl, hydroxyl or other hydrophilic groups. The polymer may be covalently bonded directly to the hybrid without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylcloroformate or P-nitrophenylcloroformate activated PEG.) Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase, (either of which produces the aldehyde derivative of the carbohydrate), followed by reaction with hydrazide or amino derivatized polymers, in the same fashion as is described by Heitzmann et al., P.N.A.S., 71, 3537–41 (1974) or Bayer et al., Methods in Enzymology 62, 310 (1979), for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

"Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein (e.g. a type C lectin-immunoglobulin chimera), the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., Anal Biochem. 131, 25–33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., J. Polym. Sci. Polym. Chem. Ed. 22, 341–52 [1984]). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred.

The long half-life conjugates of this invention are separated from the unreacted starting materials by gel filtration. Heterologous species of the conjugates are purified from one another in the same fashion. The polymer also may be water-insoluble, as a hydrophilic gel.

The novel type C lectins may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in Remington's Pharmaceutical Sciences, 16th Edition, Osol, A., Ed. (1980).

H. Antibody preparation (i) Polyclonal antibodies

Polyclonal antibodies to a type C lectin of the present invention generally are raised in animals by multiple subcutaneous (sc) or intraperitoneal (ip) injections of the type C lectin and an adjuvant. It may be useful to conjugate the lectin or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the immunogenic conjugates or derivatives by combining 1 mg or 1 $\mu$g of conjugate (for rabbits or mice, respectively) with 3 volumes of Freud's complete adjuvant and injecting the solution intradermally at multiple sites. One month later the animals are boosted with 1/5 to 1/10 the original amount of conjugate in Freud's complete adjuvant by subcutaneous injection at multiple sites. 7 to 14 days later the animals are bled and the serum is assayed for anti-type C lectin antibody titer. Animals are boosted until the titer plateaus. Preferably, the animal boosted with the conjugate of the same type C lectin, but conjugated to a different protein and/or through a different cross-linking reagent. Conjugates also can be made in recombinant cell culture as protein fusions. Also, aggregating agents such as alum are used to enhance the immune response.

(ii) Monoclonal antibodies Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, the anti-type C lectin monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of a type C lectin monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a type C lectin and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}$H, $^{14}$C, $^{32}$P, $^{35}$S, or $^{125}$I, a fluorescent or chemiluminescent compound, such as fluorescein isothiocyanate, rhodamine, or luciferin; biotin; radioactive isotopic labels, such as, e.g., $^{125}$I, $^{32}$P, $^{14}$C, or $^{3}$H, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques,* pp. 147–158 (CRC Press, Inc., 1987).

(iii) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986); Riechmann et al., *Nature* 332, 323–327 (1988); Verhoeyen et al., *Science* 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551–255 (1993); Jakobovits et al., *Nature* 362, 255–258 (1993).

(iv) Bispecific antibodies

Bispecific antibodies are monoclonal, preferably human or humanized, antibodies that have binding specificities for at least two different antigens. In the present case, one of the binding specificities is for a type C lectin of the present invention the other one is for any other antigen, for example, another member of the endocytic type C lectin family, or a selectin, such as, E-, L- or P-selectin. Such constructs can also be referred to as bispecific immunoadhesins. Methods for making bispecific antibodies (and bispecific immunoadhesins) are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al, *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT application WO 94/04690 published Mar 3, 1994

For further details of generating bispecific antibodies see, for example, Suresh et al., *Methods in Enzymology* 121, 210 (1986).

(v) Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

I. Peptide and non-peptide analogs

Peptide analogs of the type C lectins of the present invention are modelled based upon the three-dimensional structure of the native polypeptides. Peptides may be synthesized by well known techniques such as the solid-phase synthetic techniques initially described in Merrifield, *J. Am. Chem. Soc.* 15, 2149–2154 (1963). Other peptide synthesis techniques are, for examples, described in Bodanszky et al., Peptide Synthesis, John Wiley & Sons, 2nd Ed., 1976, as well as in other reference books readily available for those skilled in the art. A summary of peptide synthesis techniques may be found in Stuart and Young, Solid Phase Peptide Synthelia, Pierce Chemical Company, Rockford, Ill. (1984). Peptides may also be prepared by recombinant DNA technology, using a DNA sequence encoding the desired peptide.

In addition to peptide analogs, the present invention also contemplates non-peptide (e.g. organic) compounds which display substantially the same surface as the peptide analogs of the present invention, and therefore interact with other molecules in a similar fashion.

J. Use of the type C lectins

Amino acid sequence variants of the native type C lectins of the present inventon may be employed therapeutically to compete with the normal binding of the native proteins to their ligands. The type C lectin amino acid sequence varants are, therefore, useful as competitive inhibitors of the biological activity of native type C lectins.

Native type C lectins and their amino acid sequence variants are useful in the identification and purification of their native ligands. The purification is preferably performed by immunoadhesins comprising a type C lectin amino acid sequence retaining the qualitative ability of a native type C lectin of the present invention to recognize its native carbohydrate ligand.

The native type C lectins of the present invention are further useful as molecular markers of the tissues in which they are expressed.

Furthermore, the type C lectins of the present invention provide valuable sequence motifs which can be inserted or substituted into other native members of the endocytic type C lectins, such as a native mannose receptor, DEC205 receptor, or phospholipase A2 receptor. The alteration of these native proteins by the substitution or insertion of sequences from the novel type C lectins of the present invention can yield variant molecules with altered biological properties, such as ligand binding affinity or ligand specificity. For example, one or more lectin domains of another member of the endocytic type C lectin family may be entirely or partially replaced by lectin domain sequences derived from the type C lectins of the present invention. Similarly, fibronectin type II domain sequences from the type C lectins herein may be substituted or inserted into the amino acid sequences of other type C lectins.

Nucleic acid encoding the type C lectins of the present invention is also useful in providing hybridization probes for searching cDNA and genomic libraries for the coding sequence of other type C lectins.

Further details of the invention will be apparent from the following non-limiting example.

EXAMPLE

New murine and human type C lectins

A. Materials and Methods

1. Isolation of cDNAs coding the murine and human lectins.

According to the EST sequence, two 33 mers were synthesized (5' CCG GAA TTC CGG TTT GTT GCC ACT GGG AGC AGG3' (SEQ. ID. NO: 10) and 5'CCC AAG CTT GAA GTG GTC AGA GGC ACA GTT CTC3' (SEQ. ID. NO: 11)) for PCR (94° C., 1 min, 60° C. 1 min and 72° C. 1 min, for 35 cycles) using 5 microliters of a human heart cDNA library (Clontech) as template. The 260-base PCR product was cloned (TA cloning kit, Invitrogen) and used as a probe to screen a human heart cDNA library as well as to probe Northern and Southern blots (Clontech). The same pair of primers was also used to amplify a mouse heart cDNA library with lower annealing temperature (55° C.) and a mouse product with the same size (260 bp) was obtained. Screening of approximately 500,000 plaques from cDNA libraries was done using standard procedure with a randomly-labelled DNA probe. Single positive phage clones were isolated after two more rounds of rescreening. The size of the inserts was identified by PCR using two primes from the lambda gt10vector and the inserts were subcloned. DNA sequencing was performed on an Applied Biosystems automated DNA sequencer. To clone the 5 prime region of the transcripts, 5' RACE (Rapid Amplification of cDNA Ends) was performed using the most 5' end of the known sequence and the protocol for 5' RACE supplied by the manufacturer (Marathon-Ready cDNAs, Clontech) was followed. RACE products were subcloned and sequenced as described.

2. Northern and Southern blot analyses

The DNA probes were prepared by agarose gel purification (Gel Extraction Kit, Qiagen) and random labelling (Pharmacia). Blot hybridization was performed as described in manufacturer's instruction using commercially supplied blots (Clontech).

3. Characterization of the fetal liver transcript

Sequencing of the RACE products using human fetal liver marathon-ready cDNA (Clontech) as template revealed a novel 5 prime region not found in the original heart-derived clones. To further characterize this transcript, PCR was performed on heart, lung and fetal liver using a common downstream primer with two different upstream primers. One upstream primer is from the lectin sequence, which is not present in fetal liver clone, and the other is from fetal liver unique sequence. The PCR products were analysed on agarose gel and hybridized by an oligonucleotide common to both transcripts.

4. Isolation of genomic clones encoding the murine lectin

A129 mouse-derived embryonic cell (ES) genomic library was used for the screening by two lectin cDNA sequences. One is from the 5' end of the lectin coding sequence and the other one is from the 3' end of the cDNA. Screening of 500,000 plaques yielded three kinds of lectin genomic clones; positive for the 5'-end probe, the 3'-end probe and both. Recombinant phage DNA was isolated from plate lysates (Wizard Lambda Preps, Promega) and digested by Not I. Genomic DNA inserts were subcloned into a Not I-digested pBlueScript SK vector using Rapid DNA Ligation Kit (Boehringer Mannheim), after heat inactivation of the restriction enzyme. The approximate locations of introns and exons were identified using dot-blot hybridization with specific oligonucleotide probes and PCR analysis of lambda clones using exon-specific probes. Physical mapping of the lectin gene was performed using restriction enzyme digestion of genomic clones followed by southern blot hybridization with exon-specific oligonucleotide probes.

5. In situ hybridization

In situ hybridization was performed essentially as previously described (Lasky et al., Cell 69(6), 927–38 [1992]). Briefly, antisense and sense riboprobes for this clone were generated by use of the polymerase chain reaction (PCR) to derive templates for subsequent in vitro transcription. In preparation for hybridization, sections were treated sequentially with 4% paraformaldehyde (10 minutes) and proteinase K (0.5 mg/mL, 15 minutes) and then prehybridized with 50 mL of hybridization buffer at 42° C. for 2 hours. Hybridization buffer consisted of 10% dextran sulfate, 2× SSC (sodium chloride/sodium citrate) and 50% formamide. Probes were added at a final concentration of 106 cpm/slide and the sections were incubated overnight at 55 C. Posthybridization washes consisted of 2× SSC containing 1 mM EDTA, before and after a 30 minute treatment with ribonuclease (20 mg/mL). A high-stringency wash consisting of 0.1× SSC containing EDTA was performed in a large volume for 2 hours at 55° C. Sections were then washed in 0.5× SSC, dehydrated in increasing concentrations of ethanol and then vacuum desiccated. Slides were covered with NTB2 nuclear emulsion (Eastman Kodak, Rochester, N.Y.) and exposed for up to 5 weeks. After the slides were developed they were counterstained with hematoxylin and eosin and evaluated by epiluminescent microscopy for positive hybridization. Serial sections of the tissues hybridized with the sense probes served as negative controls.

B. Results

The expressed sequence tag (EST) database is a large collection of random cDNA sequences from a diversity of libraries. We probed the EST database in silico with the lectin domain of E-selectin. As can be seen in FIG. 1, a sequence (T11885) was identified which showed low homology (~23%) to a region of the E-selectin lectin domain. While this homology appeared to be quite distant, we found that the residues that were identical were included in the subset of amino acids that have previously been shown to be conserved in the vast majority of type C lectins (Drickhamer, J. Biol. Chem. 263, 9557–9560 [1988]). In addition, searching the GenBank-EMBL database with the novel EST-derived E-selectin related sequence resulted in only type C lectin homologies (data not shown), again consistent with the novel sequence being a member of this large family of proteins.

Because the novel EST sequence was originally derived from a human heart cDNA library, a similar library was used for PCR analysis using primers deduced from the EST sequence. This resulted in a DNA fragment containing the same sequence as that found for the database entry, and this fragment was used to probe a human heart library. In addition, a murine fragment was also isolated using similar techniques, and this fragment was used for the isolation of a cDNA from a murine heart library. FIGS. 2A–2H illustrate the full length sequence obtained for the murine cDNA clone. As can be seen from this figure, this large transcript encoded a protein of 1,479 residues with a molecular weight of approximately 167 kD. The human sequence revealed approximately 90% amino acid sequence homology with the murine protein. The ATG translational initiation codon shown in the murine sequence is in the context of a Kozak translational start site, and there are two stop codons 5 prime to this ATG. A search of the GenBank with the deduced murine protein sequence revealed that this novel sequence was most closely related to the macrophage mannose receptor (32.5% identity) (Taylor et al, supra; Harris et al., supra), the phospholipase A2 receptor (34% identity) (Higishino et al., supra; Ishizaki et al., supra; Lambeau et al, supra) and the DEC 205 receptor (33% identity) (Jiang et al., supra), three members of the family of type C lectins containing multiple lectin domains which all mediate endocytosis (FIGS. 3A–3G). These levels of sequence homology are similar to those found when these three lectin-like receptors are compared to each other, consistent with the supposition that the novel cDNA described here is a new member of this family. Further homology analysis by domains revealed that the highest sequence homologies between these four related proteins were found in the fibronectin type II and lectin-like domains 1–3, consistent with the possibility that these domains might be functionally important (FIG. 4). In addition, analysis of the cytoplasmic domain of the novel type C lectin also revealed that it contained the a conserved tyrosine residue (residue number 1,451) in a context similar to the NSYY motif that has been previously found to be important for the endocytosis of the phospholipase A2 receptor (Zvaritch et al., supra). In summary, the novel receptor described here is related to three previously described lectins with an overall structure that consists of a signal sequence, a cysteine rich domain, a fibronectin type II domain, 8 type C lectin domains (10 such domains in the DEC 205 receptor), a transmembrane domain and a short cytoplasmic domain (FIG. 4).

C. Analysis of the genomic structure of the novel type C lectin

Figure 5A:
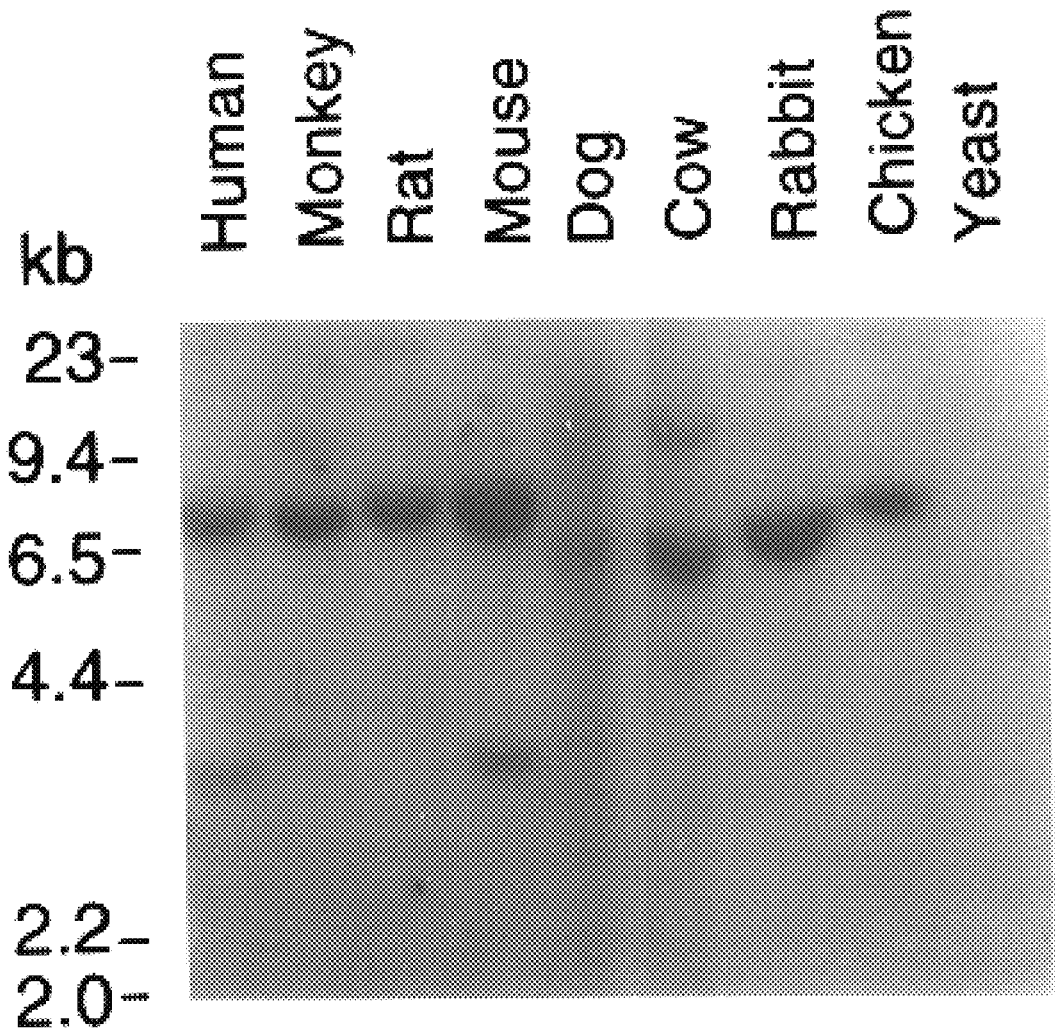
Figure 5B:
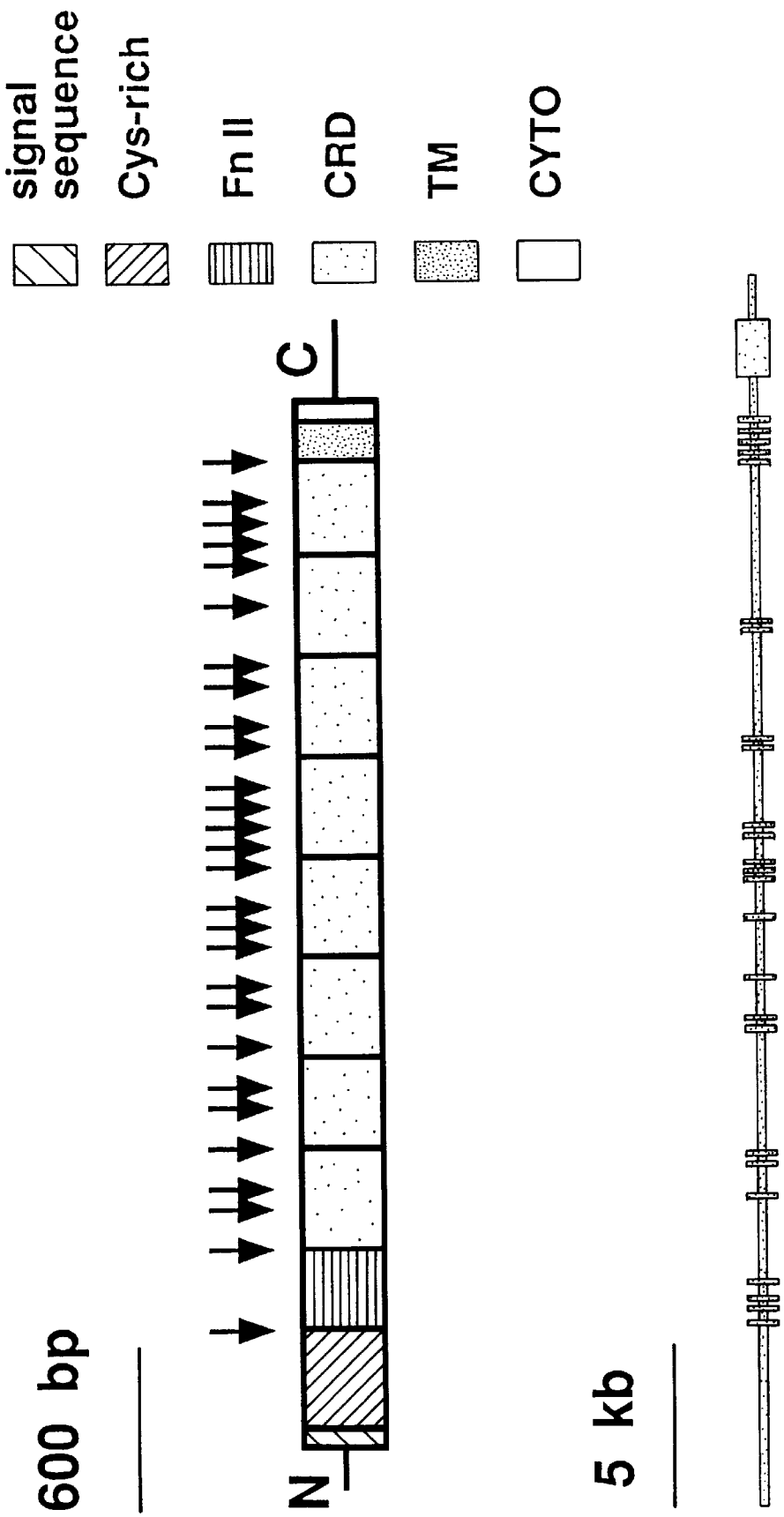

Southern blot analyses with a small region of the novel type C lectin revealed that it was encoded by a single copy, highly conserved gene, in agreement with the high degree of sequence homology between the murine and human cDNAs (FIG. 5). The gene encoding the murine form of the novel type C lectin, with the exception of the signal sequence and cysteine rich domain exons which could not be isolated from our library, was characterized using a combination of southern blotting, and PCR analysis of lambda clones using exon specific probes predicted from the human and murine macrophage mannose receptor gene structures (Kim et al., *Genomic* 14(3), 721–727 [1992]; Harris et al., *Biochem Biophys. Res. Commun.* 198(2), 682–92 [1994]). As can be seen from FIG. 5, the gene was interrupted by a minimum of 28 introns and was spread across at least 39 kB of DNA. This genomic structure is therefore highly reminiscent of that found for the human and murine macrophage mannose receptors, both of which were interrupted by a similar number of introns at similar sites. These data are thus consistent with the supposition that the members of this family of type C lectins were all derived from an original progenitor gene which was than duplicated and mutated to give rise to these four different proteins with different functions.

D. Northern blot analysis of transcripts encoding the novel type C lectin

Figure 7:
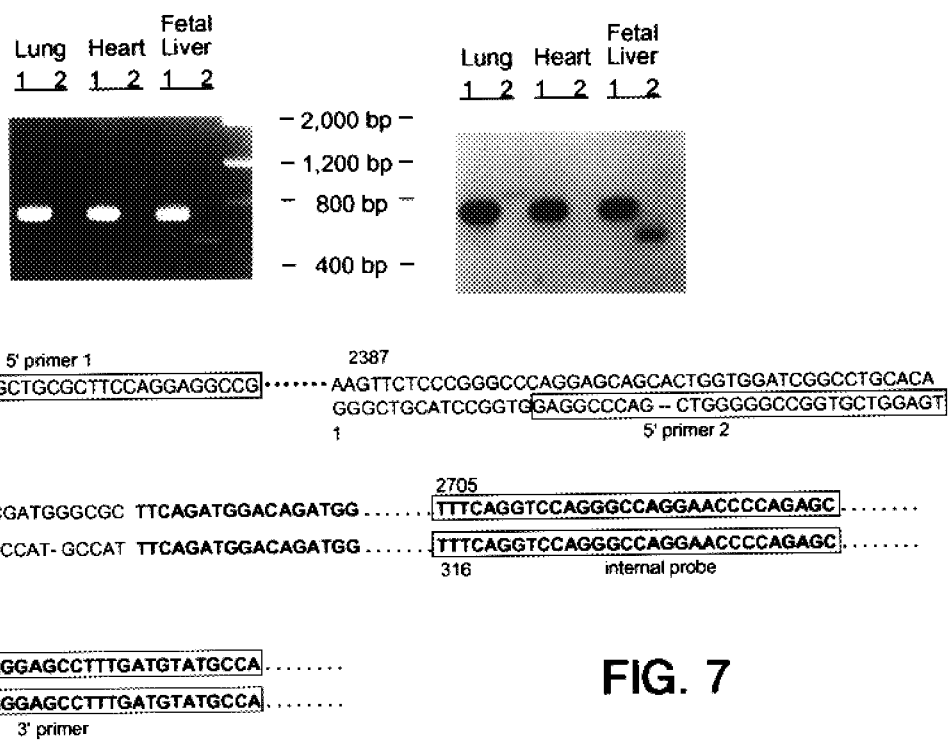
FIG. 7. Characterization of the 5 prime region of the alternatively spliced human fetal liver transcript. The sequence illustrates that the human full length (MRX) and alternately spliced (FL) transcript were identical from the region 3 prime to nucleotide 61 of the alternately spliced fetal liver clone. The top part of the figure illustrates PCR analysis using two 5 prime primers specific for either the full length transcript (primer 1) (SEQ. ID. NO: 12) or the alternately spliced transcript (primer 2) (SEQ. ID. NO: 13). The 3 prime PCR primer is shown at the end of the sequence and is identical in both cases (SEQ. ID. NO: 14). An internal oligonucleotide probe used for hybridization is shown as the middle primer and is also identical for both sequences (SEQ. ID. NO: 15). 1 or 2 in the top panels refer to the 5 prime primers utilized for the PCR reaction for each tissue. The panels illustrate that the smaller PCR fragment (2) corresponds to the alternately spliced transcript, and it is found only in the fetal liver and not in the lung or heart.
Figure 8A:
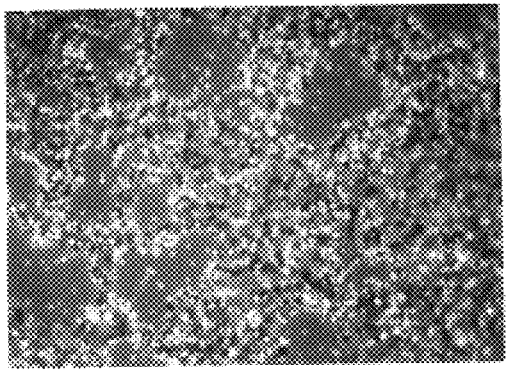
FIGS. 8A–8H. In situ hybridization analysis of neonatal and embryonic tissues with the novel type C lectin. A. Lung hybridized with antisense probe, B. Lung hybridized with sense probe, C. Kidney glomerulus hybridized with antisense probe, D. Choroid plexus hybridized with antisense probe, E. Developing sternum hybridized with antisense probe, F. Developing sternum hybridized with sense probe. G. Developing tooth hybridized with antisense probe, H. Developing cartilage of the larynx hybridized with antisense probe.
Figure 8B:
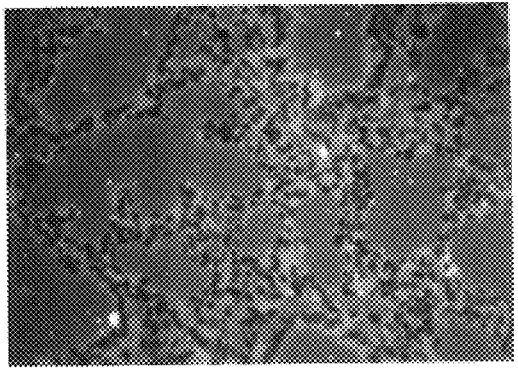
Figure 8C:
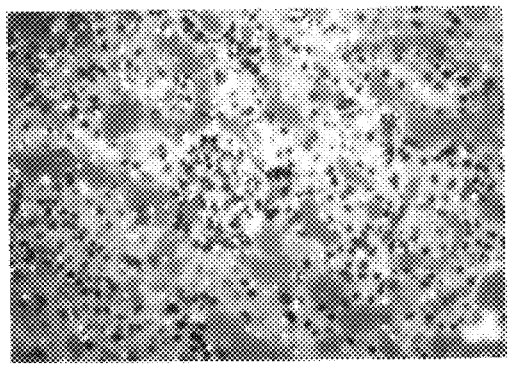
Figure 8D:
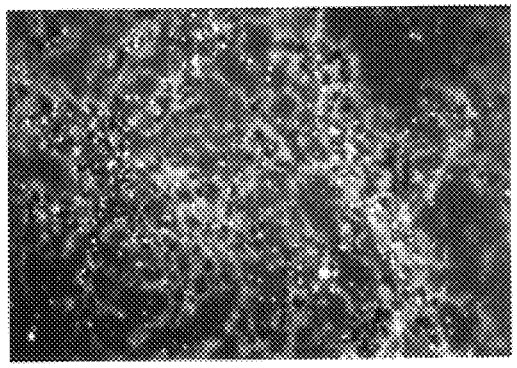
Figure 8E:
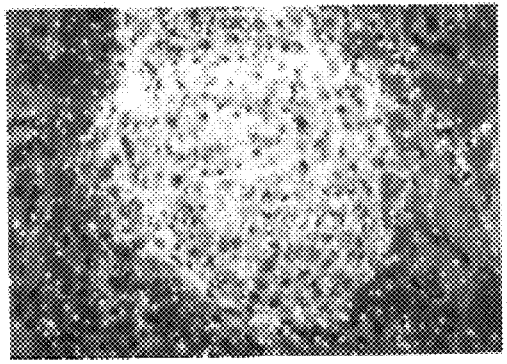
Figure 8F:
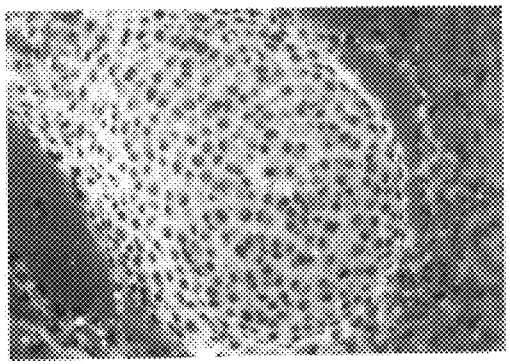
Figure 8G:
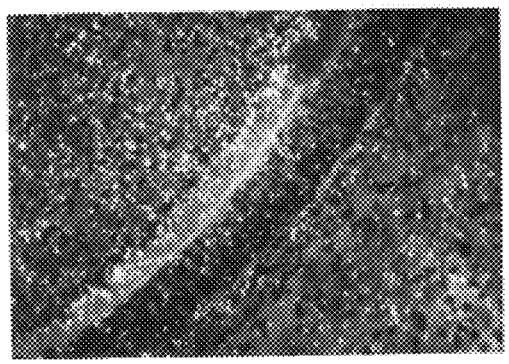
Figure 8H:
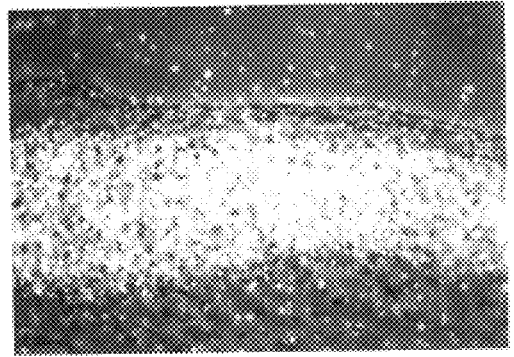

A diverse collection of murine and human tissues were analyzed for expression of the transcript encoding the novel type C lectin. As can be seen from FIG. 6, the transcript was found to be expressed in the earliest murine embryonic stage examined (day 7) and its expression continued throughout embryonic development. Analysis of human fetal tissues revealed that the transcript was highly expressed in lung and kidney. Interestingly, a truncated transcript was found to be expressed predominately in the fetal liver, and this transcript will be described in greater detail below. Analysis of adult murine tissues revealed that high levels of expression were detected in the heart, lung and kidney, with lower levels in the brain and muscle. Interestingly, the transcript in the adult liver in both humans and mice appears to be absent, further supporting the specificity of the alternately spliced transcript to the fetal liver. Analysis of expression in human tissues revealed that there were also high transcript levels in the heart as well as in prostate, testis, ovary and intestine, with lower levels in brain, placenta, lung, kidney, pancreas, spleen, thymus and colon. Analysis of expression in various transformed cells (FIG. 6) revealed that the novel lectin was transcribed in at least two different hematopoietic cell lines, in contrast to its apparent lack of expression in human peripheral blood leukocytes (PBL). In addition, several other transformed cell lines derived from various tumors were also positive for the expression of this lectin. In summary, analysis of expression of the novel type C lectin suggests that it is expressed in a diversity of tissues and throughout development, although it appears to be absent from adult liver and is found as smaller transcript in fetal liver. The expression of a smaller transcript in human fetal liver, together with the complex genomic structure described above, suggested that this RNA might have been produced through alternate splicing. Analysis of RACE clones derived from the fetal liver revealed that the smaller transcript appeared to have a divergent 5 prime sequence. In order to further characterize this transcript, a human fetal liver library was screened, and the resultant positive phage were sequenced. One positive phage was found which appeared to encode a partial cDNA which corresponded to the smaller transcript. Thus, as can be seen from FIG. 7, the resultant sequence is identical to the original, full length lectin until nucleotide 61, where a divergent sequence is found leading to the 5' end of the transcript contained within this phage. This is the identical splice site found for intron number 18 in the mannose receptor (Kim et al., supra, Harris et al., supra), which interrupts a region in the carboxy-terminus of the fifth lectin domain, consistent with alternate splicing. In order to demonstrate that this transcript exists, as well as to investigate its tissue specificity, specific primers were designed from the original transcript as well as from the smaller, alternately spliced transcript (FIG. 7). As can be seen from FIG. 7, analysis of lung, heart and fetal liver RNA revealed that the alternately spliced, small transcript was specific to the fetal liver, although this tissue also appeared to make the full length transcript as well. In addition, analysis of a tissue northern blot with a 30-mer oligonucleotide specific for the novel region in this transcript revealed a signal only in the fetal liver corresponding to this small RNA (data not shown). Because the size of the transcript on northern blots suggests that this alternately spliced transcript should extend for only a relatively short distance 5' to the lambda clone isolated here.

E. In situ hybridization analysis of the novel type C lectin

In order to examine the types of cells which expressed the transcript encoding the novel type C lectin, in situ hybridization analyses were performed using murine neonatal and adult tissues. As can be seen from FIG. 8, this transcript was found in two very divergent tissue types. For example, the northern blot analysis of murine adult tissues as well as human fetal tissues (FIG. 7) suggested a high level of expression of the transcript in lung, and FIG. 8 illustrates that this RNA was found to be clearly expressed in the lung. Although it is difficult to tell at the resolution of the in situ experiments the exact cellular location of the transcript, because of the highly vascularized nature of the lung, it is possible that it is expressed by the lung endothelium. The transcript was also found at a number of other highly endothelialized sites, including, for example, the choroid plexus and the kidney glomerulai (FIG. 8), but it was not universally expressed at detectable levels in all endothelium. In addition, examination by PCR of endothelial cell lines derived from murine yolk sac also demonstrated expression of the lectin (data not shown). The figure also illustrates that the transcript was found to be highly expressed by chondrocytes at sites of active cartilage deposition. As can be seen in this figure, the collagenous region of the larynx produced a high level of this transcript as did other bone forming regions in the neonate including the developing sternal bones as well as the developing teeth. These data suggest that, in contrast to the restricted expression of the previously reported members of this family, the novel type C lectin described here appears to be expressed in a diversity of highly endothelialized regions and bone forming sites in the embryo as well as in the adult.

G. Discussion

The recognition of cabohydrates by various calcium dependent, or type C, lectins has recently been acknowledged as a major aspect of a number of physiological phenomena. These include, for example, the adhesion of various leukocytic cells to the endothelium under the conditions of vascular flow (Lasky, Ann. Rev. Biochem. 64, 113–139 [1995]), the binding and engulfment of pathogenic organisms by macrophages (Harris et al, supra), the recognition of transformed cells by natural killer (NK) cells (Bezouska et al., Nature 372(6502), 150–7 [1994]) and the removal of desialated glycoproteins from the circulation. The importance of these types of interactions have been significantly highlighted by both naturally occurring as well as induced mutations. For example, naturally occurring human mutations in the circulating mannose binding protein result in sensitivity to various pathogenic infections in affected individuals (Lipscombe el al., Immunology 85(4), 660–7 [1995]), and the production of animals with mutations in various selectin genes precipitates profound defects in leukocyte trafficking (Mayadas et al., Cell 74(3), 541–554 [1993]; Arbones et al., Immunity 1, 247–260 [1994]). While neither naturally occurring nor induced mutations have yet been reported for the family of endocytic type C lectins, various in vitro data support the contention that these lectins are also important for a range of potentially critical functions. We here describe a novel member of the endocytic lectin family which contains many of the structural features of the previously described members but which reveals several differences in expression sites with potentially important functional implications. Comparison of the overall structure of the novel receptor reported here suggests that it is clearly a member of the endocytic type C lectin family. This is based upon the clearcut conservation of each of the protein motifs found in this family as compared to those found in the novel lectin. Thus, the novel receptor contains regions which are homologous to the cysteine rich, fibronectin type II and multiple lectin domain motifs found in the other three members of this lectin family, in addition to a signal sequence and transmembrane domain which would orient the receptor as a type1 transmembrane protein. Interestingly, the cytoplasmic domain is also homologous with the other members of this family, and this homology includes a conserved tyrosine within a context similar to the NSYY motif which is critical for endocytosis (Zvaritch et al., supra). Thus, while the levels of conservation between these family members appears to be quite low (~30–35%), their overall predicted protein domain structures as well as the exon structures of at least the genes for the human and murine mannose macrophage receptors (Kim et al. supra, Harris et al., supra), as well as the novel receptor reported here suggests that they are clearly a related family of receptors. Thus, it is highly likely that this novel receptor is involved in the uptake of ligands for the purpose of an endocytic response as has been found for the other proteins of this family.

With respect to ligand recognition by the novel receptor, previous work has implicated the type C lectin domains as being critical for the binding activity of the other members of this family. For example, various deletion analyses of both the macrophage mannose receptor (see the two Taylor et al. articles, supra) and the phospholipase A2 receptor (Ishizaki et al., supra) have revealed that the type C lectin motifs are involved with the binding of either high mannose containing glycoproteins (the macrophage mannose receptor) or to phospholipase A2 (the phospholipase A2 receptor). Interestingly, in the case of the latter receptor, the binding of phospholipase is not carbohydrate dependent, although this receptor will also bind with significant affinity to highly glycosylated neoglycoprotiens such as mannose-BSA (Lambeau et al., supra). The need for multiple carbohydrate recognition motifs is underlined by the finding that the affinity of the macrophage mannose receptor for glycosylated proteins is enhanced when more than one motif is expressed in the context of a truncated receptor (see the two Taylor et al. articles, supra). Because the DEC 205 receptor also appears to bind glycosylated antigens in order to enhance antigen presentation by dendritic cells and thymic epithelium (Jiang et al., supra), it seems highly likely that it too utilizes a multiplicity of lectin motifs for high affinity ligand binding. Finally, comparative analysis of the sequences of the type C lectin motifs in the novel receptor with those found in the co-crystal structure of the mannose binding protein and mannose (the two Weis et al. papers, supra, Drickhamer et al., supra) (K. Drickamer-personnel communication) demonstrates that many of the amino acids involved with the ligation of calcium and the recognition of either mannose or galactose are found in the first two lectin motifs of the novel protein, consistent with a role for these motifs in carbohydrate recognition. Interestingly, this is in contrast with the macrophage mannose receptor, where the fourth lectin type domain appears to be the one that is most critical for carbohydrate recognition (the two Taylor et al. papers, supra). In summary, these data thus support the contention that the related lectin reported here is also involved with the recognition of a highly glycosylated ligand(s) in order to mediate an endocytic uptake.

While the data reported here suggest that the mechanisms of ligand recognition by the novel endocytic type C lectin may be related to those previously described for the other family members, analysis of the expression patterns of this new protein suggest that it potentially performs a novel task(s). The expression patterns of two of the members of the endocytic lectin family, the macrophage mannose receptor and the DEC 205 receptor, reveal a highly restricted transcription of these proteins in macrophages and liver endothelial cells (the macrophage mannose receptor) or in dendritic cells and thymic epithelium (the DEC 205 receptor), and these patterns correlate with the known functions of these receptors in immune system function. A broader expression pattern is observed for the phospholipase A2 receptor. This endocytic receptor is expressed in various tissues of the embryo and the adult, including the heart, lung, kidney, skeletal muscle and liver in the adult mouse and the kidney in the embryonic human. This pattern is somewhat reminiscent of the novel receptor described here, especially the expression in the adult heart, lung and kidney. However, there are several differences between these two receptors, including the expression of the novel receptor in the embryonic lung as a large transcript and in the fetal liver as a small, alternate spliced transcript. In addition, the novel receptor is not expressed at all in adult liver, in contrast to the phospholipase A2 receptor. These differences in expression pattern are consistent with differences in function between these two more widely expressed lectin-like receptors.

The cell types that express the novel endocytic lectin also give some clues as to its possible function. The relatively widespread transcription in adult tissues is consistent with endothelial expression, and the in situ hybridization analysis also supports this contention. Thus, even though the resolution of these experiments was insufficient to exactly identify the cell types expressing the novel lectin, it was often found in highly vascularized areas, including the lung, the kidney glomerulus, the choroid plexus and the bone marrow, to name a few. These data thus suggest that the novel lectin might function as a vascular carbohydrate binding protein. In contrast, other members of this family, including the macrophage mannose receptor and the DEC 205 receptor, appear to function as mediators of the immune system, and they are expressed on a small subset of adult immune system cells. However, because the embryo is in a sterile environment, it is unlikely that the currently described lectin is involved with this type of function, predominately because it is expressed throughout embryonic development beginning as early as day 7 of mouse development. One possible function that this lectin could perform in the vasculature might be to transport highly glycosylated proteins across the blood vessel. This could occur either from the lumenal side of the vessel to the extravascular space or in the other direction, depending upon the disposition of the lectin. If the lectin faced the lumenal side, it might thus function to transport highly glycosylated proteins from the vascular flow to the extravascular space. Consistent with its expression on the endothelium is its identification in various endothelial cell lines derived from the embryo. This type of possible function is, therefore, similar to that hypothesized for the macrophage mannose receptor expressed on endothelial cells of the liver. In this case, this receptor appears to mediate the clearance of desialated proteins from the bloodstream. The investigation of this hypothesis awaits the production of antibodies directed against this novel lectin, which will allow for a higher resolution analysis of the actual cellular localization of this protein in the embryo and adult. The high level of expression of the novel lectin in chondrocytes also suggests interesting possibilities. In contrast to endothelial cells, these cells are not directly exposed to the blood stream, so it is unlikely that the lectin binds to identical ligands in the case of these matrix-depositing cells. Expression of the lectin was detected in regions of mineralization, such as the sternal and tooth regions, as well as sites of cartilage deposition, such as the layrnx. These data suggest that the lectin might be involved with the synthesis of cartilage or other types of extracellular matrix produced by the chondrocytes. If the novel lectin described here is indeed found to be involved with endocytosis, than one possible function in chondrocytes might be the uptake of highly glycosylated precursor proteins that are degraded and utilized for extracellular matrix production. A contrasting possibility might be that the chondrocytes utilize this lectin to remodel the extracellular matrix by the endocytosis of highly glycosylated proteins.

Finally, the identification of the alternately spliced transcript that is specific for the human fetal liver is a very interesting result with potential implications to hematopoiesis, although the lack of a start codon in the current clone does not allow us to predict that this transcript encodes a protein. PCR analysis of this transcript clearly demonstrated that it was completely absent from the heart and lung, and northern blot analysis revealed a lack of signal for this or the full-length transcript in adult liver. Because fetal liver is a conspicuously important site of hematopoiesis in the embryo, this result suggests that this transcript may in some way be involved with fetal hematopoiesis. The possible endothelial localization of the transcript also suggests a possible involvement in blood cell production, since previous work has suggested that endothelial cells appear to be involved with the expansion of progenitor cells in the embryo. Interestingly, the spliced transcript lacks the first two lectin domains which, by sequence homology with the mannose binding protein, may be involved with carbohydrate recognition. Thus, it is likely that, if this transcript encodes a protein product, that this form of the lectin might utilize other regions of the extracellular portion of the protein for novel receptor-ligand interactions.

In summary, the data reported here provide evidence for a novel member of the endocytic type C lectin family. This glycoprotein appears to be expressed in a wide variety of tissues in the embryo and adult, and it is transcribed by chondrocytes and, possibly, endothelial cells.

All documents cited throughout the specification as well as the references cited therein are hereby expressly incorporated by reference. While the present invention is illustrated with reference to specific embodiments, the invention is not so limited. It will be understood that further modifications and variations are possible without diverting from the overall concept of the invention. All such modifications are intended to be within the scope of the present invention.

What is claimed is:

1. An isolated type C lectin polypeptide comprising an amino acid sequence selected from the group consisting of:
   (a) amino acid residues 37 to 1393 of the amino acid sequence of FIGS. 2A–H (SEQ ID NO:2);
   (b) amino acid residues 37 to 1393 of the amino acid sequence of FIG. 9 (SEQ ID NO:4);
   (c) amino acid residues 37 to 174 of the amino acid sequence of FIGS. 2A–H (SEQ ID NO:2);
   (d) amino acid residues 37 to 174 of the amino acid sequence of FIG. 9 (SEQ ID NO:4);
   (e) amino acid residues 175 to 229 of the amino acid sequence of FIGS. 2A–H (SEQ ID NO:2);
   (f) amino acid residues 175 to 229 of the amino acid sequence of FIG. 9 (SEQ ID NO:4);
   (g) amino acid residues 234 to 360 of the amino acid sequence of FIGS. 2A–H (SEQ ID NO:2);
   (h) amino acid residues 234 to 360 of the amino acid sequence of FIG. 9 (SEQ ID NO:4);
   (i) amino acid residues 381 to 507 of the amino acid sequence of FIGS. 2A–H (SEQ ID NO:2);
   (j) amino acid residues 381 to 507 of the amino acid sequence of FIG. 9 (SEQ ID NO:4);
   (k) amino acid residues 520 to 645 of the amino acid sequence of FIGS. 2A–H (SEQ ID NO:2);

(l) amino acid residues 520 to 645 of the amino acid sequence of FIG. 9 (SEQ ID NO:4);

(m) amino acid residues 667 to 809 of the amino acid sequence of FIGS. 2A–H (SEQ ID NO:2);

(n) amino acid residues 667 to 809 of the amino acid sequence of FIG. 9 (SEQ ID NO:4);

(o) amino acid residues 824 to 951 of the amino acid sequence of FIGS. 2A–H (SEQ ID NO:2);

(p) amino acid residues 824 to 951 of the amino acid sequence of FIG. 9 (SEQ ID NO:4);

(q) amino acid residues 970 to 1108 of the amino acid sequence of FIGS. 2A–H (SEQ ID NO:2);

(r) amino acid residues 970 to 1108 of the amino acid sequence of FIG. 9 (SEQ ID NO:4);

(s) amino acid residues 1110 to 1243 of the amino acid sequence of FIGS. 2A–H (SEQ ID NO:2);

(t) amino acid residues 1110 to 1243 of the amino acid sequence of FIG. 9 (SEQ ID NO:4);

(u) amino acid residues 1259 to 1393 of the amino acid sequence of FIGS. 2A–H (SEQ ID NO:2);

(v) amino acid residues 1259 to 1393 of the amino acid sequence of FIG. 9 (SEQ ID NO:4);

wherein the polypeptides of (a) and (b) are capable of binding to a carbohydrate residue and the polypeptides of (c) to (v) are useful for the production of antibodies capable of binding to the polypeptides of (a) and (b).

2. The type C lectin polypeptide of claim 1 which is unglycosylated.

3. The type C lectin polypeptide of claim 1 which comprises amino acid residues 37 to 1393 of the amino acid sequence of FIGS. 2A–H (SEQ ID NO:2).

4. The type C lectin polypeptide of claim 1 which comprises amino acid residues 37 to 1393 of the amino acid sequence of FIG. 9 (SEQ ID NO:4).

5. The type C lectin polypeptide of claim 1 which comprises amino acid residues 37 to 174 of the amino acid sequence of FIGS. 2A–H (SEQ ID NO:2).

6. The type C lectin polypeptide of claim 1 which comprises amino acid residues 37 to 174 of the amino acid sequence of FIG. 9 (SEQ ID NO:4).

7. The type C lectin polypeptide of claim 1 which comprises amino acid residues 175 to 229 of the amino acid sequence of FIGS. 2A–H (SEQ ID NO:2).

8. The type C lectin polypeptide of claim 1 which comprises amino acid residues 175 to 229 of the amino acid sequence of FIG. 9 (SEQ ID NO:4).

9. The type C lectin polypeptide of claim 1 which comprises amino acid residues 234 to 360 of the amino acid sequence of FIGS. 2A–H (SEQ ID NO:2).

10. The type C lectin polypeptide of claim 1 which comprises amino acid residues 234 to 360 of the amino acid sequence of FIG. 9 (SEQ ID NO:4).

11. The type C lectin polypeptide of claim 1 which comprises amino acid residues 381 to 507 of the amino acid sequence of FIGS. 2A–H (SEQ ID NO:2).

12. The type C lectin polypeptide of claim 1 which comprises amino acid residues 381 to 507 of the amino acid sequence of FIG. 9 (SEQ ID NO:4).

13. The type C lectin polypeptide of claim 1 which comprises amino acid residues 520 to 645 of the amino acid sequence of FIGS. 2A–H (SEQ ID NO:2).

14. The type C lectin polypeptide of claim 1 which comprises amino acid residues 520 to 645 of the amino acid sequence of FIG. 9 (SEQ ID NO:4).

15. The type C lectin polypeptide of claim 1 which comprises amino acid residues 667 to 809 of the amino acid sequence of FIGS. 2A–H (SEQ ID NO:2).

16. The type C lectin polypeptide of claim 1 which comprises amino acid residues 667 to 809 of the amino acid sequence of FIG. 9 (SEQ ID NO:4).

17. The type C lectin polypeptide of claim 1 which comprises amino acid residues 824 to 951 of the amino acid sequence of FIGS. 2A–H (SEQ ID NO:2).

18. The type C lectin polypeptide of claim 1 which comprises amino acid residues 824 to 951 of the amino acid sequence of FIG. 9 (SEQ ID NO:4).

19. The type C lectin polypeptide of claim 1 which comprises amino acid residues 970 to 1108 of the amino acid sequence of FIGS. 2A–H (SEQ ID NO:2).

20. The type C lectin polypeptide of claim 1 which comprises amino acid residues 970 to 1108 of the amino acid sequence of FIG. 9 (SEQ ID NO:4).

21. The type C lectin polypeptide of claim 1 which comprises amino acid residues 1110 to 1243 of the amino acid sequence of FIGS. 2A–H (SEQ ID NO:2).

22. The type C lectin polypeptide of claim 1 which comprises amino acid residues 1110 to 1243 of the amino acid sequence of FIG. 9 (SEQ ID NO:4).

23. The type C lectin polypeptide of claim 1 which comprises amino acid residues 1259 to 1393 of the amino acid sequence of FIGS. 2A–H (SEQ ID NO:2).

24. The type C lectin polypeptide of claim 1 which comprises amino acid residues 1259 to 1393 of the amino acid sequence of FIG. 9 (SEQ ID NO:4).

25. An isolated nucleic acid encoding the type C lectin polypeptide of claim 1.

26. A vector comprising the nucleic acid molecule of claim 25 operably linked to control sequences recognized by a host cell transformed with the vector.

27. A host cell transformed with the vector of claim 26.

28. The host cell of claim 27 which is a mammalian cell.

29. The host cell of claim 28 which is a chinese hamster ovary cell.

30. A process for producing the type C lectin polypeptide of claim 1 which comprises transforming a host cell with nucleic acid encoding said type C lectin polypeptide, culturing the transformed cell and recovering said type C lectin polypeptide from the cell culture.

31. The process of claim 30 wherein said type C lectin polypeptide is secreted into the culture medium and recovered from the culture medium.

32. An immunoadhesin comprising an amino acid sequence of a type C lectin polypeptide according to claim 1 fused to an immunoglobulin sequence.

33. The immunoadhesin of claim 32, wherein said immunoglobulin sequence is an immunoglobulin heavy chain constant domain sequence.

34. The immunoadhesin of claim 32, wherein said immunoglobulin sequence is a constant domain sequence of an IgG-1, IgG-2 or IgG-3.

\* \* \* \* \*

UNITED STATES PATENT AND TRADEMARK OFFICE
CERTIFICATE OF CORRECTION

PATENT NO. : 6,117,977

DATED : September 12, 2000

INVENTOR(S) : Lasky et al.

It is certified that error appears in the above-identified patent and that said Letters Patent is hereby corrected as shown below:

On the title page,
[63] Continuation of application No. 08/637,021, Apr. 24, 1996, abandoned.

[60] Provisional application No.60/052,524, Apr. 24, 1996.

Signed and Sealed this

Twenty-fourth Day of April, 2001

Attest:

NICHOLAS P. GODICI

Attesting Officer     *Acting Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 4588 base pairs
      (B) TYPE: Nucleic Acid
      (C) STRANDEDNESS: Single
      (D) TOPOLOGY: Linear (xi) SEQUENCE DESCRIPTION: SEQ ID NO:1:

```
TGCGATCCCC TCGCCGGCGG TCATCCGAGC ACAGCGCTAG GGCTGTCTCT              50

GCACGCAGCC CTGCCGTGCG CCCTCCGTAC TCTCGTCCTC CGAGCGCCGC             100
```

-continued

```
AGGGATGGTA CCCATCCGAC CTGCCCTCGC GCCCTGGCCT CGTCACCTGC          150

TGCGCTGCGT CTTGCTTCTC GGGGGACTGC GTCTCGGCCA CCCGGCGGAC          200

TCCGCCGCCG CCCTCCTGGA GCCTGATGTC TTCCTCATCT TCAGCCAGGG          250

GATGCAGGGC TGTCTGGAGG CCCAGGGTGT GCAGGTCCGA GTCACCCCAT          300

TCTGCAATGC CAGTCTCCCT GCCCAGCGCT GGAAGTGGGT CTCCCGGAAC          350

CGACTCTTCA ACCTGGGTGC CACACAGTGC CTGGGTACAG GCTGGCCAGT          400

CACCAACACC ACAGTTTCCT TGGGCATGTA TGAGTGTGAC AGAGAGGCCT          450

TGAGTCTTCG GATGGCAGTG TCGTACACTA GGGGACCAGT TGTCCCTGCT          500

TCTGGGGGCT CGTGCAAGCA ATGCATCCAA GCCTGGCACC TGGAGCGCGG          550

TGACCAGACC CGCAGTGGCC ATTGGAACAT CTATGGCAGT GAAGAAGACC          600

TATGTGCTCG ACCTTACTAT GAGGTCTACA CCATCCAGGG AAAACTCACAC         650

GGAAAGCCGT GCACTATCCC CTTCAAATAC GACAACCAGT GGTTCCACGG          700

CTGCACCAGC ACTGGCAGAG AAGATGGGCA CCTGTGGTGT GCCACCACCC          750

AGGACTACGG CAAAGATGAG CGCTGGGGCT TCTGCCCCAT CAAGAGTAAC          800

GACTGTGAGA CCTTCTGGGA CAAAGACCAG CTGACTGACA GCTGTTACCA          850

GTTTAACTTC CAATCCACAC TGTCCTGGAG GGAGGCCTGG GCCAGCTGCG          900

AGCAGCAGGG TGCAGACTTG CTGAGTATCA CGGAGATCCA CGAGCAGACC          950

TACATCAACG GGCTCCTCAC GGGCTACAGC TCCACGCTAT GGATTGGCCT         1000

TAATGACCTG GATACCAGTG GAGGCTGGCA GTGGTCAGAC AACTCACCCC         1050

TCAAGTACCT CAACTGGGAG AGTGATCAGC CGGACAACCC AGGTGAGGAG         1100

AACTGTGGAG TGATCCGGAC TGAGTCCTCA GGCGGCTGGC AGAACCATGA         1150

CTGCAGCATC GCCCTGCCCT ATGTTTGCAA GAAGAAACCC AACGCTACGG         1200

TCGAGCCCAT CCAGCCAGAC CGGTGGACCA ATGTCAAGGT GGAATGTGAC         1250

CCCAGCTGGC AGCCCTTCCA GGGCCACTGC TACCGCCTGC AGGCCGAGAA         1300

GCGCAGCTGG CAGGAGTCCA AGAGGGCGTG TCTGCGGGGT GGGGGTGACC         1350

TCCTTAGCAT CCACAGCATG GCTGAGCTGG AGTTCATCAC CAAACAGATC         1400

AAGCAAGAGG TGGAGGAGCT ATGGATTGGC CTCAATGATT TGAAACTGCA         1450

GATGAATTTT GAGTGGTCCG ACGGGAGCCT CGTGAGCTTC ACCCACTGGC         1500

ACCCCTTTGA GCCCAACAAC TTTCGTGACA GCCTGGAGGA CTGTGTCACC         1550

ATCTGGGGGC CGGAAGGACG CTGGAACGAC AGTCCCTGTA ACCAGTCCTT         1600

GCCATCCATT TGCAAGAAGG CAGGCCGGCT GAGCCAGGGC GCTGCGGAGG         1650

AGGACCACGA CTGCCGGAAG GGTTGGACGT GGCATAGCCC ATCCTGCTAC         1700

TGGCTGGGAG AGGACCAAGT GATCTACAGT GATGCCCGGC GCCTGTGTAC         1750

TGACCATGGC TCTCAGCTGG TCACCATCAC CAACAGGTTT GAGCAGGCCT         1800

TCGTCAGCAG CCTCATCTAT AACTGGGAGG CGAATACTT CTGGACAGCC          1850

CTGCAAGACC TCAACAGTAC TGGCTCCTTC CGTTGGCTCA GTGGGGATGA         1900

AGTCATATAT ACCCATTGGA ATCGAGACCA GCCTGGGTAC AGACGTGGAG         1950

GCTGTGTGGC TCTGGCCACT GGCAGTGCCA TGGGACTGTG GGAGGTGAAG         2000

AACTGCACAT CGTTCCGGGC TCGCTACATC TGCCGACAGA GCCTGGGCAC         2050

ACCGGTCACA CCAGAGCTGC CTGGGCCAGA CCCCACGCCC AGCCTCACTG         2100
```

| | |
|---|---|
| GCTCCTGTCC CCAGGGCTGG GTCTCAGACC CCAAACTCCG ACACTGCTAT | 2150 |
| AAGGTGTTCA GCTCAGAGCG GCTGCAGGAG AAGAAGAGTT GGATCCAGGC | 2200 |
| CCTGGGGGTC TGCCGGGAGT TGGGGGCCCA GCTGCTGAGT CTGGCCAGCT | 2250 |
| ATGAGGAGGA GCACTTTGTG GCCCACATGC TCAACAAGAT CTTTGGTGAG | 2300 |
| TCAGAGCCTG AGAGCCATGA GCAGCACTGG TTTTGGATTG GCCTGAACCG | 2350 |
| CAGAGACCCT AGAGAGGGTC ACAGCTGGCG CTGGAGCGAC GGTCTAGGGT | 2400 |
| TTTCCTACCA CAATTTTGCC CGGAGCCGAC ATGATGACGA TGATATCCGA | 2450 |
| GGCTGTGCAG TGCTGGACCT GGCCTCCCTG CAGTGGGTAC CCATGCAGTG | 2500 |
| CCAGACGCAG CTTGACTGGA TCTGCAAGAT CCCTAGAGGT GTGGATGTGC | 2550 |
| GGGAACCAGA CATTGGTCGA CAAGGCCGTC TGGAGTGGGT ACGCTTTCAG | 2600 |
| GAGGCCGAGT ACAAGTTTTT TGAGCACCAC TCCTCGTGGG CGCAGGCACA | 2650 |
| GCGCATCTGC ACCTGGTTCC AGGCAGATCT GACCTCCGTT CACAGCCAAG | 2700 |
| CAGAACTGGG CTTCCTGGGG CAAAACCTGC AGAAGCTGTC CTCAGACCAG | 2750 |
| GAGCAGCACT GGTGGATCGG CCTGCACACC TTGGAGAGTG ACGGACGCTT | 2800 |
| CAGGTGGACA GATGGTTCTA TTATAAACTT CATCTCTTGG GCACCGGGAA | 2850 |
| AACCTAGACC CATTGGCAAG GACAAGAAGT GTGTATACAT GACAGCCAGA | 2900 |
| CAAGAGGACT GGGGGGACCA GAGGTGCCAT ACGGCTTTGC CCTACATCTG | 2950 |
| TAAGCGCAGC AATAGCTCTG GAGAGACTCA GCCCCAAGAC TTGCCACCTT | 3000 |
| CAGCCTTAGG AGGCTGCCCC TCCGGTTGGA ACCAGTTCCT CAATAAGTGT | 3050 |
| TTCCGAATCC AGGGCCAGGA CCCCCAGGAC AGGGTGAAAT GGTCAGAGGC | 3100 |
| ACAGTTCTCC TGTGAACAGC AAGAAGCCCA GCTGGTCACC ATTGCAAACC | 3150 |
| CCTTAGAGCA AGCATTTATC ACAGCCAGCC TCCCCAACGT GACCTTTGAC | 3200 |
| CTTTGGATTG GCCTGCATGC CTCTCAGAGG GACTTCCAGT GGATTGAACA | 3250 |
| AGAACCCCTG CTCTATACCA ACTGGGCACC AGGAGAGCCC TCTGGCCCCA | 3300 |
| GCCCTGCTCC CAGTGGCACC AAGCCGACCA GCTGTGCGGT GATCCTGCAC | 3350 |
| AGCCCCTCAG CCCACTTCAC TGGCCGCTGG GATGATCGGA GCTGCACAGA | 3400 |
| GGAGACGCAT GGCTTCATCT GCCAGAAGGG CACAGACCCC TCGCTAAGCC | 3450 |
| CATCCCCAGC AGCAACACCC CCTGCCCCGG GCGCTGAGCT CTCCTATCTC | 3500 |
| AACCACACCT TCCGGCTGCT GCAGAAGCCA CTGCGCTGGA AAGATGCTCT | 3550 |
| CCTGCTGTGT GAGAGCCGAA ATGCCAGCCT GGCACACGTG CCCGATCCCT | 3600 |
| ACACACAAGC CTTCCTCACA CAGGCTGCAC GGGGGCTGCA AACACCACTG | 3650 |
| TGGATCGGGC TGGCCAGTGA GGAGGGCTCA CGGAGGTATT CCTGGCTCTC | 3700 |
| AGAGGAGCCT CTGAATTATG TGAGCTGGCA AGATGAGGAG CCCCAGCACT | 3750 |
| CGGGAGGCTG TGCCTACGTG GATGTGGATG GAACCTGGCG CACCACCAGC | 3800 |
| TGTGATACCA AGCTGCAGGG GGCAGTGTGT GGGGTGAGCA GGGGGCCCCC | 3850 |
| ACCCCGAAGG ATAAACTACC GTGGCAGCTG TCCTCAGGGC TTGGCTGACT | 3900 |
| CGTCCTGGAT TCCCTTCAGG GAGCATTGCT ATTCTTTCCA CATGGAGGTG | 3950 |
| CTGTTGGGCC ACAAGGAGGC GCTGCAGCGC TGTCAGAAAG CTGGTGGGAC | 4000 |
| GGTTCTGTCC ATTCTTGATG AGATGGAGAA TGTGTTTGTC TGGGAGCACC | 4050 |

-continued

```
TGCAGACAGC TGAAGCCCAA AGTCGAGGTG CCTGGTTGGG CATGAACTTC            4100

AACCCCAAAG GAGGCACGCT GGTCTGGCAA GACAACACAG CTGTGAACTA            4150

TTCTAACTGG GGGCCCCCTG GCCTGGGCCC TAGCATGCTA AGCCACAACA            4200

GCTGCTACTG GATCCAGAGC AGCAGCGGAC TGTGGCGCCC CGGGGCTTGT            4250

ACCAACATCA CCATGGGAGT TGTCTGCAAG CTCCCTAGAG TGGAAGAGAA            4300

CAGCTTCTTG CCATCAGCAG CCCTCCCCGA GAGCCCGGTT GCCCTGGTGG            4350

TGGTGCTGAC AGCGGTGCTG CTCCTCCTGG CCTTGATGAC GGCAGCCCTC            4400

ATCCTCTACC GGCGCCGACA GAGTGCGGAG CGTGGGTCCT TCGAGGGGGC            4450

CCGCTACAGT CGCAGCAGCC ACTCTGGCCC CGCAGAGGCC ACCGAGAAGA            4500

ACATTCTGGT GTCTGACATG GAAATGAACG AACAGCAAGA ATAGAGCCAA            4550

GGGCGTGGTC GGGGTGGAGC CAAAGCGGGG GAGGCAGG                         4588
```

(2) INFORMATION FOR SEQ ID NO:2:

(i) SEQUENCE CHARACTERISTICS:
        (A) LENGTH: 1479 amino acids
        (B) TYPE: Amino Acid
        (D) TOPOLOGY: Linear (xi) SEQUENCE DESCRIPTION: SEQ ID NO:2:

```
Met Val Pro Ile Arg Pro Ala Leu Ala Pro Trp Pro Arg His Leu
 1               5                  10                  15

Leu Arg Cys Val Leu Leu Leu Gly Gly Leu Arg Leu Gly His Pro
                20                  25                  30

Ala Asp Ser Ala Ala Ala Leu Leu Glu Pro Asp Val Phe Leu Ile
                35                  40                  45

Phe Ser Gln Gly Met Gln Gly Cys Leu Glu Ala Gln Gly Val Gln
                50                  55                  60

Val Arg Val Thr Pro Val Cys Asn Ala Ser Leu Pro Ala Gln Arg
                65                  70                  75

Trp Lys Trp Val Ser Arg Asn Arg Leu Phe Asn Leu Gly Ala Thr
                80                  85                  90

Gln Cys Leu Gly Thr Gly Trp Pro Val Thr Asn Thr Thr Val Ser
                95                 100                 105

Leu Gly Met Tyr Glu Cys Asp Arg Glu Ala Leu Ser Leu Arg Met
               110                 115                 120

Ala Val Ser Tyr Thr Arg Gly Pro Val Val Pro Ala Ser Gly Gly
               125                 130                 135

Ser Cys Lys Gln Cys Ile Gln Ala Trp His Leu Glu Arg Gly Asp
               140                 145                 150

Gln Thr Arg Ser Gly His Trp Asn Ile Tyr Gly Ser Glu Glu Asp
               155                 160                 165

Leu Cys Ala Arg Pro Tyr Tyr Glu Val Tyr Thr Ile Gln Gly Asn
               170                 175                 180

Ser His Gly Lys Pro Cys Thr Ile Pro Phe Lys Tyr Asp Asn Gln
               185                 190                 195

Trp Phe His Gly Cys Thr Ser Thr Gly Arg Glu Asp Gly His Leu
               200                 205                 210

Trp Cys Ala Thr Thr Gln Asp Tyr Gly Lys Asp Glu Arg Trp Gly
               215                 220                 225

Phe Cys Pro Ile Lys Ser Asn Asp Cys Glu Thr Phe Trp Asp Lys
               230                 235                 240
```

-continued

```
Asp Gln Leu Thr Asp Ser Cys Tyr Gln Phe Asn Phe Gln Ser Thr
            245                 250                 255

Leu Ser Trp Arg Glu Ala Trp Ala Ser Cys Glu Gln Gln Gly Ala
            260                 265                 270

Asp Leu Leu Ser Ile Thr Glu Ile His Glu Gln Thr Tyr Ile Asn
            275                 280                 285

Gly Leu Leu Thr Gly Tyr Ser Ser Thr Leu Trp Ile Gly Leu Asn
            290                 295                 300

Asp Leu Asp Thr Ser Gly Gly Trp Gln Trp Ser Asp Asn Ser Pro
            305                 310                 315

Leu Lys Tyr Leu Asn Trp Glu Ser Asp Gln Pro Asp Asn Pro Gly
            320                 325                 330

Glu Glu Asn Cys Gly Val Ile Arg Thr Glu Ser Ser Gly Gly Trp
            335                 340                 345

Gln Asn His Asp Cys Ser Ile Ala Leu Pro Tyr Val Cys Lys Lys
            350                 355                 360

Lys Pro Asn Ala Thr Val Glu Pro Ile Gln Pro Asp Arg Trp Thr
            365                 370                 375

Asn Val Lys Val Glu Cys Asp Pro Ser Trp Gln Pro Phe Gln Gly
            380                 385                 390

His Cys Tyr Arg Leu Gln Ala Glu Lys Arg Ser Trp Gln Glu Ser
            395                 400                 405

Lys Arg Ala Cys Leu Arg Gly Gly Gly Asp Leu Leu Ser Ile His
            410                 415                 420

Ser Met Ala Glu Leu Glu Phe Ile Thr Lys Gln Ile Lys Gln Glu
            425                 430                 435

Val Glu Glu Leu Trp Ile Gly Leu Asn Asp Leu Lys Leu Gln Met
            440                 445                 450

Asn Phe Glu Trp Ser Asp Gly Ser Leu Val Ser Phe Thr His Trp
            455                 460                 465

His Pro Phe Glu Pro Asn Asn Phe Arg Asp Ser Leu Glu Asp Cys
            470                 475                 480

Val Thr Ile Trp Gly Pro Glu Gly Arg Trp Asn Asp Ser Pro Cys
            485                 490                 495

Asn Gln Ser Leu Pro Ser Ile Cys Lys Lys Ala Gly Arg Leu Ser
            500                 505                 510

Gln Gly Ala Ala Glu Glu Asp His Asp Cys Arg Lys Gly Trp Thr
            515                 520                 525

Trp His Ser Pro Ser Cys Tyr Trp Leu Gly Glu Asp Gln Val Ile
            530                 535                 540

Tyr Ser Asp Ala Arg Arg Leu Cys Thr Asp His Gly Ser Gln Leu
            545                 550                 555

Val Thr Ile Thr Asn Arg Phe Glu Gln Ala Phe Val Ser Ser Leu
            560                 565                 570

Ile Tyr Asn Trp Glu Gly Glu Tyr Phe Trp Thr Ala Leu Gln Asp
            575                 580                 585

Leu Asn Ser Thr Gly Ser Phe Arg Trp Leu Ser Gly Asp Glu Val
            590                 595                 600

Ile Tyr Thr His Trp Asn Arg Asp Gln Pro Gly Tyr Arg Arg Gly
            605                 610                 615

Gly Cys Val Ala Leu Ala Thr Gly Ser Ala Met Gly Leu Trp Glu
            620                 625                 630
```

-continued

```
Val Lys Asn Cys Thr Ser Phe Arg Ala Arg Tyr Ile Cys Arg Gln
            635                 640                 645

Ser Leu Gly Thr Pro Val Thr Pro Glu Leu Pro Gly Pro Asp Pro
            650                 655                 660

Thr Pro Ser Leu Thr Gly Ser Cys Pro Gln Gly Trp Val Ser Asp
            665                 670                 675

Pro Lys Leu Arg His Cys Tyr Lys Val Phe Ser Ser Glu Arg Leu
            680                 685                 690

Gln Glu Lys Lys Ser Trp Ile Gln Ala Leu Gly Val Cys Arg Glu
            695                 700                 705

Leu Gly Ala Gln Leu Leu Ser Leu Ala Ser Tyr Glu Glu His
            710                 715                 720

Phe Val Ala His Met Leu Asn Lys Ile Phe Gly Glu Ser Glu Pro
            725                 730                 735

Glu Ser His Glu Gln His Trp Phe Trp Ile Gly Leu Asn Arg Arg
            740                 745                 750

Asp Pro Arg Glu Gly His Ser Trp Arg Trp Ser Asp Gly Leu Gly
            755                 760                 765

Phe Ser Tyr His Asn Phe Ala Arg Ser Arg His Asp Asp Asp
            770                 775                 780

Ile Arg Gly Cys Ala Val Leu Asp Leu Ala Ser Leu Gln Trp Val
            785                 790                 795

Pro Met Gln Cys Gln Thr Gln Leu Asp Trp Ile Cys Lys Ile Pro
            800                 805                 810

Arg Gly Val Asp Val Arg Glu Pro Asp Ile Gly Arg Gln Gly Arg
            815                 820                 825

Leu Glu Trp Val Arg Phe Gln Glu Ala Glu Tyr Lys Phe Phe Glu
            830                 835                 840

His His Ser Ser Trp Ala Gln Ala Gln Arg Ile Cys Thr Trp Phe
            845                 850                 855

Gln Ala Asp Leu Thr Ser Val His Ser Gln Ala Glu Leu Gly Phe
            860                 865                 870

Leu Gly Gln Asn Leu Gln Lys Leu Ser Asp Gln Glu Gln His
            875                 880                 885

Trp Trp Ile Gly Leu His Thr Leu Glu Ser Asp Gly Arg Phe Arg
            890                 895                 900

Trp Thr Asp Gly Ser Ile Ile Asn Phe Ile Ser Trp Ala Pro Gly
            905                 910                 915

Lys Pro Arg Pro Ile Gly Lys Asp Lys Lys Cys Val Tyr Met Thr
            920                 925                 930

Ala Arg Gln Glu Asp Trp Gly Asp Gln Arg Cys His Thr Ala Leu
            935                 940                 945

Pro Tyr Ile Cys Lys Arg Ser Asn Ser Ser Gly Glu Thr Gln Pro
            950                 955                 960

Gln Asp Leu Pro Pro Ser Ala Leu Gly Gly Cys Pro Ser Gly Trp
            965                 970                 975

Asn Gln Phe Leu Asn Lys Cys Phe Arg Ile Gln Gly Gln Asp Pro
            980                 985                 990

Gln Asp Arg Val Lys Trp Ser Glu Ala Gln Phe Ser Cys Glu Gln
            995                 1000                1005

Gln Glu Ala Gln Leu Val Thr Ile Ala Asn Pro Leu Glu Gln Ala
               1010                1015                1020

Phe Ile Thr Ala Ser Leu Pro Asn Val Thr Phe Asp Leu Trp Ile
```

-continued

```
                    1025                1030                1035

Gly Leu His Ala Ser Gln Arg Asp Phe Gln Trp Ile Glu Gln Glu
                1040                1045                1050

Pro Leu Leu Tyr Thr Asn Trp Ala Pro Gly Glu Pro Ser Gly Pro
                1055                1060                1065

Ser Pro Ala Pro Ser Gly Thr Lys Pro Thr Ser Cys Ala Val Ile
                1070                1075                1080

Leu His Ser Pro Ser Ala His Phe Thr Gly Arg Trp Asp Asp Arg
                1085                1090                1095

Ser Cys Thr Glu Glu Thr His Gly Phe Ile Cys Gln Lys Gly Thr
                1100                1105                1110

Asp Pro Ser Leu Ser Pro Ser Pro Ala Ala Thr Pro Pro Ala Pro
                1115                1120                1125

Gly Ala Glu Leu Ser Tyr Leu Asn His Thr Phe Arg Leu Leu Gln
                1130                1135                1140

Lys Pro Leu Arg Trp Lys Asp Ala Leu Leu Leu Cys Glu Ser Arg
                1145                1150                1155

Asn Ala Ser Leu Ala His Val Pro Asp Pro Tyr Thr Gln Ala Phe
                1160                1165                1170

Leu Thr Gln Ala Ala Arg Gly Leu Gln Thr Pro Leu Trp Ile Gly
                1175                1180                1185

Leu Ala Ser Glu Glu Gly Ser Arg Arg Tyr Ser Trp Leu Ser Glu
                1190                1195                1200

Glu Pro Leu Asn Tyr Val Ser Trp Gln Asp Glu Glu Pro Gln His
                1205                1210                1215

Ser Gly Gly Cys Ala Tyr Val Asp Val Asp Gly Thr Trp Arg Thr
                1220                1225                1230

Thr Ser Cys Asp Thr Lys Leu Gln Gly Ala Val Cys Gly Val Ser
                1235                1240                1245

Arg Gly Pro Pro Pro Arg Arg Ile Asn Tyr Arg Gly Ser Cys Pro
                1250                1255                1260

Gln Gly Leu Ala Asp Ser Ser Trp Ile Pro Phe Arg Glu His Cys
                1265                1270                1275

Tyr Ser Phe His Met Glu Val Leu Leu Gly His Lys Glu Ala Leu
                1280                1285                1290

Gln Arg Cys Gln Lys Ala Gly Gly Thr Val Leu Ser Ile Leu Asp
                1295                1300                1305

Glu Met Glu Asn Val Phe Val Trp Glu His Leu Gln Thr Ala Glu
                1310                1315                1320

Ala Gln Ser Arg Gly Ala Trp Leu Gly Met Asn Phe Asn Pro Lys
                1325                1330                1335

Gly Gly Thr Leu Val Trp Gln Asp Asn Thr Ala Val Asn Tyr Ser
                1340                1345                1350

Asn Trp Gly Pro Pro Gly Leu Gly Pro Ser Met Leu Ser His Asn
                1355                1360                1365

Ser Cys Tyr Trp Ile Gln Ser Ser Ser Gly Leu Trp Arg Pro Gly
                1370                1375                1380

Ala Cys Thr Asn Ile Thr Met Gly Val Val Cys Lys Leu Pro Arg
                1385                1390                1395

Val Glu Glu Asn Ser Phe Leu Pro Ser Ala Ala Leu Pro Glu Ser
                1400                1405                1410

Pro Val Ala Leu Val Val Val Leu Thr Ala Val Leu Leu Leu Leu
                1415                1420                1425
```

```
Ala Leu Met Thr Ala Ala Leu Ile Leu Tyr Arg Arg Arg Gln Ser
            1430                1435                1440

Ala Glu Arg Gly Ser Phe Glu Gly Ala Arg Tyr Ser Arg Ser Ser
            1445                1450                1455

His Ser Gly Pro Ala Glu Ala Thr Glu Lys Asn Ile Leu Val Ser
            1460                1465                1470

Asp Met Glu Met Asn Glu Gln Gln Glu
            1475            1479

(2) INFORMATION FOR SEQ ID NO:3:

(i) SEQUENCE CHARACTERISTICS:
        (A) LENGTH: 4771 base pairs
        (B) TYPE: Nucleic Acid
        (C) STRANDEDNESS: Single
        (D) TOPOLOGY: Linear (xi) SEQUENCE DESCRIPTION: SEQ ID NO:3:
```

| | | |
|---|---|---|
| AGCGCCGCAG GGATGGTACC CATCCGACCT GCCCTCGCGC CCTGGCCTCG | | 50 |
| TCACCTGCTG CGCTGCGTCC TGCTCCTCGG GTGCCTGCAC CTCGGCCGTC | | 100 |
| CCGGCGCCCC TGGGGACGCC GCCCTCCCGG AACCCAACAT CTTCCTCATC | | 150 |
| TTCAGCCATG GACTGCAGGG CTGCCTGGAG GCCCAGGGCG GGCAGGTCAG | | 200 |
| AGCCACCCCG GCTTGCAATA CCAGCCTCCC TGCCCAGCGC TGGAAGTGGG | | 250 |
| TCTCCCGAAA CCGGCTATTC AACCTGGGTA CCATGCAGTG CCTGGGCACA | | 300 |
| GGCTGGCCAG GCACCAACAC CACGGCCTCC CTGGGCATGT ATGAGTGTGA | | 350 |
| CCGGGAAGCA CTGAATCTTC GCTGGCATTG TCGTACACTG GGTGACCAGC | | 400 |
| TGTCCTTGCT CCTGGGGACC CGCACCAGCA ACATATCCAA GCCTGGCACC | | 450 |
| CTTGAGCGTG TGACCAGAC CCGCAGTGGC CAGTGGCGCA TCTACGGCAG | | 500 |
| CGAGGAGGAC CTATGTGCTC TGCCCTACCA CGAGGTCTAC ACCATCCAGG | | 550 |
| GAAACTCCCA CGGAAAGCCG TGCACCATCC CCTTCAAATA TGACAACCAG | | 600 |
| TGGTTCCACG GCTGCACCAG CACGGGCCGC GAGGATGGTC ACCTGTGGTG | | 650 |
| TGCCACCACC CAGGACTACG GCAAAGACGA GCGCTGGGGC TTCTGCCCCA | | 700 |
| TCAAGAGTAA CGACTGCGAG ACCTTCTGGG ACAAGGACCA GCTGACTGAC | | 750 |
| AGCTGCTACC AGTTTAACTT CCAGTCCACG CTGTCGTGGA GGGAGGCCTG | | 800 |
| GGCCAGCTGC GAGCAGCAGG GTGCGGATCT GCTGAGCATC ACGGAGATCC | | 850 |
| ACGAGCAGAC CTACATCAAC GGCCTCCTCA CTGGGTACAG CTCCACCCTG | | 900 |
| TGGATCGGCT TGAATGACTT GGACACGAGC GGAGGCTGGC AGTGGTCGGA | | 950 |
| CAACTCGCCC CTCAAGTACC TCAACTGGGA GAGTGACCAG CCGGACAACC | | 1000 |
| CCAGTGAGGA GAACTGTGGA GTGATCCGCA CTGAGTCCTC GGGCGGCTGG | | 1050 |
| CAGAACCGTG ACTGCAGCAT CGCGCTGCCC TATGTGTGCA AGAAGAAGCC | | 1100 |
| CAACGCCACG GCCGAGCCCA CCCCTCCAGA CAGGTGGGCC AATGTGAAGG | | 1150 |
| TGGAGTGCGA GCCGAGCTGG CAGCCCTTCC AGGGCCACTG CTACCGCCTG | | 1200 |
| CAGGCCGAGA AGCGCAGCTG GCAGGAGTCC AAGAAGGCAT GTCTACGGGG | | 1250 |
| CGGTGGCGAC CTGGTCAGCA TCCACAGCAT GGCGGAGCTG GAATTCATCA | | 1300 |
| CCAAGCAGAT CAAGCAAGAG GTGGAGGAGC TGTGGATCGG CCTCAACGAT | | 1350 |
| TTGAAGCTGC AGATGAATTT TGAGTGGTCT GACGGGAGCC TTGTGAGCTT | | 1400 |

| | |
|---|---|
| CACCCACTGG CACCCCTTTG AGCCCAACAA CTTCCGGGAC AGTCTGGAGG | 1450 |
| ACTGTGTCAC CATCTGGGGC CCGGAAGGCC GCTGGAACGA CAGTCCCTGT | 1500 |
| AACCAGTCCT TGCCATCCAT CTGCAAGAAG GCAGGCCAGC TGAGCCAGGG | 1550 |
| GGCCGCCGAG GAGGACCATG GCTGCCGGAA GGGTTGGACG TGGCACAGCC | 1600 |
| CATCCTGCTA CTGGCTGGGA GAAGACCAAG TGACCTACAG TGAGGCCCGG | 1650 |
| CGCCTGTGCA CTGACCATGG CTCTCAGCTG GTCACCATCA CCAACAGGTT | 1700 |
| CGAGCAGGCC TTCGTCAGCA GCCTCATCTA CAACTGGGAG GGCGAGTACT | 1750 |
| TCTGGACGGC CCTGCAGGAC CTCAACAGCA CCGGCTCCTT CTTCTGGCTC | 1800 |
| AGTGGGGATG AAGTCATGTA CACCCACTGG AACCGGGACC AGCCCGGGTA | 1850 |
| CAGCCGTGGG GGCTGCGTGG CGCTGGCCAC TGGCAGCGCC ATGGGGCTGT | 1900 |
| GGGAGGTGAA GAACTGTACC TCGTTCCGGG CCCGCTACAT CTGCCGGCAG | 1950 |
| AGCCTGGGCA CTCCAGTGAC GCCGGAGCTG CCGGGGCCAG ATCCCACGCC | 2000 |
| CAGCCTCACT GGCTCCTGTC CCCAGGGCTG GGCCTCTGAC ACCAAACTCC | 2050 |
| GGTATTGCTA TAAGGTGTTC AGCTCAGAGC GGCTGCAGGA CAAGAAGAGC | 2100 |
| TGGGTCCAGG CCCAGGGGGC CTGCCAGGAG CTGGGGGCCC AGCTGCTGAG | 2150 |
| CCTGGCCAGC TACGAGGAGG AGCACTTTGT GGCCAACATG CTCAACAAGA | 2200 |
| TCTTCGGTGA ATCAGAACCC GAGATCCACG AGCAGCACTG GTTCTGGGTC | 2250 |
| GGCCTGAACC GTCGGGATCC CAGAGGGGGT CAGAGTTGGC GCAGGAGCGA | 2300 |
| CGGCGTAGGG TTCTCTTACC ACAATTTCGA CCGGAGCCGG CACGACGACG | 2350 |
| ACGACATCCG AGGCTGTGCG GTGCTGGACC TGGCCTCCCT GCAGTGGGTG | 2400 |
| GTCATGCAGT GCGACACACA GCTGGACTGG ATCTGCAAGA TCCCCAGAGG | 2450 |
| TACGGACGTG CGAGAGCCCG ACGACAGCCC TCAAGGCCGA CGGGAATGGC | 2500 |
| TGCGCTTCCA GGAGGCCGAG TACAAGTTCT TTGAGCACCA CTCCACGTGG | 2550 |
| GCGCAGGCGC AGCGCATCTG CACGTGGTTC CAGGCCGAGC TGACCTCCGT | 2600 |
| GCACAGCCAG GCGGAGCTAG ACTTCCTGAG CCACAACTTG CAGAAGTTCT | 2650 |
| CCCGGGCCCA GGAGCAGCAC TGGTGGATCG GCCTGCACAC CTCTGAGAGC | 2700 |
| GATGGGCGCT TCAGATGGAC AGATGGTTCC ATTATAAACT TCATCTCCTG | 2750 |
| GGCACCAGGC AAACCTCGGC CTGTCGGCAA GGACAAGAAG TGCGTGTACA | 2800 |
| TGACAGCCAG CCGAGAGGAC TGGGGGGACC AGAGGTGCCT GACAGCCTTG | 2850 |
| CCCTACATCT GCAAGCGCAG CAACGTCACC AAAGAAACGC AGCCCCCAGT | 2900 |
| CCTGCCAACT ACAGCCCTGG GGGCTGCCC CTCTGACTGG ATCCAGTTCC | 2950 |
| TCAACAAGTG TTTTCAGGTC CAGGGCCAGG AACCCCAGAG CCGGGTGAAG | 3000 |
| TGGTCAGAGG CACAGTTCTC CTGTGAACAG CAAGAGGCCC AGCTGGTCAC | 3050 |
| CATCACAAAC CCCTTAGAGC AAGCATTCAT CACAGCCAGC CTGCCCAATG | 3100 |
| TGACCTTTGA CCTTTGGATT GGCCTCCATG CCTCGCAGAG GGACTCCCAG | 3150 |
| TGGGTGGAGC AGGAGCCTTT GATGTATGCC AACTGGGCAC CTGGGGAGCC | 3200 |
| CTTTGGCCCT AGCCCTGCTC CCAGTGGCAA CAAACCGACC AGCTGTGCGG | 3250 |
| TGGTCCTGCA CAGCCCCTCA GCCCACTTCA CTGGCCGCTG GGACGATCGG | 3300 |
| AGCTGCACGG AGGAGACCCA TGGCTTCATC TGCCAGAAGG GCACGGACCC | 3350 |

```
CTCCCTGAGC CCGTCCCCAG CAGCGCTGCC CCCCGCCCCG GGCACTGAGC         3400

TCTCCTACCT CAACGGCACC TTCCGGCTGC TTCAGAAGCC GCTGCGCTGG         3450

CACGATGCCC TCCTGCTGTG TGAGAGCCAC AATGCCAGCC TGGCCTACGT         3500

GCCCGACCCC TACACCCAGG CCTTCCTCAC GCAGGCTGCC CGAGGGCTGC         3550

GCACGCCGCC CTGGATTGGG CTGGCTGGCG AGGAGGGCTC TCGGCGGTAC         3600

TCCTGGGTCT CAGAGGAGCC GCTGAACTAC GTGGGCTGGC AGGACGGGGA         3650

GCCGCAGCAG CCGGGGGGCT GTACCTACGT AGATGTGGAC GGGGCCTGGC         3700

GCACCACCAG CTGTGACACC AAGCTGCAGG GGCTGTGTG  TGGGGTTAGC         3750

AGTGGGCCCC CTCCTCCCCG AAGAATAAGC TACCATGGCA GCTGTCCCCA         3800

GGGACTGGCA GACTCCGCGT GGATTCCCTT CCGGGAGCAC TGCTATTCTT         3850

TCCACATGGA GCTGCTGCTG GGCCACAAGG AGGCGCGACA GCGCTGCCAG         3900

AGAGCGGGTG GGGCCGTCCT GTCTATCCTG GATGAGATGG AGAATGTGTT         3950

TGTCTGGGAG CACCTGCAGA GCTATGAGGG CCAGAGTCGG GGCGCCTGGC         4000

TGGGCATGAA CTTCAACCCC AAAGGAGGCA CTCTGGTCTG GCAGGACAAC         4050

ACAGCTGTGA ACTACTCCAA CTGGGGGCCC CCGGGCTTGG GCCCCAGCAT         4100

GCTGAGCCAC AACAGCTGCT ACTGGATTCA GAGCAACAGC GGGCTATGGC         4150

GCCCCGGCGC TTGCACCAAC ATCACCATGG GTGTCGTCTG CAAGCTTCCT         4200

CGTGCTGAGC GGAGCAGCTT CTCCCCATCA GCGCTTCCAG AGAACCCAGC         4250

GGCCCTGGTG GTGGTGCTGA TGGCGGTGCT GCTGCTCCTG GCCTTGCTGA         4300

CCGCAGCCCT CATCCTTTAC CGGAGGCGCC AGAGCATCGA GCGCGGGGCC         4350

TTTGAGGGTG CCCGCTACAG CCGCAGCAGC TCCAGCCCCA CCGAGGCCAC         4400

CGAGAAGAAC ATCCTGGTGT CAGACATGGA AATGAATGAG CAGCAAGAAT         4450

AGAGCCAGGC GCGTGGGCAG GGCCAGGGCG GGAGGAGCTG GGGAGCTGGG         4500

GCCCTGGGTC AGTCTGGCCC CCCACCAGCT GCCTGTCCAG TTGGCCTATG         4550

GAAGGGTGCC CTTGGGAGTC GCTGTTGGGA GCCGGAGCTG GGCAGAGCCT         4600

GGGCTGGTGG GGGCCGGAAT TCGCCCTATA GTGAGTCGTA TTACAATTCA         4650

CTGGCCGTCG TTTTACAACG TCGTGACTGG GAAAACCTGG CGTTACCAAC         4700

TTAATCGCCT TGCAGCACAT CCCCCTTTCG CCAGCTGGCG TAATAGCGAA         4750

GAGGCCGCAC CGATCGCCTT C                                      4771
```

(2) INFORMATION FOR SEQ ID NO:4:

(i) SEQUENCE CHARACTERISTICS:
        (A) LENGTH: 1479 amino acids
        (B) TYPE: Amino Acid
        (D) TOPOLOGY: Linear (xi) SEQUENCE DESCRIPTION: SEQ ID NO:4:

```
Met Val Pro Ile Arg Pro Ala Leu Ala Pro Trp Pro Arg His Leu
 1               5                  10                  15

Leu Arg Cys Val Leu Leu Gly Cys Leu His Leu Gly Arg Pro
                20                  25                  30

Gly Ala Pro Gly Asp Ala Ala Leu Pro Glu Pro Asn Ile Phe Leu
                35                  40                  45

Ile Phe Ser His Gly Leu Gln Gly Cys Leu Glu Ala Gln Gly Gly
                50                  55                  60
```

```
Gln Val Arg Ala Thr Pro Ala Cys Asn Thr Ser Leu Pro Ala Gln
                 65                  70                  75

Arg Trp Lys Trp Val Ser Arg Asn Arg Leu Phe Asn Leu Gly Thr
             80                  85                  90

Met Gln Cys Leu Gly Thr Gly Trp Pro Gly Thr Asn Thr Thr Ala
             95                 100                 105

Ser Leu Gly Met Tyr Glu Cys Asp Arg Glu Ala Leu Asn Leu Arg
            110                 115                 120

Trp His Cys Arg Thr Leu Gly Asp Gln Leu Ser Leu Leu Leu Gly
            125                 130                 135

Thr Arg Thr Ser Asn Ile Ser Lys Pro Gly Thr Leu Glu Arg Gly
            140                 145                 150

Asp Gln Thr Arg Ser Gly Gln Trp Arg Ile Tyr Gly Ser Glu Glu
            155                 160                 165

Asp Leu Cys Ala Leu Pro Tyr His Glu Val Tyr Thr Ile Gln Gly
            170                 175                 180

Asn Ser His Gly Lys Pro Cys Thr Ile Pro Phe Lys Tyr Asp Asn
            185                 190                 195

Gln Trp Phe His Gly Cys Thr Ser Thr Gly Arg Glu Asp Gly His
            200                 205                 210

Leu Trp Cys Ala Thr Thr Gln Asp Tyr Gly Lys Asp Glu Arg Trp
            215                 220                 225

Gly Phe Cys Pro Ile Lys Ser Asn Asp Cys Glu Thr Phe Trp Asp
            230                 235                 240

Lys Asp Gln Leu Thr Asp Ser Cys Tyr Gln Phe Asn Phe Gln Ser
            245                 250                 255

Thr Leu Ser Trp Arg Glu Ala Trp Ala Ser Cys Glu Gln Gln Gly
            260                 265                 270

Ala Asp Leu Leu Ser Ile Thr Glu Ile His Glu Gln Thr Tyr Ile
            275                 280                 285

Asn Gly Leu Leu Thr Gly Tyr Ser Ser Thr Leu Trp Ile Gly Leu
            290                 295                 300

Asn Asp Leu Asp Thr Ser Gly Gly Trp Gln Trp Ser Asp Asn Ser
            305                 310                 315

Pro Leu Lys Tyr Leu Asn Trp Glu Ser Asp Gln Pro Asp Asn Pro
            320                 325                 330

Ser Glu Glu Asn Cys Gly Val Ile Arg Thr Glu Ser Ser Gly Gly
            335                 340                 345

Trp Gln Asn Arg Asp Cys Ser Ile Ala Leu Pro Tyr Val Cys Lys
            350                 355                 360

Lys Lys Pro Asn Ala Thr Ala Glu Pro Thr Pro Pro Asp Arg Trp
            365                 370                 375

Ala Asn Val Lys Val Glu Cys Glu Pro Ser Trp Gln Pro Phe Gln
            380                 385                 390

Gly His Cys Tyr Arg Leu Gln Ala Glu Lys Arg Ser Trp Gln Glu
            395                 400                 405

Ser Lys Lys Ala Cys Leu Arg Gly Gly Gly Asp Leu Val Ser Ile
            410                 415                 420

His Ser Met Ala Glu Leu Glu Phe Ile Thr Lys Gln Ile Lys Gln
            425                 430                 435

Glu Val Glu Glu Leu Trp Ile Gly Leu Asn Asp Leu Lys Leu Gln
            440                 445                 450
```

-continued

```
Met Asn Phe Glu Trp Ser Asp Gly Ser Leu Val Ser Phe Thr His
            455                 460                 465

Trp His Pro Phe Glu Pro Asn Asn Phe Arg Asp Ser Leu Glu Asp
            470                 475                 480

Cys Val Thr Ile Trp Gly Pro Glu Gly Arg Trp Asn Asp Ser Pro
            485                 490                 495

Cys Asn Gln Ser Leu Pro Ser Ile Cys Lys Lys Ala Gly Gln Leu
            500                 505                 510

Ser Gln Gly Ala Ala Glu Glu Asp His Gly Cys Arg Lys Gly Trp
            515                 520                 525

Thr Trp His Ser Pro Ser Cys Tyr Trp Leu Gly Glu Asp Gln Val
            530                 535                 540

Thr Tyr Ser Glu Ala Arg Arg Leu Cys Thr Asp His Gly Ser Gln
            545                 550                 555

Leu Val Thr Ile Thr Asn Arg Phe Glu Gln Ala Phe Val Ser Ser
            560                 565                 570

Leu Ile Tyr Asn Trp Glu Gly Glu Tyr Phe Trp Thr Ala Leu Gln
            575                 580                 585

Asp Leu Asn Ser Thr Gly Ser Phe Phe Trp Leu Ser Gly Asp Glu
            590                 595                 600

Val Met Tyr Thr His Trp Asn Arg Asp Gln Pro Gly Tyr Ser Arg
            605                 610                 615

Gly Gly Cys Val Ala Leu Ala Thr Gly Ser Ala Met Gly Leu Trp
            620                 625                 630

Glu Val Lys Asn Cys Thr Ser Phe Arg Ala Arg Tyr Ile Cys Arg
            635                 640                 645

Gln Ser Leu Gly Thr Pro Val Thr Pro Glu Leu Pro Gly Pro Asp
            650                 655                 660

Pro Thr Pro Ser Leu Thr Gly Ser Cys Pro Gln Gly Trp Ala Ser
            665                 670                 675

Asp Thr Lys Leu Arg Tyr Cys Tyr Lys Val Phe Ser Ser Glu Arg
            680                 685                 690

Leu Gln Asp Lys Lys Ser Trp Val Gln Ala Gln Gly Ala Cys Gln
            695                 700                 705

Glu Leu Gly Ala Gln Leu Leu Ser Leu Ala Ser Tyr Glu Glu Glu
            710                 715                 720

His Phe Val Ala Asn Met Leu Asn Lys Ile Phe Gly Glu Ser Glu
            725                 730                 735

Pro Glu Ile His Glu Gln His Trp Phe Trp Val Gly Leu Asn Arg
            740                 745                 750

Arg Asp Pro Arg Gly Gly Gln Ser Trp Arg Arg Ser Asp Gly Val
            755                 760                 765

Gly Phe Ser Tyr His Asn Phe Asp Arg Ser Arg His Asp Asp Asp
            770                 775                 780

Asp Ile Arg Gly Cys Ala Val Leu Asp Leu Ala Ser Leu Gln Trp
            785                 790                 795

Val Val Met Gln Cys Asp Thr Gln Leu Asp Trp Ile Cys Lys Ile
            800                 805                 810

Pro Arg Gly Thr Asp Val Arg Glu Pro Asp Ser Pro Gln Gly
            815                 820                 825

Arg Arg Glu Trp Leu Arg Phe Gln Glu Ala Glu Tyr Lys Phe Phe
            830                 835                 840

Glu His His Ser Thr Trp Ala Gln Ala Gln Arg Ile Cys Thr Trp
```

-continued

```
                845                 850                 855
Phe Gln Ala Glu Leu Thr Ser Val His Ser Gln Ala Glu Leu Asp
            860                 865                 870
Phe Leu Ser His Asn Leu Gln Lys Phe Ser Arg Ala Gln Glu Gln
            875                 880                 885
His Trp Trp Ile Gly Leu His Thr Ser Glu Ser Asp Gly Arg Phe
            890                 895                 900
Arg Trp Thr Asp Gly Ser Ile Ile Asn Phe Ile Ser Trp Ala Pro
            905                 910                 915
Gly Lys Pro Arg Pro Val Gly Lys Asp Lys Cys Val Tyr Met
            920                 925                 930
Thr Ala Ser Arg Glu Asp Trp Gly Asp Gln Arg Cys Leu Thr Ala
            935                 940                 945
Leu Pro Tyr Ile Cys Lys Arg Ser Asn Val Thr Lys Glu Thr Gln
            950                 955                 960
Pro Pro Val Leu Pro Thr Thr Ala Leu Gly Gly Cys Pro Ser Asp
            965                 970                 975
Trp Ile Gln Phe Leu Asn Lys Cys Phe Gln Val Gln Gly Gln Glu
            980                 985                 990
Pro Gln Ser Arg Val Lys Trp Ser Glu Ala Gln Phe Ser Cys Glu
            995                1000                1005
Gln Gln Glu Ala Gln Leu Val Thr Ile Thr Asn Pro Leu Glu Gln
           1010                1015                1020
Ala Phe Ile Thr Ala Ser Leu Pro Asn Val Thr Phe Asp Leu Trp
           1025                1030                1035
Ile Gly Leu His Ala Ser Gln Arg Asp Ser Gln Trp Val Glu Gln
           1040                1045                1050
Glu Pro Leu Met Tyr Ala Asn Trp Ala Pro Gly Glu Pro Phe Gly
           1055                1060                1065
Pro Ser Pro Ala Pro Ser Gly Asn Lys Pro Thr Ser Cys Ala Val
           1070                1075                1080
Val Leu His Ser Pro Ser Ala His Phe Thr Gly Arg Trp Asp Asp
           1085                1090                1095
Arg Ser Cys Thr Glu Glu Thr His Gly Phe Ile Cys Gln Lys Gly
           1100                1105                1110
Thr Asp Pro Ser Leu Ser Pro Ser Pro Ala Ala Leu Pro Pro Ala
           1115                1120                1125
Pro Gly Thr Glu Leu Ser Tyr Leu Asn Gly Thr Phe Arg Leu Leu
           1130                1135                1140
Gln Lys Pro Leu Arg Trp His Asp Ala Leu Leu Leu Cys Glu Ser
           1145                1150                1155
His Asn Ala Ser Leu Ala Tyr Val Pro Asp Pro Tyr Thr Gln Ala
           1160                1165                1170
Phe Leu Thr Gln Ala Ala Arg Gly Leu Arg Thr Pro Pro Trp Ile
           1175                1180                1185
Gly Leu Ala Gly Glu Glu Gly Ser Arg Arg Tyr Ser Trp Val Ser
           1190                1195                1200
Glu Glu Pro Leu Asn Tyr Val Gly Trp Gln Asp Gly Glu Pro Gln
           1205                1210                1215
Gln Pro Gly Gly Cys Thr Tyr Val Asp Val Asp Gly Ala Trp Arg
           1220                1225                1230
Thr Thr Ser Cys Asp Thr Lys Leu Gln Gly Ala Val Cys Gly Val
           1235                1240                1245
```

-continued

Ser Ser Gly Pro Pro Pro Arg Arg Ile Ser Tyr His Gly Ser
                1250                1255                1260

Cys Pro Gln Gly Leu Ala Asp Ser Ala Trp Ile Pro Phe Arg Glu
                1265                1270                1275

His Cys Tyr Ser Phe His Met Glu Leu Leu Gly His Lys Glu
                1280                1285                1290

Ala Arg Gln Arg Cys Gln Arg Ala Gly Gly Ala Val Leu Ser Ile
                1295                1300                1305

Leu Asp Glu Met Glu Asn Val Phe Val Trp Glu His Leu Gln Ser
                1310                1315                1320

Tyr Glu Gly Gln Ser Arg Gly Ala Trp Leu Gly Met Asn Phe Asn
                1325                1330                1335

Pro Lys Gly Gly Thr Leu Val Trp Gln Asp Asn Thr Ala Val Asn
                1340                1345                1350

Tyr Ser Asn Trp Gly Pro Pro Gly Leu Gly Pro Ser Met Leu Ser
                1355                1360                1365

His Asn Ser Cys Tyr Trp Ile Gln Ser Asn Ser Gly Leu Trp Arg
                1370                1375                1380

Pro Gly Ala Cys Thr Asn Ile Thr Met Gly Val Val Cys Lys Leu
                1385                1390                1395

Pro Arg Ala Glu Arg Ser Ser Phe Ser Pro Ser Ala Leu Pro Glu
                1400                1405                1410

Asn Pro Ala Ala Leu Val Val Val Leu Met Ala Val Leu Leu Leu
                1415                1420                1425

Leu Ala Leu Leu Thr Ala Ala Leu Ile Leu Tyr Arg Arg Arg Gln
                1430                1435                1440

Ser Ile Glu Arg Gly Ala Phe Glu Gly Ala Arg Tyr Ser Arg Ser
                1445                1450                1455

Ser Ser Ser Pro Thr Glu Ala Thr Glu Lys Asn Ile Leu Val Ser
                1460                1465                1470

Asp Met Glu Met Asn Glu Gln Gln Glu
                1475            1479

(2) INFORMATION FOR SEQ ID NO:5:

(i) SEQUENCE CHARACTERISTICS:
        (A) LENGTH: 1455 amino acids
        (B) TYPE: Amino Acid
        (D) TOPOLOGY: Linear (xi) SEQUENCE DESCRIPTION: SEQ ID NO:5:

Met Arg Leu Leu Leu Leu Ala Phe Ile Ser Val Ile Pro Val
 1               5                  10                  15

Ser Val Gln Leu Leu Asp Ala Arg Gln Phe Leu Ile Tyr Asn Glu
                20                  25                  30

Asp His Lys Arg Cys Val Asp Ala Leu Ser Ala Ile Ser Val Gln
                35                  40                  45

Thr Ala Thr Cys Asn Pro Glu Ala Glu Ser Gln Lys Phe Arg Trp
                50                  55                  60

Val Ser Asp Ser Gln Ile Met Ser Val Ala Phe Lys Leu Cys Leu
                65                  70                  75

Gly Val Pro Ser Lys Thr Asp Trp Ala Ser Val Thr Leu Tyr Ala
                80                  85                  90

Cys Asp Ser Lys Ser Glu Tyr Gln Lys Trp Glu Cys Lys Asn Asp
                95                  100                 105

-continued

```
Thr Leu Phe Gly Ile Lys Gly Thr Glu Leu Tyr Phe Asn Tyr Gly
            110                 115                 120

Asn Arg Gln Glu Lys Asn Ile Lys Leu Tyr Lys Gly Ser Gly Leu
            125                 130                 135

Trp Ser Arg Trp Lys Val Tyr Gly Thr Thr Asp Asp Leu Cys Ser
            140                 145                 150

Arg Gly Tyr Glu Ala Met Tyr Ser Leu Leu Gly Asn Ala Asn Gly
            155                 160                 165

Ala Val Cys Ala Phe Pro Phe Lys Phe Glu Asn Lys Trp Tyr Ala
            170                 175                 180

Asp Cys Thr Ser Ala Gly Arg Ser Asp Gly Trp Leu Trp Cys Gly
            185                 190                 195

Thr Thr Thr Asp Tyr Asp Lys Asp Lys Leu Phe Gly Phe Cys Pro
            200                 205                 210

Leu His Phe Glu Gly Ser Glu Arg Leu Trp Asn Lys Asp Pro Leu
            215                 220                 225

Thr Gly Ile Leu Tyr Gln Ile Asn Ser Lys Ser Ala Leu Thr Trp
            230                 235                 240

His Gln Ala Arg Ala Ser Cys Lys Gln Gln Asn Ala Asp Leu Leu
            245                 250                 255

Ser Val Thr Glu Ile His Glu Gln Met Tyr Leu Thr Gly Leu Thr
            260                 265                 270

Ser Ser Leu Ser Ser Gly Leu Trp Ile Gly Leu Asn Ser Leu Ser
            275                 280                 285

Val Arg Ser Gly Trp Gln Trp Ala Gly Gly Ser Pro Phe Arg Tyr
            290                 295                 300

Leu Asn Leu Pro Gly Ser Pro Ser Glu Pro Gly Lys Ser Cys
            305                 310                 315

Val Ser Leu Asn Pro Gly Lys Asn Ala Lys Trp Glu Asn Leu Glu
            320                 325                 330

Cys Val Gln Lys Leu Gly Tyr Ile Cys Lys Lys Gly Asn Asn Thr
            335                 340                 345

Leu Asn Pro Phe Ile Ile Pro Ser Ala Ser Asp Val Pro Thr Gly
            350                 355                 360

Cys Pro Asn Gln Trp Trp Pro Tyr Ala Gly His Cys Tyr Arg Ile
            365                 370                 375

His Arg Glu Glu Lys Lys Ile Gln Lys Tyr Ala Leu Gln Ala Cys
            380                 385                 390

Arg Lys Glu Gly Gly Asp Leu Ala Ser Ile His Ser Ile Glu Glu
            395                 400                 405

Phe Asp Phe Ile Phe Ser Gln Leu Gly Tyr Glu Pro Asn Asp Glu
            410                 415                 420

Leu Trp Ile Gly Leu Asn Asp Ile Lys Ile Gln Met Tyr Phe Glu
            425                 430                 435

Trp Ser Asp Gly Thr Pro Val Thr Phe Thr Lys Trp Leu Pro Gly
            440                 445                 450

Glu Pro Ser His Glu Asn Asn Arg Gln Glu Asp Cys Val Val Met
            455                 460                 465

Lys Gly Lys Asp Gly Tyr Trp Ala Asp Arg Ala Cys Glu Gln Pro
            470                 475                 480

Leu Gly Tyr Ile Cys Lys Met Val Ser Gln Ser His Ala Val Val
            485                 490                 495
```

-continued

```
Pro Glu Gly Ala Asp Lys Gly Cys Arg Lys Gly Trp Lys Arg His
            500                 505                 510

Gly Phe Tyr Cys Tyr Leu Ile Gly Ser Thr Leu Ser Thr Phe Thr
        515                 520                 525

Asp Ala Asn His Thr Cys Thr Asn Glu Lys Ala Tyr Leu Thr Thr
        530                 535                 540

Val Glu Asp Arg Tyr Glu Gln Ala Phe Leu Thr Ser Leu Val Gly
        545                 550                 555

Leu Arg Pro Glu Lys Tyr Phe Trp Thr Gly Leu Ser Asp Val Gln
        560                 565                 570

Asn Lys Gly Thr Phe Arg Trp Thr Val Asp Glu Gln Val Gln Phe
        575                 580                 585

Thr His Trp Asn Ala Asp Met Pro Gly Arg Lys Ala Gly Cys Val
        590                 595                 600

Ala Met Lys Thr Gly Val Ala Gly Gly Leu Trp Asp Val Leu Ser
        605                 610                 615

Cys Glu Glu Lys Ala Lys Phe Val Cys Lys His Trp Ala Glu Gly
        620                 625                 630

Val Thr Arg Pro Pro Glu Pro Thr Thr Thr Pro Glu Pro Lys Cys
        635                 640                 645

Pro Glu Asn Trp Gly Thr Thr Ser Lys Thr Ser Met Cys Phe Lys
        650                 655                 660

Leu Tyr Ala Lys Gly Lys His Glu Lys Lys Thr Trp Phe Glu Ser
        665                 670                 675

Arg Asp Phe Cys Lys Ala Ile Gly Gly Glu Leu Ala Ser Ile Lys
        680                 685                 690

Ser Lys Asp Glu Gln Gln Val Ile Trp Arg Leu Ile Thr Ser Ser
        695                 700                 705

Gly Ser Tyr His Glu Leu Phe Trp Leu Gly Leu Thr Tyr Gly Ser
        710                 715                 720

Pro Ser Glu Gly Phe Thr Trp Ser Asp Gly Ser Pro Val Ser Tyr
        725                 730                 735

Glu Asn Trp Ala Tyr Gly Glu Pro Asn Asn Tyr Gln Asn Val Glu
        740                 745                 750

Tyr Cys Gly Glu Leu Lys Gly Asp Pro Gly Met Ser Trp Asn Asp
        755                 760                 765

Ile Asn Cys Glu His Leu Asn Asn Trp Ile Cys Gln Ile Gln Lys
        770                 775                 780

Gly Lys Thr Leu Leu Pro Glu Pro Thr Pro Ala Pro Gln Asp Asn
        785                 790                 795

Pro Pro Val Thr Ala Asp Gly Trp Val Ile Tyr Lys Asp Tyr Gln
        800                 805                 810

Tyr Tyr Phe Ser Lys Glu Lys Glu Thr Met Asp Asn Ala Arg Arg
        815                 820                 825

Phe Cys Lys Lys Asn Phe Gly Asp Leu Ala Thr Ile Lys Ser Glu
        830                 835                 840

Ser Glu Lys Lys Phe Leu Trp Lys Tyr Ile Asn Lys Asn Gly Gly
        845                 850                 855

Gln Ser Pro Tyr Phe Ile Gly Met Leu Ile Ser Met Asp Lys Lys
        860                 865                 870

Phe Ile Trp Met Asp Gly Ser Lys Val Asp Phe Val Ala Trp Ala
        875                 880                 885

Thr Gly Glu Pro Asn Phe Ala Asn Asp Asp Glu Asn Cys Val Thr
```

```
                        890                895                900
Met Tyr Thr Asn Ser Gly Phe Trp Asn Asp Ile Asn Cys Gly Tyr
                    905                910                915

Pro Asn Asn Phe Ile Cys Gln Arg His Asn Ser Ser Ile Asn Ala
                    920                925                930

Thr Ala Met Pro Thr Thr Pro Thr Thr Pro Gly Gly Cys Lys Glu
                    935                940                945

Gly Trp His Leu Tyr Lys Asn Lys Cys Phe Lys Ile Phe Gly Phe
                    950                955                960

Ala Asn Glu Glu Lys Lys Ser Trp Gln Asp Ala Arg Gln Ala Cys
                    965                970                975

Lys Gly Leu Lys Gly Asn Leu Val Ser Ile Glu Asn Ala Gln Glu
                    980                985                990

Gln Ala Phe Val Thr Tyr His Met Arg Asp Ser Thr Phe Asn Ala
                    995               1000               1005

Trp Thr Gly Leu Asn Asp Ile Asn Ala Glu His Met Phe Leu Trp
                   1010               1015               1020

Thr Ala Gly Gln Gly Val His Tyr Thr Asn Trp Gly Lys Gly Tyr
                   1025               1030               1035

Pro Gly Gly Arg Arg Ser Ser Leu Ser Tyr Glu Asp Ala Asp Cys
                   1040               1045               1050

Val Val Val Ile Gly Gly Asn Ser Arg Glu Ala Gly Thr Trp Met
                   1055               1060               1065

Asp Asp Thr Cys Asp Ser Lys Gln Gly Tyr Ile Cys Gln Thr Gln
                   1070               1075               1080

Thr Asp Pro Ser Leu Pro Val Ser Pro Thr Thr Pro Lys Asp
                   1085               1090               1095

Gly Phe Val Thr Tyr Gly Lys Ser Ser Tyr Ser Leu Met Lys Leu
                   1100               1105               1110

Lys Leu Pro Trp His Glu Ala Gly Thr Tyr Cys Lys Asp His Thr
                   1115               1120               1125

Ser Leu Leu Ala Ser Ile Leu Asp Pro Tyr Ser Asn Ala Phe Ala
                   1130               1135               1140

Trp Met Lys Met His Pro Phe Asn Val Pro Ile Trp Ile Ala Leu
                   1145               1150               1155

Asn Ser Asn Leu Thr Asn Asn Glu Tyr Thr Trp Thr Asp Arg Trp
                   1160               1165               1170

Arg Val Arg Tyr Thr Asn Trp Gly Ala Asp Glu Pro Lys Leu Lys
                   1175               1180               1185

Ser Ala Cys Val Tyr Met Asp Val Asp Gly Tyr Trp Arg Thr Ser
                   1190               1195               1200

Tyr Cys Asn Glu Ser Phe Tyr Phe Leu Cys Lys Lys Ser Asp Glu
                   1205               1210               1215

Ile Pro Ala Thr Glu Pro Pro Gln Leu Pro Gly Lys Cys Pro Glu
                   1220               1225               1230

Ser Glu Gln Thr Ala Trp Ile Pro Phe Tyr Gly His Cys Tyr Tyr
                   1235               1240               1245

Phe Glu Ser Ser Phe Thr Arg Ser Trp Gly Gln Ala Ser Leu Glu
                   1250               1255               1260

Cys Leu Arg Met Gly Ala Ser Leu Val Ser Ile Glu Thr Ala Ala
                   1265               1270               1275

Glu Ser Ser Phe Leu Ser Tyr Arg Val Glu Pro Leu Lys Ser Lys
                   1280               1285               1290
```

```
Thr Asn Phe Trp Ile Gly Met Phe Arg Asn Val Glu Gly Lys Trp
            1295                1300                1305

Leu Trp Leu Asn Asp Asn Pro Val Ser Phe Val Asn Trp Lys Thr
            1310                1315                1320

Gly Asp Pro Ser Gly Glu Arg Asn Asp Cys Val Val Leu Ala Ser
            1325                1330                1335

Ser Ser Gly Leu Trp Asn Asn Ile His Cys Ser Ser Tyr Lys Gly
            1340                1345                1350

Phe Ile Cys Lys Met Pro Lys Ile Ile Asp Pro Val Thr Thr His
            1355                1360                1365

Ser Ser Ile Thr Thr Lys Ala Asp Gln Arg Lys Met Asp Pro Gln
            1370                1375                1380

Pro Lys Gly Ser Ser Lys Ala Ala Gly Val Val Thr Val Val Leu
            1385                1390                1395

Leu Ile Val Ile Gly Ala Gly Val Ala Ala Tyr Phe Phe Tyr Lys
            1400                1405                1410

Lys Arg His Ala Leu His Ile Pro Gln Glu Ala Thr Phe Glu Asn
            1415                1420                1425

Thr Leu Tyr Phe Asn Ser Asn Leu Ser Pro Gly Thr Ser Asp Thr
            1430                1435                1440

Lys Asp Leu Met Gly Asn Ile Glu Gln Asn Glu His Ala Ile Ile
            1445                1450                1455

(2) INFORMATION FOR SEQ ID NO:6:

(i) SEQUENCE CHARACTERISTICS:
        (A) LENGTH: 1449 amino acids
        (B) TYPE: Amino Acid
        (D) TOPOLOGY: Linear (xi) SEQUENCE DESCRIPTION: SEQ ID NO:6:

Met Arg Thr Gly Arg Val Thr Pro Gly Leu Ala Ala Gly Leu Leu
 1               5                  10                  15

Leu Leu Leu Leu Arg Ser Phe Gly Leu Val Glu Pro Ser Glu Ser
                20                  25                  30

Ser Gly Asn Asp Pro Phe Thr Ile Val His Glu Asn Thr Gly Lys
                35                  40                  45

Cys Ile Gln Pro Leu Ser Asp Trp Val Ala Gln Asp Cys Ser
                50                  55                  60

Gly Thr Asn Asn Met Leu Trp Lys Trp Val Ser Gln His Arg Leu
                65                  70                  75

Phe His Leu Glu Ser Gln Lys Cys Leu Gly Leu Asp Ile Thr Lys
                80                  85                  90

Ala Thr Asp Asn Leu Arg Met Phe Ser Cys Asp Ser Thr Val Met
                95                  100                 105

Leu Trp Trp Lys Cys Glu His His Ser Leu Tyr Thr Ala Ala Gln
                110                 115                 120

Tyr Arg Leu Ala Leu Lys Asp Gly Tyr Ala Val Ala Asn Thr Asn
                125                 130                 135

Thr Ser Asp Val Trp Lys Lys Gly Gly Ser Glu Glu Asn Leu Cys
                140                 145                 150

Ala Gln Pro Tyr His Glu Ile Tyr Thr Arg Asp Gly Asn Ser Tyr
                155                 160                 165

Gly Arg Pro Cys Glu Phe Pro Phe Leu Ile Gly Glu Thr Trp Tyr
                170                 175                 180
```

```
His Asp Cys Ile His Asp Glu Asp His Ser Gly Pro Trp Cys Ala
            185                 190                 195
Thr Thr Leu Ser Tyr Glu Tyr Asp Gln Lys Trp Gly Ile Cys Leu
            200                 205                 210
Leu Pro Glu Ser Gly Cys Glu Gly Asn Trp Glu Lys Asn Glu Gln
            215                 220                 225
Ile Gly Ser Cys Tyr Gln Phe Asn Asn Gln Glu Ile Leu Ser Trp
            230                 235                 240
Lys Glu Ala Tyr Val Ser Cys Gln Asn Gln Gly Ala Asp Leu Leu
            245                 250                 255
Ser Ile His Ser Ala Ala Glu Leu Ala Tyr Ile Thr Gly Lys Glu
            260                 265                 270
Asp Ile Ala Arg Leu Val Trp Leu Gly Leu Asn Gln Leu Tyr Ser
            275                 280                 285
Ala Arg Gly Trp Glu Trp Ser Asp Phe Arg Pro Leu Lys Phe Leu
            290                 295                 300
Asn Trp Asp Pro Gly Thr Pro Val Ala Pro Val Ile Gly Gly Ser
            305                 310                 315
Ser Cys Ala Arg Met Asp Thr Glu Ser Gly Leu Trp Gln Ser Val
            320                 325                 330
Ser Cys Glu Ser Gln Gln Pro Tyr Val Cys Lys Lys Pro Leu Asn
            335                 340                 345
Asn Thr Leu Glu Leu Pro Asp Val Trp Thr Tyr Thr Asp Thr His
            350                 355                 360
Cys His Val Gly Trp Leu Pro Asn Asn Gly Phe Cys Tyr Leu Leu
            365                 370                 375
Ala Asn Glu Ser Ser Ser Trp Asp Ala Ala His Leu Lys Cys Lys
            380                 385                 390
Ala Phe Gly Ala Asp Leu Ile Ser Met His Ser Leu Ala Asp Val
            395                 400                 405
Glu Val Val Val Thr Lys Leu His Asn Gly Asp Val Lys Lys Glu
            410                 415                 420
Ile Trp Thr Gly Leu Lys Asn Thr Asn Ser Pro Ala Leu Phe Gln
            425                 430                 435
Trp Ser Asp Gly Thr Glu Val Thr Leu Thr Tyr Trp Asn Glu Asn
            440                 445                 450
Glu Pro Ser Val Pro Phe Asn Lys Thr Pro Asn Cys Val Ser Tyr
            455                 460                 465
Leu Gly Lys Leu Gly Gln Trp Lys Val Gln Ser Cys Glu Lys Lys
            470                 475                 480
Leu Arg Tyr Val Cys Lys Lys Gly Glu Ile Thr Lys Asp Ala
            485                 490                 495
Glu Ser Asp Lys Leu Cys Pro Pro Asp Glu Gly Trp Lys Arg His
            500                 505                 510
Gly Glu Thr Cys Tyr Lys Ile Tyr Glu Lys Glu Ala Pro Phe Gly
            515                 520                 525
Thr Asn Cys Asn Leu Thr Ile Thr Ser Arg Phe Glu Gln Glu Phe
            530                 535                 540
Leu Asn Tyr Met Met Lys Asn Tyr Asp Lys Ser Leu Arg Lys Tyr
            545                 550                 555
Phe Trp Thr Gly Leu Arg Asp Pro Asp Ser Arg Gly Glu Tyr Ser
            560                 565                 570
```

-continued

```
Trp Ala Val Ala Gln Gly Val Lys Gln Ala Val Thr Phe Ser Asn
                575                 580                 585

Trp Asn Phe Leu Glu Pro Ala Ser Pro Gly Gly Cys Val Ala Met
                590                 595                 600

Ser Thr Gly Lys Thr Leu Gly Lys Trp Glu Val Lys Asn Cys Arg
                605                 610                 615

Ser Phe Arg Ala Leu Ser Ile Cys Lys Lys Val Ser Glu Pro Gln
                620                 625                 630

Glu Pro Glu Glu Ala Pro Lys Pro Asp Asp Pro Cys Pro Glu
                635                 640                 645

Gly Trp His Thr Phe Pro Ser Ser Leu Ser Cys Tyr Lys Val Phe
                650                 655                 660

His Ile Glu Arg Ile Val Arg Lys Arg Asn Trp Glu Glu Ala Glu
                665                 670                 675

Arg Phe Cys Gln Ala Leu Gly Ala His Leu Pro Ser Phe Ser Arg
                680                 685                 690

Arg Glu Glu Ile Lys Asp Phe Val His Leu Leu Lys Asp Gln Phe
                695                 700                 705

Ser Gly Gln Arg Trp Leu Trp Ile Gly Leu Asn Lys Arg Ser Pro
                710                 715                 720

Asp Leu Gln Gly Ser Trp Gln Trp Ser Asp Arg Thr Pro Val Ser
                725                 730                 735

Ala Val Met Met Glu Pro Glu Phe Gln Gln Asp Phe Asp Ile Arg
                740                 745                 750

Asp Cys Ala Ala Ile Lys Val Leu Asp Val Pro Trp Arg Arg Val
                755                 760                 765

Trp His Leu Tyr Glu Asp Lys Asp Tyr Ala Tyr Trp Lys Pro Phe
                770                 775                 780

Ala Cys Asp Ala Lys Leu Glu Trp Val Cys Gln Ile Pro Lys Gly
                785                 790                 795

Ser Thr Pro Gln Met Pro Asp Trp Tyr Asn Pro Glu Arg Thr Gly
                800                 805                 810

Ile His Gly Pro Pro Val Ile Ile Glu Gly Ser Glu Tyr Trp Phe
                815                 820                 825

Val Ala Asp Pro His Leu Asn Tyr Glu Glu Ala Val Leu Tyr Cys
                830                 835                 840

Ala Ser Asn His Ser Phe Leu Ala Thr Ile Thr Ser Phe Thr Gly
                845                 850                 855

Leu Lys Ala Ile Lys Asn Lys Leu Ala Asn Ile Ser Gly Glu Glu
                860                 865                 870

Gln Lys Trp Trp Val Lys Thr Ser Glu Asn Pro Ile Asp Arg Tyr
                875                 880                 885

Phe Leu Gly Ser Arg Arg Arg Leu Trp His His Phe Pro Met Thr
                890                 895                 900

Phe Gly Asp Glu Cys Leu His Met Ser Ala Lys Thr Trp Leu Val
                905                 910                 915

Asp Leu Ser Lys Arg Ala Asp Cys Asn Ala Lys Leu Pro Phe Ile
                920                 925                 930

Cys Glu Arg Tyr Asn Val Ser Ser Leu Glu Lys Tyr Ser Pro Asp
                935                 940                 945

Pro Ala Ala Lys Val Gln Cys Thr Glu Lys Trp Ile Pro Phe Gln
                950                 955                 960

Asn Lys Cys Phe Leu Lys Val Asn Ser Gly Pro Val Thr Phe Ser
```

-continued

```
                    965                 970                 975
Gln Ala Ser Gly Ile Cys His Ser Tyr Gly Gly Thr Leu Pro Ser
                980                 985                 990
Val Leu Ser Arg Gly Glu Gln Asp Phe Ile Ile Ser Leu Leu Pro
                995                1000                1005
Glu Met Glu Ala Ser Leu Trp Ile Gly Leu Arg Trp Thr Ala Tyr
               1010                1015                1020
Glu Arg Ile Asn Arg Trp Thr Asp Asn Arg Glu Leu Thr Tyr Ser
               1025                1030                1035
Asn Phe His Pro Leu Leu Val Gly Arg Arg Leu Ser Ile Pro Thr
               1040                1045                1050
Asn Phe Phe Asp Asp Glu Ser His Phe His Cys Ala Leu Ile Leu
               1055                1060                1065
Asn Leu Lys Lys Ser Pro Leu Thr Gly Thr Trp Asn Phe Thr Ser
               1070                1075                1080
Cys Ser Glu Arg His Ser Leu Ser Leu Cys Gln Lys Tyr Ser Glu
               1085                1090                1095
Thr Glu Asp Gly Gln Pro Trp Glu Asn Thr Ser Lys Thr Val Lys
               1100                1105                1110
Tyr Leu Asn Asn Leu Tyr Lys Ile Ile Ser Lys Pro Leu Thr Trp
               1115                1120                1125
His Gly Ala Leu Lys Glu Cys Met Lys Glu Lys Met Arg Leu Val
               1130                1135                1140
Ser Ile Thr Asp Pro Tyr Gln Gln Ala Phe Leu Ala Val Gln Ala
               1145                1150                1155
Thr Leu Arg Asn Ser Ser Phe Trp Ile Gly Leu Ser Ser Gln Asp
               1160                1165                1170
Asp Glu Leu Asn Phe Gly Trp Ser Asp Gly Lys Arg Leu Gln Phe
               1175                1180                1185
Ser Asn Trp Ala Gly Ser Asn Glu Gln Leu Asp Asp Cys Val Ile
               1190                1195                1200
Leu Asp Thr Asp Gly Phe Trp Lys Thr Ala Asp Cys Asp Asp Asn
               1205                1210                1215
Gln Pro Gly Ala Ile Cys Tyr Tyr Pro Gly Asn Glu Thr Glu Glu
               1220                1225                1230
Glu Val Arg Ala Leu Asp Thr Ala Lys Cys Pro Ser Pro Val Gln
               1235                1240                1245
Ser Thr Pro Trp Ile Pro Phe Gln Asn Ser Cys Tyr Asn Phe Met
               1250                1255                1260
Ile Thr Asn Asn Arg His Lys Thr Val Thr Pro Glu Glu Val Gln
               1265                1270                1275
Ser Thr Cys Glu Lys Leu His Pro Lys Ala His Ser Leu Ser Ile
               1280                1285                1290
Arg Asn Glu Glu Glu Asn Thr Phe Val Val Glu Gln Leu Leu Tyr
               1295                1300                1305
Phe Asn Tyr Ile Ala Ser Trp Val Met Leu Gly Ile Thr Tyr Glu
               1310                1315                1320
Asn Asn Ser Leu Met Trp Phe Asp Lys Thr Ala Leu Ser Tyr Thr
               1325                1330                1335
His Trp Arg Thr Gly Arg Pro Thr Val Lys Asn Gly Lys Phe Leu
               1340                1345                1350
Ala Gly Leu Ser Thr Asp Gly Phe Trp Asp Ile Gln Ser Phe Asn
               1355                1360                1365
```

```
Val Ile Glu Glu Thr Leu His Phe Tyr Gln His Ser Ile Ser Ala
              1370                1375                1380

Cys Lys Ile Glu Met Val Asp Tyr Glu Asp Lys His Asn Tyr Thr
              1385                1390                1395

Gly Ile Ala Ile Leu Phe Ala Val Leu Cys Leu Leu Gly Leu Ile
              1400                1405                1410

Ser Leu Ala Ile Trp Phe Leu Leu Gln Arg Ser His Ile Arg Trp
              1415                1420                1425

Thr Gly Phe Ser Ser Val Arg Tyr Glu His Gly Thr Asn Glu Asp
              1430                1435                1440

Glu Val Met Leu Pro Ser Phe His Asp
              1445            1449

(2) INFORMATION FOR SEQ ID NO:7:

(i) SEQUENCE CHARACTERISTICS:
        (A) LENGTH: 1487 amino acids
        (B) TYPE: Amino Acid
        (D) TOPOLOGY: Linear (xi) SEQUENCE DESCRIPTION: SEQ ID NO:7:

Met Val Gln Trp Leu Ala Met Leu Gln Leu Leu Trp Leu Gln Gln
 1               5                  10                  15

Leu Leu Leu Leu Gly Ile His Gln Gly Ile Ala Gln Asp Leu Thr
                20                  25                  30

His Ile Gln Glu Pro Ser Leu Glu Trp Arg Asp Lys Gly Ile Phe
                35                  40                  45

Ile Ile Gln Ser Glu Ser Leu Lys Thr Cys Ile Gln Ala Gly Lys
                50                  55                  60

Ser Val Leu Thr Leu Glu Asn Cys Lys Gln Pro Asn Glu His Met
                65                  70                  75

Leu Trp Lys Trp Val Ser Asp Asp His Leu Phe Asn Val Gly Gly
                80                  85                  90

Ser Gly Cys Leu Gly Leu Asn Ile Ser Ala Leu Glu Gln Pro Leu
                95                  100                 105

Lys Leu Tyr Glu Cys Asp Ser Thr Leu Ile Ser Leu Arg Trp His
                110                 115                 120

Cys Asp Arg Lys Met Ile Glu Gly Pro Leu Gln Tyr Lys Val Gln
                125                 130                 135

Val Lys Ser Asp Asn Thr Val Ala Arg Lys Gln Ile His Arg
                140                 145                 150

Trp Ile Ala Tyr Thr Ser Ser Gly Gly Asp Ile Cys Glu His Pro
                155                 160                 165

Ser Arg Asp Leu Tyr Thr Leu Lys Gly Asn Ala His Gly Met Pro
                170                 175                 180

Cys Val Phe Pro Phe Gln Phe Lys Gly His Trp His His Asp Cys
                185                 190                 195

Ile Arg Glu Gly Gln Lys Glu His Leu Leu Trp Cys Ala Thr Thr
                200                 205                 210

Ser Arg Tyr Glu Glu Asp Glu Lys Trp Gly Phe Cys Pro Asp Pro
                215                 220                 225

Thr Ser Met Lys Val Phe Cys Asp Ala Thr Trp Gln Arg Asn Gly
                230                 235                 240

Ser Ser Arg Ile Cys Tyr Gln Phe Asn Leu Leu Ser Ser Leu Ser
                245                 250                 255
```

-continued

```
Trp Asn Gln Ala His Ser Ser Cys Leu Met Gln Gly Gly Ala Leu
            260                 265                 270

Leu Ser Ile Ala Asp Glu Asp Glu Asp Phe Ile Arg Lys His
            275                 280                 285

Leu Ser Lys Val Val Lys Glu Val Trp Ile Gly Leu Asn Gln Leu
            290                 295                 300

Asp Glu Lys Ala Gly Trp Gln Trp Ser Asp Gly Thr Pro Leu Ser
            305                 310                 315

Tyr Leu Asn Trp Ser Gln Glu Ile Thr Pro Gly Pro Phe Val Glu
            320                 325                 330

His His Cys Gly Thr Leu Glu Val Val Ser Ala Ala Trp Arg Ser
            335                 340                 345

Arg Asp Cys Glu Ser Thr Leu Pro Tyr Ile Cys Lys Arg Asp Leu
            350                 355                 360

Asn His Thr Ala Gln Gly Ile Leu Glu Lys Asp Ser Trp Lys Tyr
            365                 370                 375

His Ala Thr His Cys Asp Pro Asp Trp Thr Pro Phe Asn Arg Lys
            380                 385                 390

Cys Tyr Lys Leu Lys Lys Asp Arg Lys Ser Trp Leu Gly Ala Leu
            395                 400                 405

His Ser Cys Gln Ser Asn Asp Ser Val Leu Met Asp Val Ala Ser
            410                 415                 420

Leu Ala Glu Val Glu Phe Leu Val Ser Leu Leu Arg Asp Glu Asn
            425                 430                 435

Ala Ser Glu Thr Trp Ile Gly Leu Ser Ser Asn Lys Ile Pro Val
            440                 445                 450

Ser Phe Glu Trp Ser Ser Gly Ser Ser Val Ile Phe Thr Asn Trp
            455                 460                 465

Tyr Pro Leu Glu Pro Arg Ile Leu Pro Asn Arg Arg Gln Leu Cys
            470                 475                 480

Val Ser Ala Glu Glu Ser Asp Gly Arg Trp Lys Val Lys Asp Cys
            485                 490                 495

Lys Glu Arg Leu Phe Tyr Ile Cys Lys Lys Ala Gly Gln Val Pro
            500                 505                 510

Ala Asp Glu Gln Ser Gly Cys Pro Ala Gly Trp Glu Arg His Gly
            515                 520                 525

Arg Phe Cys Tyr Lys Ile Asp Thr Val Leu Arg Ser Phe Glu Glu
            530                 535                 540

Ala Ser Ser Gly Tyr Tyr Cys Ser Pro Ala Leu Leu Thr Ile Thr
            545                 550                 555

Ser Arg Phe Glu Gln Ala Phe Ile Thr Ser Leu Ile Ser Ser Val
            560                 565                 570

Ala Glu Lys Asp Ser Tyr Phe Trp Ile Ala Leu Gln Asp Gln Asn
            575                 580                 585

Asn Thr Gly Glu Tyr Thr Trp Lys Thr Val Gly Gln Arg Glu Pro
            590                 595                 600

Val Gln Tyr Thr Tyr Trp Asn Thr Arg Gln Pro Ser Asn Arg Gly
            605                 610                 615

Gly Cys Val Val Val Arg Gly Gly Ser Ser Leu Gly Arg Trp Glu
            620                 625                 630

Val Lys Asp Cys Ser Asp Phe Lys Ala Met Ser Leu Cys Lys Thr
            635                 640                 645
```

-continued

```
Pro Val Lys Ile Trp Glu Lys Thr Glu Leu Glu Glu Arg Trp Pro
            650                 655                 660

Phe His Pro Cys Tyr Met Asp Trp Glu Ser Ala Thr Gly Leu Ala
            665                 670                 675

Ser Cys Phe Lys Val Phe His Ser Glu Lys Val Leu Met Lys Arg
            680                 685                 690

Ser Trp Arg Glu Ala Glu Ala Phe Cys Glu Glu Phe Gly Ala His
            695                 700                 705

Leu Ala Ser Phe Ala His Ile Glu Glu Asn Phe Val Asn Glu
            710                 715                 720

Leu Leu His Ser Lys Phe Asn Trp Thr Gln Glu Arg Gln Phe Trp
            725                 730                 735

Ile Gly Phe Asn Arg Arg Asn Pro Leu Asn Ala Gly Ser Trp Ala
            740                 745                 750

Trp Ser Asp Gly Ser Pro Val Val Ser Ser Phe Leu Asp Asn Ala
            755                 760                 765

Tyr Phe Glu Glu Asp Ala Lys Asn Cys Ala Val Tyr Lys Ala Asn
            770                 775                 780

Lys Thr Leu Leu Pro Ser Asn Cys Ala Ser Lys His Glu Trp Ile
            785                 790                 795

Cys Arg Ile Pro Arg Asp Val Arg Pro Lys Phe Pro Asp Trp Tyr
            800                 805                 810

Gln Tyr Asp Ala Pro Trp Leu Phe Tyr Gln Asn Ala Glu Tyr Leu
            815                 820                 825

Phe His Thr His Pro Ala Glu Trp Ala Thr Phe Glu Phe Val Cys
            830                 835                 840

Gly Trp Leu Arg Ser Asp Phe Leu Thr Ile Tyr Ser Ala Gln Glu
            845                 850                 855

Gln Glu Phe Ile His Ser Lys Ile Lys Gly Leu Thr Lys Tyr Gly
            860                 865                 870

Val Lys Trp Trp Ile Gly Leu Glu Glu Gly Ala Arg Asp Gln
            875                 880                 885

Ile Gln Trp Ser Asn Gly Ser Pro Val Ile Phe Gln Asn Trp Asp
            890                 895                 900

Lys Gly Arg Glu Glu Arg Val Asp Ser Gln Arg Lys Arg Cys Val
            905                 910                 915

Phe Ile Ser Ser Ile Thr Gly Leu Trp Gly Thr Glu Asn Cys Ser
            920                 925                 930

Val Pro Leu Pro Ser Ile Cys Lys Arg Val Lys Ile Trp Val Ile
            935                 940                 945

Glu Lys Glu Lys Pro Pro Thr Gln Pro Gly Thr Cys Pro Lys Gly
            950                 955                 960

Trp Leu Tyr Phe Asn Tyr Lys Cys Phe Leu Val Thr Ile Pro Lys
            965                 970                 975

Asp Pro Arg Glu Leu Lys Thr Trp Thr Gly Ala Gln Glu Phe Cys
            980                 985                 990

Val Ala Lys Gly Gly Thr Leu Val Ser Ile Lys Ser Glu Leu Glu
            995                1000                1005

Gln Ala Phe Ile Thr Met Asn Leu Phe Gly Gln Thr Thr Asn Val
           1010                1015                1020

Trp Ile Gly Leu Gln Ser Thr Asn His Glu Lys Trp Val Asn Gly
           1025                1030                1035

Lys Pro Leu Val Tyr Ser Asn Trp Ser Pro Ser Asp Ile Ile Asn
```

-continued

```
                     1040                1045                1050
Ile Pro Ser Tyr Asn Thr Thr Glu Phe Gln Lys His Ile Pro Leu
                1055                1060                1065
Cys Ala Leu Met Ser Ser Asn Pro Asn Phe His Phe Thr Gly Lys
                1070                1075                1080
Trp Tyr Phe Asp Asp Cys Gly Lys Glu Gly Tyr Gly Phe Val Cys
                1085                1090                1095
Glu Lys Met Gln Asp Thr Leu Glu His His Val Asn Val Ser Asp
                1100                1105                1110
Thr Ser Ala Ile Pro Ser Thr Leu Glu Tyr Gly Asn Arg Thr Tyr
                1115                1120                1125
Lys Ile Ile Arg Gly Asn Met Thr Trp Tyr Ala Ala Gly Lys Ser
                1130                1135                1140
Cys Arg Met His Arg Ala Glu Leu Ala Ser Ile Pro Asp Ala Phe
                1145                1150                1155
His Gln Ala Phe Leu Thr Val Leu Leu Ser Arg Leu Gly His Thr
                1160                1165                1170
His Trp Ile Gly Leu Ser Thr Thr Asp Asn Gly Gln Thr Phe Asp
                1175                1180                1185
Trp Ser Asp Gly Thr Lys Ser Pro Phe Thr Tyr Trp Lys Asp Glu
                1190                1195                1200
Glu Ser Ala Phe Leu Gly Asp Cys Ala Phe Ala Asp Thr Asn Gly
                1205                1210                1215
Arg Trp His Ser Thr Ala Cys Glu Ser Phe Leu Gln Gly Ala Ile
                1220                1225                1230
Cys His Val Val Thr Glu Thr Lys Ala Phe Glu His Pro Gly Leu
                1235                1240                1245
Cys Ser Glu Thr Ser Val Pro Trp Ile Lys Phe Lys Gly Asn Cys
                1250                1255                1260
Tyr Ser Phe Ser Thr Val Leu Asp Ser Arg Ser Phe Glu Asp Ala
                1265                1270                1275
His Glu Phe Cys Lys Ser Glu Gly Ser Asn Leu Leu Ala Ile Arg
                1280                1285                1290
Asp Ala Ala Glu Asn Ser Phe Leu Leu Glu Glu Leu Leu Ala Phe
                1295                1300                1305
Gly Ser Ser Val Gln Met Val Trp Leu Asn Ala Gln Phe Asp Asn
                1310                1315                1320
Asn Asn Lys Thr Leu Arg Trp Phe Asp Gly Thr Pro Thr Glu Gln
                1325                1330                1335
Ser Asn Trp Gly Leu Arg Lys Pro Asp Met Asp His Leu Lys Pro
                1340                1345                1350
His Pro Cys Val Val Leu Arg Ile Pro Glu Gly Ile Trp His Phe
                1355                1360                1365
Thr Pro Cys Glu Asp Lys Lys Gly Phe Ile Cys Lys Met Glu Ala
                1370                1375                1380
Gly Ile Pro Ala Val Thr Ala Gln Pro Glu Lys Gly Leu Ser His
                1385                1390                1395
Ser Ile Val Pro Val Thr Val Thr Leu Thr Leu Ile Ile Ala Leu
                1400                1405                1410
Gly Ile Phe Met Leu Cys Phe Trp Ile Tyr Lys Gln Lys Ser Asp
                1415                1420                1425
Ile Phe Gln Arg Leu Thr Gly Ser Arg Gly Ser Tyr Tyr Pro Thr
                1430                1435                1440
```

```
Leu Asn Phe Ser Thr Ala His Leu Glu Glu Asn Ile Leu Ile Ser
            1445                1450                1455

Asp Leu Glu Lys Asn Thr Asn Asp Glu Glu Val Arg Asp Ala Pro
            1460                1465                1470

Ala Thr Glu Ser Lys Arg Gly His Lys Gly Arg Pro Ile Cys Ile
            1475                1480                1485

Ser Pro
   1487
```

(2) INFORMATION FOR SEQ ID NO:8:

(i) SEQUENCE CHARACTERISTICS:
        (A) LENGTH: 67 amino acids
        (B) TYPE: Amino Acid
        (D) TOPOLOGY: Linear (xi) SEQUENCE DESCRIPTION: SEQ ID NO:8:

```
Met Thr Tyr Asp Glu Ala Ser Ala Tyr Cys Gln Gln Arg Tyr Thr
 1               5                  10                  15

His Leu Val Ala Ile Gln Asn Lys Glu Glu Ile Glu Tyr Leu Asn
                20                  25                  30

Ser Ile Leu Ser Tyr Ser Pro Ser Tyr Tyr Trp Ile Gly Ile Arg
                35                  40                  45

Lys Val Asn Asn Val Trp Val Trp Val Gly Thr Gln Lys Pro Leu
                50                  55                  60

Thr Glu Glu Ala Lys Asn Trp
                65      67
```

(2) INFORMATION FOR SEQ ID NO:9:

(i) SEQUENCE CHARACTERISTICS:
        (A) LENGTH: 67 amino acids
        (B) TYPE: Amino Acid
        (D) TOPOLOGY: Linear (xi) SEQUENCE DESCRIPTION: SEQ ID NO:9:

```
Leu Lys Trp Ser Glu Ala Gln Phe Ser Cys Glu Gln Gln Glu Ala
 1               5                  10                  15

Gln Leu Val Thr Ile Thr Asn Pro Leu Glu Gln Ala Phe Ile Thr
                20                  25                  30

Ala Ser Leu Pro Asn Val Thr Phe Asp Leu Trp Ile Gly Leu His
                35                  40                  45

Ala Ser Gln Arg Asp Phe Gln Trp Val Glu Gln Glu Pro Leu Met
                50                  55                  60

Tyr Ala Asn Trp Ala Thr Trp
                65      67
```

(2) INFORMATION FOR SEQ ID NO:10:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:10:

CCGGAATTCC GGTTTGTTGC CACTGGGAGC AGG                    33

(2) INFORMATION FOR SEQ ID NO:11:

-continued

```
    (i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:11:

CCCAAGCTTG AAGTGGTCAG AGGCACAGTT CTC                                    33

(2) INFORMATION FOR SEQ ID NO:12:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (xi) SEQUENCE DESCRIPTION: SEQ ID NO:12:

GACGGGCCTG GCTGCGTTCC AGGAGGCCG                                         29

(2) INFORMATION FOR SEQ ID NO:13:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (xi) SEQUENCE DESCRIPTION: SEQ ID NO:13:

GAGGCCCAGC TGGGGGCCGG TGCTGGAGT                                         29

(2) INFORMATION FOR SEQ ID NO:14:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO:14:

GGGTGGAGCA GGAGCCTTTG ATGTATGCCA                                        30

(2) INFORMATION FOR SEQ ID NO:15:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO:15:

TTTCAGGTCC AGGGCCAGGA ACCCCAGAGC                                        30
```